United States Patent
Moysey et al.

(10) Patent No.: US 9,617,591 B2
(45) Date of Patent: Apr. 11, 2017

(54) METHOD FOR CHARACTERISING A POLYNUCLEOTIDE BY USING A XPD HELICASE

(71) Applicant: OXFORD NANOPORE TECHNOLOGIES LIMITED, Oxford (GB)

(72) Inventors: Ruth Moysey, Oxford (GB); Andrew John Heron, Oxford (GB); Szabolcs Soeroes, Oxford (GB)

(73) Assignee: Oxford Nanopore Technologies Ltd., Oxford (GB)

(*) Notice: Subject to any disclaimer, the term of this patent is extended or adjusted under 35 U.S.C. 154(b) by 142 days.

(21) Appl. No.: 14/369,024

(22) PCT Filed: Dec. 28, 2012

(86) PCT No.: PCT/GB2012/053273
§ 371 (c)(1),
(2) Date: Jun. 26, 2014

(87) PCT Pub. No.: WO2013/098561
PCT Pub. Date: Jul. 4, 2013

(65) Prior Publication Data
US 2015/0065354 A1  Mar. 5, 2015

Related U.S. Application Data

(60) Provisional application No. 61/581,340, filed on Dec. 29, 2011.

(51) Int. Cl.
*C12Q 1/00* (2006.01)
*C12Q 1/25* (2006.01)
*C12Q 1/68* (2006.01)

(52) U.S. Cl.
CPC ................ *C12Q 1/6869* (2013.01)

(58) Field of Classification Search
None
See application file for complete search history.

(56) References Cited

U.S. PATENT DOCUMENTS

| | | | |
|---|---|---|---|
| 7,338,807 B2 | 3/2008 | Harris et al. | |
| 7,745,116 B2 | 6/2010 | Williams | |
| 8,105,846 B2 | 1/2012 | Bayley et al. | |
| 8,785,211 B2 | 7/2014 | Bayley et al. | |
| 8,828,208 B2 | 9/2014 | Canas et al. | |
| 2006/0063171 A1 | 3/2006 | Akeson et al. | |
| 2009/0256116 A1 | 10/2009 | Shumaker-Parry et al. | |
| 2010/0092960 A1 | 4/2010 | Fehr | |
| 2010/0120098 A1 | 5/2010 | Grunenwald et al. | |
| 2010/0221212 A1 | 9/2010 | Stagliano et al. | |
| 2011/0177498 A1 | 7/2011 | Clarke et al. | |
| 2011/0229877 A1 | 9/2011 | Jayasinghe et al. | |
| 2012/0058468 A1 | 3/2012 | Mckeown | |
| 2012/0107802 A1 | 5/2012 | Stoddart et al. | |
| 2013/0149769 A1 | 6/2013 | Kizaki et al. |
| 2014/0051069 A1 | 2/2014 | Jayasinghe et al. |
| 2014/0186823 A1 | 7/2014 | Clarke et al. |
| 2014/0255921 A1 | 9/2014 | Moysey et al. |
| 2014/0262784 A1 | 9/2014 | Clarke et al. |
| 2014/0335512 A1 | 11/2014 | Moysey et al. |
| 2015/0008126 A1 | 1/2015 | Maglia et al. |
| 2015/0031020 A1 | 1/2015 | Jayasinghe et al. |
| 2015/0152492 A1 | 6/2015 | Brown et al. |
| 2015/0191709 A1 | 7/2015 | Heron et al. |
| 2015/0197796 A1 | 7/2015 | White et al. |
| 2015/0218629 A1 | 8/2015 | Heron et al. |
| 2016/0257942 A1 | 9/2016 | Bruce et al. |

FOREIGN PATENT DOCUMENTS

| WO | 00/28312 A1 | 5/2000 |
|---|---|---|
| WO | 2005/124888 A1 | 12/2005 |
| WO | WO 2006/028508 | 3/2006 |
| WO | 2006/100484 A2 | 9/2006 |
| WO | WO 2007/057668 | 5/2007 |
| WO | 2008/102120 A1 | 8/2008 |
| WO | 2008/102121 A1 | 8/2008 |
| WO | WO 2009/035647 | 3/2009 |
| WO | WO 2009/044170 A1 | 4/2009 |
| WO | 2009/077734 A2 | 6/2009 |
| WO | 2010/004265 A1 | 1/2010 |
| WO | 2010/004273 A1 | 1/2010 |
| WO | WO 2010/034018 | 3/2010 |
| WO | 2010/086603 A1 | 8/2010 |
| WO | WO 2010/086602 A1 | 8/2010 |
| WO | WO 2010/086622 | 8/2010 |
| WO | WO 2010/109197 | 9/2010 |
| WO | 2010/122293 A1 | 10/2010 |
| WO | 2011/067559 A1 | 6/2011 |
| WO | WO 2012/033524 A2 | 3/2012 |
| WO | WO 2013/014451 A1 | 1/2013 |
| WO | WO 2013/057495 A2 | 4/2013 |
| WO | WO 2013/098561 A1 | 7/2013 |
| WO | WO 2013/098562 A2 | 7/2013 |
| WO | WO 2014/013259 A1 | 1/2014 |
| WO | WO 2014/013260 A1 | 1/2014 |
| WO | WO 2014/013262 A1 | 1/2014 |
| WO | WO 2014/158665 A1 | 10/2014 |

OTHER PUBLICATIONS

Altschul, Stephen F. et al., "Basic Local Alignment Search Tool," J. Mol. Biol., vol. 215:403-410 (1990).

(Continued)

*Primary Examiner* — Suzanne M Noakes
*Assistant Examiner* — Jae W Lee
(74) *Attorney, Agent, or Firm* — Wolf, Greenfield & Sacks, P.C.

(57) ABSTRACT

The invention relates to a new method of characterizing a target polynucleotide. The method uses a pore and an XPD helicase. The helicase controls the movement of the target polynucleotide through the pore.

12 Claims, 7 Drawing Sheets

(56) References Cited

OTHER PUBLICATIONS

Altschul, Stephen F., "A Protein Alignment Scoring System Sensitive at All Evolutionary Distances," J. Mol. Evol., vol. 36:290-300 (1993).
Benner, Seico et al., "Sequence-specific detection of individual DNA polymerase complexes in real time using a nanopore," Nature Biotechnology, vol. 2:718-724 (2007).
Braha, Orit et al., "Designed protein pores as components for biosensors," Chemistry & Biology, vol. 4:497-505 (1997).
Deamer, David, "Nanopore analysis of nucleic acids bound to exonucleases and polymerases," Annu. Rev. Biophys., vol. 39:79-90 (2010).
Devereux, John et al., "A comprehensive set of sequence analysis programs for the VAX," Nucleic Acids Research, vol. 12(1):387-395 (1984).
Grant, Gian Paola G. et al., "A facile method for attaching nitroxide spin labels at the 5' terminus of nucleic acids," Nucleic Acids Research, vol. 35(10):e77, doi:10.1093/nar/gkm240, 8 pages (2007).
Holden, Matthew A. et al., "Direct Introduction of Single Protein Channels and Pores into Lipid Bilayers," J. Am. Chem. Soc., vol. 127:6502-6503 (2005).
Holden, Matthew A. et al., "Functional Bionetworks from Nanoliter Water Droplets," J. Am. Chem. Soc., vol. 129:8650-8655 (2007).
Hornblower, Breton et al., "Single-molecule analysis of DNA-protein complexes using nanopores," Nature Methods, vol. 4(4):315-317 (2007).
Ivanov, Aleksandar P. et al., "DNA Tunneling Detector Embedded in a Nanopore," Nano Letters, vol. 11:279-285 (2011).
Kumar, Abhay et al., "Nonradioactive Labeling of Synthetic Oligonucleotide Probes with Terminal Deoxynucleotidyl Transferase," Analytical Biochemistry, vol. 169:376-382 (1988).
Lieberman, Kate R. et al., "Processive Replication of Single DNA Molecules in a Nanopore Catalyzed by phi29 DNA Polymerase," J. Am. Chem. Soc., vol. 132:17961-17972 (2010).
Liu, Huanting et al., "Structure of the DNA Repair Helicase XPD," Cell, vol. 133:801-812 (2008).
Montal, M. et al., "Formation of Biomolecular Membranes from Lipid Monolayers and a Study of Their Electrical Properties," Proc. Natl. Acad. Sci. USA, vol. 69(12):3561-3566 (1972).
Nikolov, Vesselin et al., "Behavior of Giant Vesicles with Anchored DNA Molecules," Biophysical Journal, vol. 92:4356-4368 (2007).
Pfeiffer, Indriati et al., "Bivalent Cholesterol-Based Coupling of Oligonucleotides to Lipid Membrane Assemblies," J. Am. Chem. Soc., vol. 126:10224-10225 (2004).
Soni, Gautam V. et al., "Synchronous optical and electrical detection of biomolecules traversing through solid-state nanopores," Review of Scientific Instruments, vol. 81:014301-1-014301-7 (2010).
Stoddart, David et al., "Single-nucleotide discimination in immobilized DNA oligonucleotides with a biological nanopore," PNAS, vol. 106(19):7702-7707 (2009).
Troutt, Anthony B. et al., "Ligation-anchored PCR: a simple amplification technique with single-sided specificity," Proc. Natl. Acad. Sci. USA, vol. 89:9823-9825 (1992).
Van Lengerich, Bettina et al., "Covalent attachment of lipid vesicles to a fluid supported bilayer allows observation of DNA-mediated vesicle interactions," Langmuir, vol. 26(11):8666-8672 (2010).
Yoshina-Ishii, Chiaki et al., "Arrays of Mobile Tethered Vesicles on Supported Lipid Bilayers," J. Am. Chem. Soc., vol. 125:3696-3697 (2003).
U.S. Appl. No. 13/002,709, filed May 13, 2011, Lakmal Jayasinghe.
U.S. Appl. No. 13/968,778, filed Aug. 16, 2013, Lakmal Jayasinghe.
U.S. Appl. No. 14/455,394, filed Aug. 8, 2014, Lakmal Jayasinghe.
U.S. Appl. No. 13/002,717, filed Mar. 30, 2011 James Clarke.
U.S. Appl. No. 13/147,171, filed Nov. 10, 2011, Ruth Moysey.
U.S. Appl. No. 14/071,731, filed Nov. 5, 2013, Ruth Moysey.
U.S. Appl. No. 13/260,178, filed Jan. 17, 2012, David Stoddart.
U.S. Appl. No. 13/265,448, filed Feb. 10, 2012, Antonio Canas.
U.S. Appl. No. 13/512,937, filed Sep. 6, 2012, Clive Gavin Brown.
U.S. Appl. No. 14/302,303, filed Jun. 11, 2014, Clive Gavin Brown.
U.S. Appl. No. 12/339,956, filed Dec. 19, 2008, Stuart William Reid.
U.S. Appl. No. 14/302,287, filed Jun. 11, 2014, Stuart William Reid.
U.S. Appl. No. 13/002,709, Mar. 10, 2014, Marianne P. Allen.
U.S. Appl. No. 13/002,709, Jun. 27, 2013, Marianne P. Allen.
U.S. Appl. No. 13/002,709, Dec. 21, 2012, Sandra L. Wegert.
U.S. Appl. No. 13/968,778, Jul. 9, 2014, Marianne P. Allen.
U.S. Appl. No. 13/002,717, Apr. 3, 2014, Brian J. Gangle.
U.S. Appl. No. 13/002,717, Dec. 20, 2012, Sandra L. Wegert.
U.S. Appl. No. 13/147,171, May 6, 2013, Nashaat T. Nashed.
U.S. Appl. No. 13/147,171, Jan. 3, 2013, Nashaat T. Nashed.
U.S. Appl. No. 13/260,178, Jan. 14, 2014, Robert Thomas Crow.
U.S. Appl. No. 13/260,178, May 9, 2013, Robert Thomas Crow.
U.S. Appl. No. 13/260,178, Feb. 20, 2013, Robert Thomas Crow.
U.S. Appl. No. 13/265,448, Apr. 28, 2014, Jennifer M. Dieterle.
U.S. Appl. No. 13/265,448, Jan. 10, 2014, Jennifer M. Dieterle.
U.S. Appl. No. 12/339,956, Feb. 27, 2014, Louis J. Rufo.
U.S. Appl. No. 12/339,956, Jun. 12, 2013, Louis J. Rufo.
U.S. Appl. No. 12/339,956, Oct. 10, 2012, Louis J. Rufo.
U.S. Appl. No. 12/339,956, Mar. 28, 2012, Louis J. Rufo.
U.S. Appl. No. 12/339,956, Sep. 8, 2011, Louis J. Rufo.
U.S. Appl. No. 12/339,956, Apr. 25, 2011, Louis J. Rufo.
U.S. Appl. No. 15/113,174, filed Jul. 21, 2016, Bowen et al.
PCT/GB2012/053273, Jul. 10, 2014, International Preliminary Report on Patentability.
PCT/GB2012/053273, Apr. 24, 2013, International Search Report and Written Opinion.
Blast ® NCBI. Sequence ID No. 10; ZSYBNHWV114. Sep. 18, 2015.
Blast ® NCBI. Sequence ID No. 52; ZT1133A811N. Sep. 18, 2015.
Genbank Submission. NCBI; Accession No. AM778123. Richards et al.; Sep. 18, 2008.
GenPept Accession No. XP 003728286. Jun. 7, 2012.
Press release: Oxford Nanopore introduces DNA 'strand sequencing' on the high-throughput GridION platform and presents MinION, a sequencer the size of a USB; memory stick, Feb. 2012.
UniProt Database accession No. a4s1e1 sequence. May 15, 2007.
UniProt Database accession No. b4kac8 sequence. Sep. 23, 2008.
UniProt Database accession No. D0KN27. Dec. 15, 2009.
UniProt Database accession No. e1qus6 sequence. Nov. 30, 2010.
UniProt Database accession No. i3d0e7 sequence. Jul. 11, 2012.
UniProt Database accession No. I7J3V8 sequence. Oct. 3, 2012.
UniProt Database accession No. k0im99 sequence. Nov. 28, 2012.
UniProt Database accession No. k7nri8 sequence. Feb. 6, 2013.
UniProt Database accession No. Q7Y5C3 sequence. Oct. 1, 2003.
Sequence ID No. 2 Search Results. US-14-351-038-2. Sep. 16, 2015. 69 pages.
[No Author Listed] Antibodies bind specific molecules through their hypervariable loops. 33.3 Antibody Binding. 6th edition. 2007;953-954.
Allen et al., The genome sequence of the psychrophilic archaeon, Methanococcoides burtonii: the role of genome evolution in cold adaptation. ISME J. Sep. 2009;3(9):1012-35. doi: 10.1038/ismej.2009.45.
Astier et al., Toward single molecule DNA sequencing: direct identification of ribonucleoside and deoxyribonucleoside 5'—monophosphates by using an engineered protein nanopore equipped with a molecular adapter. J Am Chem Soc. Feb. 8, 2006;128(5):1705-10.
Butler et al., Single-molecule DNA detection with an engineered MspA protein nanopore. Proc Natl Acad Sci U S A. Dec. 30, 2008;105(52):20647-52. doi: 10.1073/pnas.0807514106. Epub Dec. 19, 2008.
Byrd et al., A parallel quadruplex DNA is bound tightly but unfolded slowly by pif1 helicase. J Biol Chem. Mar. 6, 2015;290(10):6482-94. doi:10.1074/jbc.M114.630749. Epub Jan 14, 2015.
Cheng et al., Functional characterization of the multidomain F plasmid TraI relaxase-helicase. J Biol Chem. Apr. 8, 2011;286(14):12670-82. doi: 10.1074/jbc.M110.207563. Epub Feb. 2, 2011.

(56) References Cited

OTHER PUBLICATIONS

Comer et al., Microscopic mechanics of hairpin DNA translocation through synthetic nanopores. Biophys J. Jan. 2009;96(2):593-608. doi: 10.1016/j.bpj.2008.09.023.
Derrington et al., Nanopore DNA sequencing with MspA. Proc Natl Acad Sci U S A. Sep. 14, 2010;107(37):16060-5. doi: 10.1073/pnas.1001831107. Epub Aug. 26, 2010.
Dostál et al., Tracking F plasmid TraI relaxase processing reactions provides insight into F plasmid transfer. Nucleic Acids Res. Apr. 2011;39(7):2658-70. doi: 10.1093/nar/gkq1137. Epub Nov. 24, 2010.
Dou et al., The DNA binding properties of the *Escherichia coli* RecQ helicase. J Biol Chem. Feb. 20, 2004;279(8):6354-63. Epub Dec. 9, 2003.
Fairman-Williams et al., SF1 and SF2 helicases: family matters. Curr Opin Struct Biol. Jun. 2010;20(3):313-24. doi:10.1016/j.sbi.2010.03.011. Epub Apr. 22, 2010.
Garalde et al., Highly parallel direct RNA sequencing on an array of nanopores. bioRxiv. 2016. doi: http://dx.doi.org/10.1101/068809.
Garcillán-Barcia et al., The diversity of conjugative relaxases and its application in plasmid classification. FEMS Microbiol Rev. May 2009;33(3):657-87.
Gonzalez-Perez et al., Biomimetic triblock copolymer membrane arrays: a stable template for functional membrane proteins. Langmuir. Sep. 15, 2009;25(18):10447-50. doi: 10.1021/la902417m.
Graham et al., Sequence-specific assembly of FtsK hexamers establishes directional translocation on DNA. Proc Natl Acad Sci U S A. Nov. 23, 2010;107(47):20263-8. doi: 10.1073/pnas.1007518107. Epub Nov. 3, 2010.
Green et al., Quantitative evaluation of the lengths of homobifunctional protein cross-linking reagents used as molecular rulers. Protein Sci. Jul. 2001;10(7):1293-304.
Hammerstein et al., Subunit dimers of alpha-hemolysin expand the engineering toolbox for protein nanopores. J Biol Chem. Apr. 22, 2011;286(16):14324-34. doi: 10.1074/jbc.M111.218164. Epub Feb. 15, 2011.
He et al, The T4 phage SF1B helicase Dda is structurally optimized to perform DNA strand separation. Structure. Jul. 3, 2012;20(7):1189-200. doi:10.1016/j.str.2012.04.013. Epub May 31, 2012.
Hopfner et al., Mechanisms of nucleic acid translocases: lessons from structural biology and single-molecule biophysics. Curr Opin Struct Biol. Feb. 2007;17(1):87-95. Epub Dec. 6, 2006.
Howorka et al., Nanopore analytics: sensing of single molecules. Chem Soc Rev. Aug. 2009;38(8):2360-84. doi: 10.1039/b813796j. Epub Jun. 15, 2009.
James, Aptamers. Encyclopedia of Analytical Chemistry. R.A. Meyers (Ed.). John Wiley & Sons Ltd, Chichester, 2000. 4848-4871.
Jezewska et al., Interactions of *Escherichia coli* replicative helicase PriA protein with single-stranded DNA. Biochemistry. Aug. 29, 2000;39(34):10454-67. Abstract only.
Kafri et al., Dynamics of molecular motors and polymer translocation with sequence heterogeneity. Biophys J. Jun. 2004;86(6):3373-91.
Kar et al., Defining the structure-function relationships of bluetongue virus helicase protein VP6. J Virol. Nov. 2003;77(21):11347-56.
Keyser, Controlling molecular transport through nanopores. J R Soc Interface. Oct. 7, 2011;8(63):1369-78. doi: 10.1098/rsif.2011.0222. Epub Jun. 29, 2011.
Khafizov, Single Molecule Force Spectroscopy of Single Stranded Dna Binding Protein and Rep Helicase. University of Illinois at Urbana-Champaign Dissertation. 2012.
Korolev et al., Major domain swiveling revealed by the crystal structures of complexes of E. coli Rep helicase bound to single-stranded DNA and ADP. Cell. Aug. 22, 1997;90(4):635-47.
Kuper et al., Functional and structural studies of the nucleotide excision repair helicase XPD suggest a polarity for DNA translocation. EMBO J. Jan. 18, 2012;31(2):494-502. doi: 10.1038/emboj.2011.374.
Lee et al., Direct imaging of single UvrD helicase dynamics on long single-stranded DNA. Nat Commun 2013;4:1878. doi:10.1038/ncomms2882.
Liu et al., Adding new chemistries to the genetic code. Annu Rev Biochem. 2010;79:413-44. doi: 10.1146/annurev.biochem.052308.105824.
Lohman et al., Mechanisms of helicase-catalyzed DNA unwinding. Annu Rev Biochem. 1996;65:169-214.
Lohman et al., Non-hexameric DNA helicases and translocases:mechanisms and regulation. Nat Rev Mol Cell Biol. May 2008;9(5):391-401. doi:10.1038/nrm2394.
Ma et al., Bright functional rotaxanes. Chem Soc Rev. Jan. 2010;39(1):70-80. doi: 10.1039/b901710k. Epub Jul. 21, 2009.
Marini et al., A human DNA helicase homologous to the DNA cross-link sensitivity protein Mus308. J Biol Chem. Mar. 8, 2002;277(10):8716-23. Epub Dec. 18, 2001.
Morris et al., Evidence for a functional monomeric form of the bacteriophage T4 DdA helicase. Dda does not form stable oligomeric structures. J Biol Chem. Jun. 8, 2001;276(23):19691-8. Epub Feb. 27, 2001.
O'Shea et al., X-ray structure of the GCN4 leucine zipper, a two-stranded, parallel coiled coil. Science. Oct. 25, 1991;254(5031):539-44.
Pinero-Fernandez et al., Indole transport across *Escherichia coli* membranes. J Bacteriol. Apr. 2011;193(8):1793-8. doi:10.1128/Jb.01477-10. Epub Feb. 4, 2011.
Raney et al., Structure and Mechanisms of SF1 DNA Helicases. Adv Exp Med Biol. 2013;767:17-46. doi: 10.1007/978-01-4614-5037-5_2.
Remaut et al., Protein-protein interaction through beta-strand addition. Trends Biochem Sci. Aug. 2006;31(8):436-44. Epub Jul. 7, 2006.
Richards et al., Structure of the DNA repair helicase he1308 reveals DNA binding and autoinhibitory domains. J Biol Chem. Feb. 22, 2008;283(8):5118-26. Epub Dec. 4, 2007.
Rudolf et al., The DNA repair helicases XPD and FancJ have essential iron-sulfur domains. Mol Cell. Sep. 15, 2006;23(6):801-8.
Rudolf et al., The helicase XPD unwinds bubble structures and is not stalled by DNA lesions removed by the nucleotide excision repair pathway. Nucleic Acids Res. Jan. 2010;38(3):931-41. doi:10.1093/nar/gkp1058.
Saariaho et al., Characteristics of MuA transposase-catalyzed processing of model transposon end DNA hairpin substrates. Nucleic Acids Res. Jun. 6, 2006;34(10):3139-49. Print 2006.
Satapathy et al., ATPase activity of RecD is essential for growth of the Antarctic Pseudomonas syringae Lz4W at low temperature. FEBS J. Apr. 2008;275(8):1835-51. doi:10.1111/j.1742-4658.2008.06342.x. Epub Mar. 9, 2008.
Schneider et al., DNA sequencing with nanopores. Nat Biotechnol. Apr. 10, 2012;30(4):326-8. doi: 10.1038/nbt.2181.
Singleton et al., Structure and mechanism of helicases and nucleic acid translocases. Annu Rev Biochem. 2007;76:23-50.
Tuteja et al., Unraveling DNA helicases. Motif, structure, mechanism and function. Eur J Biochem. May 2004;271(10):1849-63. Review. Erratum in: Eur J Biochem. Aug. 2004;271(15):3283.
Van Heel et al., Single-particle electron cryo-microscopy:towards atomic resolution. Q Rev Biophys. Nov. 2000;33(4):307-69.
Venkatesan et al., Nanopore sensors for nucleic acid analysis. Nat Nanotechnol. Sep. 18, 2011;6(10):615-24. doi: 10.1038/nnano.2011.129.
Vinson, Proteins in motion. Introduction. Science. Apr. 10, 2009;324(5924):197. doi: 10.1126/science.324.5924.197.
White, Structure, function and evolution of the XPD family of iron-sulfur-containing 5'→3' DNA helicases. Biochem Soc Trans. 2009;37:547-551.
Woodman et al., Archaeal He1308 domain V couples DNA binding to ATP hydrolysis and positions DNA for unwinding over the helicase ratchet. J Mol Biol. Dec. 14, 2007;374(5):1139-44. Epub Oct. 10, 2007.

METHOD FOR CHARACTERISING A POLYNUCLEOTIDE BY USING A XPD HELICASE

CROSS-REFERENCE TO RELATED APPLICATIONS

This application is a 35 U.S.C. 371 national stage filing of International Application No. PCT/GB2012/053273, filed on Dec. 28, 2012, which claims priority to and benefit of U.S. Provisional Application No. 61/581,340, filed Dec. 29, 2011, the entire contents of each of which are hereby incorporated by reference herein.

FIELD OF THE INVENTION

The invention relates to a new method of characterising a target polynucleotide. The method uses a pore and an XPD helicase. The helicase controls the movement of the target polynucleotide through the pore.

BACKGROUND OF THE INVENTION

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the "Strand Sequencing" method, a single polynucleotide strand is passed through the pore and the identity of the nucleotides are derived. Strand Sequencing can involve the use of a nucleotide handling protein to control the movement of the polynucleotide through the pore.

SUMMARY OF THE INVENTION

The inventors have demonstrated that an XPD helicase can control the movement of a polynucleotide through a pore especially when a potential, such as a voltage, is applied. The helicase is capable of moving a target polynucleotide in a controlled and stepwise fashion against or with the field resulting from the applied voltage. Surprisingly, the helicase is capable of functioning at a high salt concentration which is advantageous for characterising the polynucleotide and, in particular, for determining its sequence using Strand Sequencing. This is discussed in more detail below.

Accordingly, the invention provides a method of characterising a target polynucleotide, comprising:
(a) contacting the target polynucleotide with a transmembrane pore and a XPD helicase such that the target polynucleotide moves through the pore and the XPD helicase controls the movement of the target polynucleotide through the pore; and
(b) taking one or more measurements as the polynucleotide moves with respect to the pore wherein the measurements are indicative of one or more characteristics of the target polynucleotide and thereby characterising the target polynucleotide.

The invention also provides:
a method of forming a sensor for characterising a target polynucleotide, comprising forming a complex between a pore and an XPD helicase and thereby forming a sensor for characterising the target polynucleotide;
use of an XPD helicase to control the movement of a target polynucleotide through a pore;
a kit for characterising a target polynucleotide comprising (a) a pore and (b) an XPD helicase; and
an analysis apparatus for characterising target polynucleotides in a sample, comprising a plurality of pores and a plurality of an XPD helicase;
a method of characterising a target polynucleotide, comprising:
(a) contacting the target polynucleotide with a XPD helicase such that the XPD helicase controls the movement of the target polynucleotide; and
(b) taking one or more measurements as the XPD helicase controls the movement of the polynucleotide wherein the measurements are indicative of one or more characteristics of the target polynucleotide and thereby characterising the target polynucleotide;
use of a XPD helicase to control the movement of a target polynucleotide during characterisation of the polynucleotide;
use of a XPD helicase to control the movement of a target polynucleotide during sequencing of part or all of the polynucleotide;
an analysis apparatus for characterising target polynucleotides in a sample, characterised in that it comprises a XPD helicase; and
a kit for characterising a target polynucleotide comprising (a) an analysis apparatus for characterising target polynucleotides and (b) a XPD helicase.

DESCRIPTION OF THE SEQUENCE LISTING

Figure 1A:
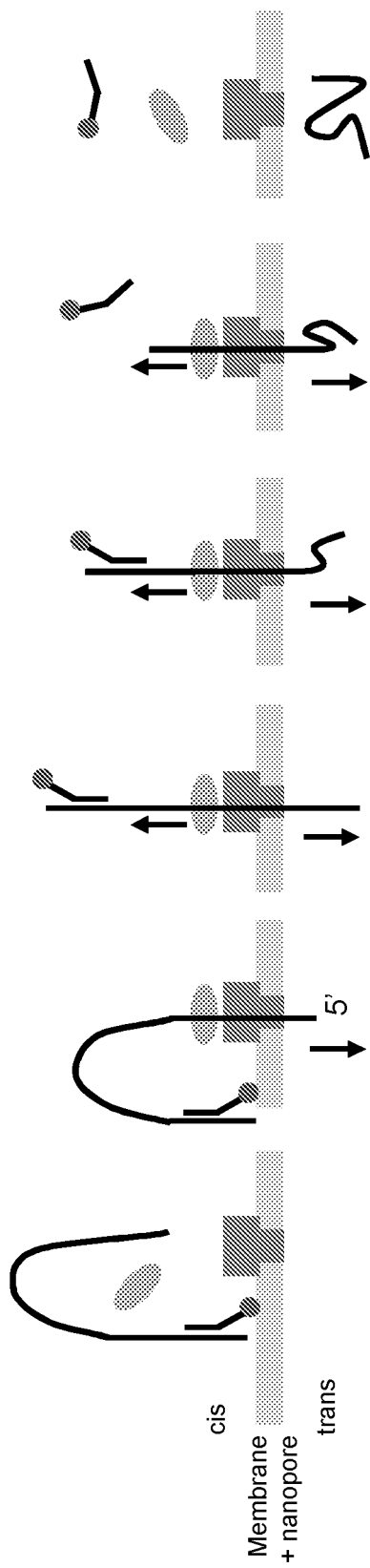
FIG. 1. A) Example schematic of use of a helicase to control DNA movement through a nanopore. The arrows shown on the trans side show the direction of motion of the DNA. The arrows on the cis side show direction of motion of the helicase relative to the DNA. From left to right) A ssDNA substrate (FIG. 1B) with an annealed primer containing a cholesterol-tag is added to the cis side of the bilayer. The cholesterol tag binds to the bilayer, enriching the substrate at the bilayer surface. Helicase added to the cis compartment binds to the DNA. In the presence of divalent metal ions and NTP substrate, the helicase moves along the DNA. Under an applied voltage, the DNA substrate is captured by the nanopore via the leader section on the DNA. The DNA is pulled through the pore under the force of the applied potential until a helicase, bound to the DNA, contacts the top of the pore, preventing further uncontrolled DNA translocation. The helicase movement along the DNA in a 5' to 3' direction facilitates the controlled translocation of the threaded DNA through the pore with the applied field. The helicase facilitates translocation of the DNA through the nanopore, feeding it into the trans compartment. The last section of DNA to pass through the nanopore is the 3' end. When the helicase has facilitated complete translocation of the DNA through the nanopore the helicase dissociates from the strand. B) One of the DNA substrate designs used in the Example.

SEQ ID NO: 1 shows the codon optimised polynucleotide sequence encoding the MS-B1 mutant MspA monomer. This mutant lacks the signal sequence and includes the following mutations: D90N, D91N, D93N, D118R, D134R and E139K.

SEQ ID NO: 2 shows the amino acid sequence of the mature form of the MS-B1 mutant of the MspA monomer. This mutant lacks the signal sequence and includes the following mutations: D90N, D91N, D93N, D118R, D134R and E139K.

SEQ ID NO: 3 shows the polynucleotide sequence encoding one subunit of α-hemolysin-E111N/K147N (α-HL-NN; Stoddart et al., PNAS, 2009; 106(19): 7702-7707).

SEQ ID NO: 4 shows the amino acid sequence of one subunit of α-HL-NN.

SEQ ID NOs: 5 to 7 show the amino acid sequences of MspB, C and D.

SEQ ID NOs: 8 and 9 show the amino acid sequences of XPD motifs V and VI.

SEQ ID NOs: 10 to 62 show the amino acid sequences of the XPD helicases in Table 5.

SEQ ID NOs: 63 to 68 show the sequences used in the Examples.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a pore" includes two or more such pores, reference to "a helicase" includes two or more such helicases, reference to "a polynucleotide" includes two or more such polynucleotides, and the like.

All publications, patents and patent applications cited herein, whether supra or infra, are hereby incorporated by reference in their entirety.

Methods of the Invention

The invention provides a method of characterising a target polynucleotide. The method comprises contacting the target polynucleotide with a transmembrane pore and an XPD helicase such that the target polynucleotide moves through the pore and the XPD helicase controls the movement of the target polynucleotide through the pore. One or more characteristics of the target polynucleotide are then measured as the polynucleotide moves with respect to the pore using standard methods known in the art. One or more characteristics of the target polynucleotide are preferably measured as the polynucleotide moves through the pore. Steps (a) and (b) are preferably carried out with a potential applied across the pore. As discussed in more detail below, the applied potential typically results in the formation of a complex between the pore and the helicase. The applied potential may be a voltage potential. Alternatively, the applied potential may be a chemical potential. An example of this is using a salt gradient across an amphiphilic layer. A salt gradient is disclosed in Holden et al., J Am Chem. Soc. 2007 Jul. 11; 129(27):8650-5.

In some instances, the current passing through the pore as the polynucleotide moves with respect to the pore is used to determine the sequence of the target polynucleotide. This is Strand Sequencing.

The method has several advantages. First, the inventors have surprisingly shown that XPD helicases have a surprisingly high salt tolerance and so the method of the invention may be carried out at high salt concentrations. In the context of Strand Sequencing, a charge carrier, such as a salt, is necessary to create a conductive solution for applying a voltage offset to capture and translocate the target polynucleotide and to measure the resulting sequence-dependent current changes as the polynucleotide moves with respect to the pore. Since the measurement signal is dependent on the concentration of the salt, it is advantageous to use high salt concentrations to increase the magnitude of the acquired signal. High salt concentrations provide a high signal to noise ratio and allow for currents indicative of the presence of a nucleotide to be identified against the background of normal current fluctuations. For Strand Sequencing, salt concentrations in excess of 100 mM are ideal, for example salt concentrations in excess of 400 mM, 600 mM or 800 mM. The inventors have surprisingly shown that XPD helicases will function effectively at very high salt concentrations such as, for example, 1 M. The invention encompasses helicases which function effectively at salt concentrations in excess of 1M, for example 2M.

Second, when a voltage is applied, XPD helicases can surprisingly move the target polynucleotide in two directions, namely with or against the field resulting from the applied voltage. Hence, the method of the invention may be carried out in one of two preferred modes. Different signals are obtained depending on the direction the target polynucleotide moves with respect to the pore, ie in the direction of or against the field. This is discussed in more detail below.

Third, XPD helicases typically move the target polynucleotide through the pore one nucleotide at a time. XPD helicases can therefore function like a single-base ratchet. This is of course advantageous when sequencing a target polynucleotide because substantially all, if not all, of the nucleotides in the target polynucleotide may be identified using the pore.

Fourth, XPD helicases are capable of controlling the movement of single stranded polynucleotides and double stranded polynucleotides. This means that a variety of different target polynucleotides can be characterised in accordance with the invention.

Fifth, XPD helicases appear very resistant to the field resulting from applied voltages. The inventors have seen very little movement of the polynucleotide under an "unzipping" condition. Unzipping conditions will typically be in the absence of nucleotides, for example the absence of ATP. When the helicase is operating in unzipping mode it acts like a brake preventing the target sequence from moving through the pore too quickly under the influence of the applied voltage. This is important because it means that there are no complications from unwanted "backwards" movements when moving polynucleotides against the field resulting from an applied voltage.

Sixth, XPD helicases are easy to produce and easy to handle. Their use therefore contributed to a straightforward and less expensive method of sequencing.

The method of the invention is for characterising a target polynucleotide. A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the target polynucleotide can be oxidized or methylated. One or more nucleotides in the target polynucleotide may be damaged. One or more nucleotides in the target polynucleotide may be modified, for instance with a label or a tag. The target polynucleotide may comprise one or more spacers.

A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), guanosine monophosphate (GMP), thymidine monophosphate (TMP), uridine monophosphate (UMP), cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP) and deoxycytidine monophosphate (dCMP). The nucleotides are preferably selected from AMP, TMP, GMP, CMP, UMP, dAMP, dTMP, dGMP or dCMP.

A nucleotide may be abasic (i.e. lack a nucleobase).

The polynucleotide may be single stranded or double stranded. At least a portion of the polynucleotide is preferably double stranded.

The polynucleotide can be a nucleic acid, such as deoxyribonucleic acid (DNA) or ribonucleic acid (RNA). The target polynucleotide can comprise one strand of RNA hybridized to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains.

The whole or only part of the target polynucleotide may be characterised using this method. The target polynucleotide can be any length. For example, the polynucleotide can be at least 10, at least 50, at least 100, at least 150, at least 200, at least 250, at least 300, at least 400 or at least 500 nucleotide pairs in length. The polynucleotide can be 1000 or more nucleotide pairs, 5000 or more nucleotide pairs in length or 100000 or more nucleotide pairs in length.

The target polynucleotide is present in any suitable sample. The invention is typically carried out on a sample that is known to contain or suspected to contain the target polynucleotide. Alternatively, the invention may be carried out on a sample to confirm the identity of one or more target polynucleotides whose presence in the sample is known or expected.

The sample may be a biological sample. The invention may be carried out in vitro on a sample obtained from or extracted from any organism or microorganism. The organism or microorganism is typically archaean, prokaryotic or eukaryotic and typically belongs to one the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs. Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

A transmembrane pore is a structure that crosses the membrane to some degree. It permits ions, such as hydrated ions, driven by an applied potential to flow across or within the membrane. The transmembrane pore typically crosses the entire membrane so that ions may flow from one side of the membrane to the other side of the membrane. However, the transmembrane pore does not have to cross the membrane. It may be closed at one end. For instance, the pore may be a well in the membrane along which or into which ions may flow.

Any membrane may be used in accordance with the invention. Suitable membranes are well-known in the art. The membrane is preferably an amphiphilic layer. An amphiphilic layer is a layer formed from amphiphilic molecules, such as phospholipids, which have both at least one hydrophilic portion and at least one lipophilic or hydrophobic portion. The amphiphilic layer may be a monolayer or a bilayer. The amphiphilic layer is typically a planar lipid bilayer or a supported bilayer.

The amphiphilic layer is typically a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000,563 (published as WO 2008/102121), International Application No. PCT/GB08/004,127 (published as WO 2009/077734) and International Application No. PCT/GB2006/001057 (published as WO 2006/100484).

Methods for forming lipid bilayers are known in the art. Suitable methods are disclosed in the Example. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

In a preferred embodiment, the lipid bilayer is formed as described in International Application No. PCT/GB08/004,127 (published as WO 2009/077734).

In another preferred embodiment, the membrane is a solid state layer. A solid-state layer is not of biological origin. In other words, a solid state layer is not derived from or isolated from a biological environment such as an organism or cell, or a synthetically manufactured version of a biologically available structure. Solid state layers can be formed from both organic and inorganic materials including, but not limited to, microelectronic materials, insulating materials such as $Si_3N_4$, $Al_2O_3$, and SiO, organic and inorganic polymers such as polyamide, plastics such as Teflon® or elastomers such as two-component addition-cure silicone rubber, and glasses. The solid state layer may be formed from monatomic layers, such as graphene, or layers that are only a few atoms thick. Suitable graphene layers are disclosed in International Application No. PCT/US2008/010637 (published as WO 2009/035647).

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial lipid bilayer. The layer may comprise other transmembrane and/or intramembrane proteins as well as other molecules in addition to the pore. Suitable apparatus and conditions are discussed below. The method of the invention is typically carried out in vitro.

The polynucleotide may be coupled to the membrane. This may be done using any known method. If the membrane is an amphiphilic layer, such as a lipid bilayer (as discussed in detail above), the polynucleotide is preferably coupled to the membrane via a polypeptide present in the membrane or a hydrophobic anchor present in the membrane. The hydrophobic anchor is preferably a lipid, fatty acid, sterol, carbon nanotube or amino acid.

The polynucleotide may be coupled directly to the membrane. The polynucleotide is preferably coupled to the membrane via a linker. Preferred linkers include, but are not limited to, polymers, such as polynucleotides, polyethylene glycols (PEGs) and polypeptides. If a polynucleotide is coupled directly to the membrane, then some data will be lost as the characterising run cannot continue to the end of the polynucleotide due to the distance between the membrane and the helicase. If a linker is used, then the polynucleotide can be processed to completion. If a linker is used, the linker may be attached to the polynucleotide at any position. The linker is preferably attached to the polynucleotide at the tail polymer.

The coupling may be stable or transient. For certain applications, the transient nature of the coupling is preferred. If a stable coupling molecule were attached directly to either the 5' or 3' end of a polynucleotide, then some data will be lost as the characterising run cannot continue to the end of the polynucleotide due to the distance between the bilayer and the helicase's active site. If the coupling is transient, then when the coupled end randomly becomes free of the bilayer, then the polynucleotide can be processed to completion. Chemical groups that form stable or transient links with the membrane are discussed in more detail below. The polynucleotide may be transiently coupled to an amphiphilic layer, such as a lipid bilayer using cholesterol or a fatty acyl chain. Any fatty acyl chain having a length of from 6 to 30 carbon atoms, such as hexadecanoic acid, may be used.

In preferred embodiments, the polynucleotide is coupled to an amphiphilic layer. Coupling of polynucleotides to synthetic lipid bilayers has been carried out previously with various different tethering strategies. These are summarised in Table 1 below.

TABLE 1

| Attachment group | Type of coupling | Reference |
|---|---|---|
| Thiol | Stable | Yoshina-Ishii, C. and S. G. Boxer (2003). "Arrays of mobile tethered vesicles on supported lipid bilayers."*J Am Chem Soc* 125(13): 3696-7. |
| Biotin | Stable | Nikolov, V., R. Lipowsky, et al. (2007). "Behavior of giant vesicles with anchored DNA molecules." *Biophys J* 92(12): 4356-68 |
| Cholestrol | Transient | Pfeiffer, I. and F. Hook (2004). "Bivalent cholesterol-based coupling of oligonucletides to lipid membrane assemblies." *J Am Chem Soc* 126(33): 10224-5 |
| Lipid | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Polynucleotides may be functionalized using a modified phosphoramidite in the synthesis reaction, which is easily compatible for the addition of reactive groups, such as thiol, cholesterol, lipid and biotin groups. These different attachment chemistries give a suite of attachment options for polynucleotides. Each different modification group tethers the polynucleotide in a slightly different way and coupling is not always permanent so giving different dwell times for the polynucleotide to the bilayer. The advantages of transient coupling are discussed above.

Coupling of polynucleotides can also be achieved by a number of other means provided that a reactive group can be added to the polynucleotide. The addition of reactive groups to either end of DNA has been reported previously. A thiol group can be added to the 5' of ssDNA using polynucleotide kinase and ATPγS (Grant, G. P. and P. Z. Qin (2007). "A facile method for attaching nitroxide spin labels at the 5' terminus of nucleic acids." *Nucleic Acids Res* 35(10): e77). A more diverse selection of chemical groups, such as biotin, thiols and fluorophores, can be added using terminal transferase to incorporate modified oligonucleotides to the 3' of ssDNA (Kumar, A., P. Tchen, et al. (1988) "Nonradioactive labeling of synthetic oligonucleotide probes with terminal deoxynucleotidyl transferase." *Anal Biochem* 169(2): 376-82).

Alternatively, the reactive group could be considered to be the addition of a short piece of DNA complementary to one already coupled to the bilayer, so that attachment can be achieved via hybridisation. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." *Proc Natl Acad Sci USA* 89(20): 9823-5). Alternatively either ssDNA or dsDNA could be ligated to native dsDNA and then the two strands separated by thermal or chemical denaturation. To native dsDNA, it is possible to add either a piece of ssDNA to one or both of the ends of the duplex, or dsDNA to one or both ends. Then, when the duplex is melted, each single strand will have either a 5' or 3' modification if ssDNA was used for ligation or a modification at the 5' end, the 3' end or both if dsDNA was used for ligation. If the polynucleotide is a synthetic strand, the coupling chemistry can be incorporated during the chemical synthesis of the polynucleotide. For instance, the polynucleotide can be synthesized using a primer a reactive group attached to it.

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. By using an antisense primer that has a reactive group, such as a cholesterol, thiol, biotin or lipid, each copy of the target DNA amplified will contain a reactive group for coupling.

The transmembrane pore is preferably a transmembrane protein pore. A transmembrane protein pore is a protein structure that crosses the membrane to some degree. It permits ions driven by an applied potential to flow across or within the membrane. A transmembrane protein pore is typically a polypeptide or a collection of polypeptides that permits ions, such as analytes, to flow from one side of a membrane to the other side of the membrane. However, the transmembrane protein pore does not have to cross the membrane. It may be closed at one end. For instance, the transmembrane pore may form a well in the membrane along which or into which ions may flow. The transmembrane protein pore preferably permits analytes, such as nucleotides, to flow across or within the membrane, such as a lipid bilayer. The transmembrane protein pore allows a polynucleotide, such as DNA or RNA, to be moved through the pore.

The transmembrane protein pore may be a monomer or an oligomer. The pore is preferably made up of several repeating subunits, such as 6, 7, 8 or 9 subunits. The pore is preferably a hexameric, heptameric, octameric or nonameric pore.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and α outer membrane proteins, such as WZA and ClyA toxin. The transmembrane pore may be derived from Msp or from α-hemolysin (α-HL).

The transmembrane protein pore is preferably derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A monomer derived from Msp comprises the sequence shown in SEQ ID NO: 2 or a variant thereof. SEQ ID NO: 2 is the MS-(B1)8 mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into an amphihpilic layer along with other appropriate subunits and its ability to oligomerise to form a pore may be determined. Methods are known in the art for inserting subunits into membranes, such as amphiphilic layers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) *Nucleic Acids Research* 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10. Software for performing BLAST analyses is publicly available through the National Center for Biotechnology Information (www.ncbi.nlm.nih.gov/).

SEQ ID NO: 2 is the MS-(B1)8 mutant of the MspA monomer. The variant may comprise any of the mutations in the MspB, C or D monomers compared with MspA. The mature forms of MspB, C and D are shown in SEQ ID NOs: 5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, K47T, I49H, I68V, D91G, A96Q, N102D, S103T, V104I, S136K and G141A. The variant may comprise combinations of one or more of the mutations and substitutions from Msp B, C and D. The variant preferably comprises the mutation L88N. The variant of SEQ ID NO: 2 has the mutation L88N in addition to all the mutations of MS-B1 and is called MS-B2. The pore used in the invention is preferably MS-(B2)8.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 2 below. Where amino acids have similar polarity, this can also be determined by reference to the hydropathy scale for amino acid side chains in Table 3.

TABLE 2

Chemical properties of amino acids

| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, | Thr | polar, hydrophilic, neutral charged (+) |
| Ile | aliphatic, hydrophobic, neutral | Val | aliphatic, hydrophobic, neutral |
| Lys | polar, hydrophilic, charged(+) | Trp | aromatic, hydrophobic, neutral |
| Leu | aliphatic, hydrophobic, neutral | Tyr | aromatic, polar, hydrophobic |

TABLE 3

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 150 or 200 amino acids in length. Such fragments may be used to produce the pores. A fragment preferably comprises the pore forming domain of SEQ ID NO: 2. Fragments must include one of residues 88, 90, 91, 105, 118 and 134 of SEQ ID NO: 2. Typically, fragments include all of residues 88, 90, 91, 105, 118 and 134 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of Msp, which contains a β-barrel, is provided by β-sheets in each subunit. A variant of SEQ ID NO: 2 typically comprises the regions in SEQ ID NO: 2 that form β-sheets. One or more modifications can be made to the regions of SEQ ID NO: 2 that form β-sheets as long as the resulting variant retains its ability to form a pore. A variant of SEQ ID NO: 2 preferably includes one or more modifications, such as substitutions, additions or deletions, within its α-helices and/or loop regions.

The monomers derived from Msp may be modified to assist their identification or purification, for example by the addition of histidine residues (a hist tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating hemolysin hetero-oligomers (Chem. Biol. 1997 July; 4(7):497-505).

The monomer derived from Msp may be labelled with a revealing label. The revealing label may be any suitable label which allows the pore to be detected. Suitable labels include, but are not limited to fluorescent molecules, radio-isotopes, e.g. $^{125}I$, $^{35}S$, enzymes, antibodies, antigens, polynucleotides and ligands such as biotin.

The monomer derived from Msp may also be produced using D-amino acids. For instance, the monomer derived from Msp may comprise a mixture of L-amino acids and D-amino acids. This is conventional in the art for producing such proteins or peptides.

The monomer derived from Msp contains one or more specific modifications to facilitate nucleotide discrimination. The monomer derived from Msp may also contain other non-specific modifications as long as they do not interfere with pore formation. A number of non-specific side chain modifications are known in the art and may be made to the side chains of the monomer derived from Msp. Such modifications include, for example, reductive alkylation of amino acids by reaction with an aldehyde followed by reduction with $NaBH_4$, amidination with methylacetimidate or acylation with acetic anhydride.

The monomer derived from Msp can be produced using standard methods known in the art. The monomer derived from Msp may be made synthetically or by recombinant means. For example, the pore may be synthesized by in vitro translation and transcription (IVTT). Suitable methods for producing pores are discussed in International Application Nos. PCT/GB09/001,690 (published as WO 2010/004273), PCT/GB09/001,679 (published as WO 2010/004265) or PCT/GB10/000,133 (published as WO 2010/086603). Methods for inserting pores into membranes are discussed.

The transmembrane protein pore is also preferably derived from α-hemolysin (α-HL). The wild type α-HL pore is formed of seven identical monomers or subunits (i.e. it is heptameric). The sequence of one monomer or subunit of α-hemolysin-NN is shown in SEQ ID NO: 4. The transmembrane protein pore preferably comprises seven monomers each comprising the sequence shown in SEQ ID NO: 4 or a variant thereof. Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 294 of SEQ ID NO: 4 form loop regions. Residues 113 and 147 of SEQ ID NO: 4 form part of a constriction of the barrel or channel of α-HL.

In such embodiments, a pore comprising seven proteins or monomers each comprising the sequence shown in SEQ ID NO: 4 or a variant thereof are preferably used in the method of the invention. The seven proteins may be the same (homoheptamer) or different (heteroheptamer).

A variant of SEQ ID NO: 4 is a protein that has an amino acid sequence which varies from that of SEQ ID NO: 4 and which retains its pore forming ability. The ability of a variant to form a pore can be assayed using any method known in the art. For instance, the variant may be inserted into an amphiphilic layer, such as a lipid bilayer, along with other appropriate subunits and its ability to oligomerise to form a pore may be determined. Methods are known in the art for inserting subunits into amphiphilic layers, such as lipid bilayers. Suitable methods are discussed above.

The variant may include modifications that facilitate covalent attachment to or interaction with the helicase. The variant preferably comprises one or more reactive cysteine residues that facilitate attachment to the helicase. For instance, the variant may include a cysteine at one or more of positions 8, 9, 17, 18, 19, 44, 45, 50, 51, 237, 239 and 287 and/or on the amino or carboxy terminus of SEQ ID NO: 4. Preferred variants comprise a substitution of the residue at position 8, 9, 17, 237, 239 and 287 of SEQ ID NO: 4 with cysteine (A8C, T9C, N17C, K237C, S239C or E287C). The variant is preferably any one of the variants described in International Application No. PCT/GB09/001,690 (published as WO 2010/004273), PCT/GB09/001,679 (published as WO 2010/004265) or PCT/GB10/000,133 (published as WO 2010/086603).

The variant may also include modifications that facilitate any interaction with nucleotides.

The variant may be a naturally occurring variant which is expressed naturally by an organism, for instance by a Staphylococcus bacterium. Alternatively, the variant may be expressed in vitro or recombinantly by a bacterium such as Escherichia coli. Variants also include non-naturally occurring variants produced by recombinant technology. Over the entire length of the amino acid sequence of SEQ ID NO: 4, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4 over the entire sequence. There may be at least 80%, for example at least 85%, 90% or 95%, amino acid identity over a stretch of 200 or more, for example 230, 250, 270 or 280 or more, contiguous amino acids ("hard homology"). Homology can be determined as discussed above.

Amino acid substitutions may be made to the amino acid sequence of SEQ ID NO: 4 in addition to those discussed above, for example up to 1, 2, 3, 4, 5, 10, 20 or 30 substitutions. Conservative substitutions may be made as discussed above.

One or more amino acid residues of the amino acid sequence of SEQ ID NO: 4 may additionally be deleted from the polypeptides described above. Up to 1, 2, 3, 4, 5, 10, 20 or 30 residues may be deleted, or more.

Variants may be fragments of SEQ ID NO: 4. Such fragments retain pore-forming activity. Fragments may be at least 50, 100, 200 or 250 amino acids in length. A fragment preferably comprises the pore-forming domain of SEQ ID NO: 4. Fragments typically include residues 119, 121, 135. 113 and 139 of SEQ ID NO: 4.

One or more amino acids may be alternatively or additionally added to the polypeptides described above. An extension may be provided at the amino terminus or carboxy terminus of the amino acid sequence of SEQ ID NO: 4 or a variant or fragment thereof. The extension may be quite short, for example from 1 to 10 amino acids in length. Alternatively, the extension may be longer, for example up to 50 or 100 amino acids. A carrier protein may be fused to a pore or variant.

As discussed above, a variant of SEQ ID NO: 4 is a subunit that has an amino acid sequence which varies from that of SEQ ID NO: 4 and which retains its ability to form a pore. A variant typically contains the regions of SEQ ID NO: 4 that are responsible for pore formation. The pore forming ability of α-HL, which contains a β-barrel, is provided by β-strands in each subunit. A variant of SEQ ID NO: 4 typically comprises the regions in SEQ ID NO: 4 that form β-strands. The amino acids of SEQ ID NO: 4 that form β-strands are discussed above. One or more modifications can be made to the regions of SEQ ID NO: 4 that form β-strands as long as the resulting variant retains its ability to form a pore. Specific modifications that can be made to the β-strand regions of SEQ ID NO: 4 are discussed above.

A variant of SEQ ID NO: 4 preferably includes one or more modifications, such as substitutions, additions or deletions, within its α-helices and/or loop regions. Amino acids that form α-helices and loops are discussed above.

The variant may be modified to assist its identification or purification as discussed above.

Pores derived from α-HL can be made as discussed above with reference to pores derived from Msp.

In some embodiments, the transmembrane protein pore is chemically modified. The pore can be chemically modified in any way and at any site. The transmembrane protein pore is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus.

Suitable methods for carrying out such modifications are well-known in the art. The transmembrane protein pore may be chemically modified by the attachment of any molecule. For instance, the pore may be chemically modified by attachment of a dye or a fluorophore.

Any number of the monomers in the pore may be chemically modified. One or more, such as 2, 3, 4, 5, 6, 7, 8, 9 or 10, of the monomers is preferably chemically modified as discussed above.

The reactivity of cysteine residues may be enhanced by modification of the adjacent residues. For instance, the basic groups of flanking arginine, histidine or lysine residues will change the pKa of the cysteines thiol group to that of the more reactive S$^-$ group. The reactivity of cysteine residues may be protected by thiol protective groups such as dTNB. These may be reacted with one or more cysteine residues of the pore before a linker is attached.

The molecule (with which the pore is chemically modified) may be attached directly to the pore or attached via a linker as disclosed in International Application Nos. PCT/GB09/001,690 (published as WO 2010/004273), PCT/GB09/001,679 (published as WO 2010/004265) or PCT/GB10/000,133 (published as WO 2010/086603).

Any XPD helicase may be used in accordance with the invention. XPD helicases are also known as Rad3 helicases and the two terms can be used interchangeably.

The structures of XPD helicases are known in the art (Cell. 2008 May 30; 133(5):801-12. Structure of the DNA repair helicase XPD. Liu H, Rudolf J, Johnson K A, McMahon S A, Oke M, Carter L, McRobbie A M, Brown S E, Naismith J H, White M F). The XPD helicase typically comprises the amino acid motif X1-X2-X3-G-X4-X5-X6-E-G (hereinafter called XPD motif V; SEQ ID NO: 8). X1, X2, X5 and X6 are independently selected from any amino acid except D, E, K and R. X1, X2, X5 and X6 are independently selected from G, P, A, V, L, I, M, C, F, Y, W, H, Q, N, S and T. X1, X2, X5 and X6 are preferably not charged. X1, X2, X5 and X6 are preferably not H. X1 is more preferably V, L, I, S or Y. X5 is more preferably V, L, I, N or F. X6 is more preferably S or A. X3 and X4 may be any amino acid residue. X4 is preferably K, R or T.

The XPD helicase typically comprises the amino acid motif Q-Xa-Xb-G-R-Xc-Xd-R-(Xe)$_3$-Xf-(Xg)$_7$-D-Xh-R (hereinafter called XPD motif VI; SEQ ID NO: 9). Xa, Xe and Xg may be any amino acid residue. Xb, Xc and Xd are independently selected from any amino acid except D, E, K and R. Xb, Xc and Xd are typically independently selected from G, P, A, V, L, I, M, C, F, Y, W, H, Q, N, S and T. Xb, Xc and Xd are preferably not charged. Xb, Xc and Xd are preferably not H. Xb is more preferably V, A, L, I or M. Xc is more preferably V, A, L, I, M or C. Xd is more preferably I, H, L, F, M or V. Xf may be D or E. (Xg)$_7$ is $X_{g1}$, $X_{g2}$, $X_{g3}$, $X_{g4}$, $X_{g5}$, $X_{g6}$ and $X_{g7}$. $X_{g2}$ is preferably G, A, S or C. $X_{g5}$ is preferably F, V, L, I, M, A, W or Y. $X_{g6}$ is preferably L, F, Y, M, I or V. $X_{g7}$ is preferably A, C, V, L, I, M or S.

The XPD helicase preferably comprises XPD motifs V and VI. The most preferred XPD motifs V and VI are shown in Table 5 below.

The XPD helicase preferably further comprises an iron sulphide (FeS) core between two Walker A and B motifs (motifs I and II). An FeS core typically comprises an iron atom coordinated between the sulphide groups of cysteine residues. The FeS core is typically tetrahedral.

The XPD helicase is preferably one of the helicases shown in Table 4 below or a variant thereof.

TABLE 4

Preferred XPD helicases

| | | |
|---|---|---|
| 1 | YP 566221.1 | Rad3-related DNA helicases [*Methanococcoides burtonii* DSM |
| 2 | YP 003727831.1 | DEAD 2 domain-containing protein [*Methanohalobium* |
| 3 | YP 004617026.1 | DEAD 2 domain-containing protein [*Methanosalsum zhilinae* |
| 4 | YP 003541314.1 | DEAD/DEAH box helicase [*Methanohalophilus mahii* DSM |
| 5 | NP 633611.1 | DNA repair helicase [*Methanosarcina mazei* Go1] |
| 6 | NP 615308.1 | DNA helicase RepD [*Methanosarcina acetivorans* C2A] |
| 7 | YP 304917.1 | DNA helicase RepD [*Methanosarcina barkeri* str. *Fusaro*] |
| 8 | YP 686711.1 | putative ATP-dependent DNA-repair helicase [uncultured |
| 9 | YP 003355887.1 | DNA repair helicase [*Methanocella paludicola* SANAE] |
| 10 | ZP 08042768.1 | DEAD 2 domain protein [*Haladaptatus paucihalophilus* |
| 11 | YP 003401909.1 | DEAD 2 domain protein [*Haloterrigena turkmenica* DSM 5511] |
| 12 | YP 004035231.1 | DNA helicase, rad3 [*Halogeometricum borinquense* DSM |
| 13 | YP 003534113.1 | helicase [*Haloferax volcanii* DS2] >gb|ADE05091.1|helicase |
| 14 | YP 003176661.1 | DEAD 2 domain protein [*Halomicrobium mukohataei* DSM |
| 15 | YP 326312.1 | DNA repair helicase-like protein [*Natronomonas pharaonis* |
| 16 | YP 004595879.1 | DEAD 2 domain-containing protein [*Halopiger xanaduensis* |
| 17 | ZP 08967673.1 | DEAD 2 domain protein [*Natronobacterium gregoryi* SP2] |
| 18 | YP 003735388.1 | DEAD 2 domain-containing protein [*Halalkalicoccus jeotgali* |
| 19 | YP 003479905.1 | DEAD 2 domain-containing protein [*Natrialba magadii* ATCC |
| 20 | YP 003130325.1 | DEAD 2 domain protein [*Halorhabdus utahensis* DSM 12940] |
| 21 | YP 002567268.1 | DEAD 2 domain protein [*Halorubrum lacusprofundi* ATCC |
| 22 | ZP 08561264.1 | DEAD 2 domain protein [*Halorhabdus tiamatea* SARL4B] |
| 23 | YP 004794633.1 | helicase [*Haloarcula hispanica* ATCC 33960] >gb|AEM55645.1| |
| 24 | YP 137192.1 | helicase [*Haloarcula marismortui* ATCC 43049] |
| 25 | ZP 08963818.1 | helicase c2 [*Natrinema pellirubrum* DSM 15624] |
| 26 | NP 281042.1 | helicase [*Halobacterium* sp. NRC-1] >ref|YP 001690174.1| |
| 27 | YP 004808929.1 | DEAD 2 domain-containing protein [halophilic archaeon |
| 28 | CCC41858.1 | DNA repair helicase Rad3 [*Haloquadratum walsbyi* C23] |
| 29 | YP 659380.1 | DNA repair helicase-like protein [*Haloquadratum walsbyi* DSM |
| 30 | YP 686810.1 | putative ATP-dependent helicase [uncultured methanogenic |
| 31 | ZP 09027753.1 | Helicase-like, DEXD box c2 type [*Halobacterium* sp. DL1] |
| 32 | ZP 08042627.1 | helicase [*Haladaptatus paucihalophilus* DX253] |
| 33 | YP 002565485.1 | helicase c2 [*Halorubrum lacusprofundi* ATCC 49239] |
| 34 | YP 003737184.1 | helicase c2 [*Halalkalicoccus jeotgali* B3] >gb|ADJ15392.1|helicase |
| 35 | YP 003480051.1 | helicase c2 [*Natrialba magadii* ATCC 43099] >gb|ADD05489.1| |
| 36 | YP 004808332.1 | helicase c2 [*halophilic archaeon* DL31] >gb|AEN05959.1| |
| 37 | ZP 08967636.1 | helicase c2 [*Natronobacterium gregoryi* SP2] >gb|EHA70214.1| |
| 38 | ZP 09028751.1 | type III restriction protein res subunit [*Halobacterium* sp. DL1] |
| 39 | YP 326140.1 | DNA repair helicase [*Natronomonas pharaonis* DSM 2160] |
| 40 | YP 004595921.1 | helicase c2 [*Halopiger xanaduensis* SH-6] >gb|AEH36042.1| |
| 41 | ZP 08963989.1 | helicase c2 [*Natrinema pellirubrum* DSM 15624] |
| 42 | ZP 08560622.1 | helicase [*Halorhabdus tiamatea* SARL4B] >ref|ZP 08560903.1| |
| 43 | YP 003405301.1 | helicase c2 [*Haloterrigena turkmenica* DSM 5511] |
| 44 | ZP 08558438.1 | helicase c2 [*Halorhabdus tiamatea* SARL4B] >gb|EGM36622.1| |
| 45 | YP 003131362.1 | helicase c2 [*Halorhabdus utahensis* DSM 12940] |
| 46 | EHF09015.1 | DEAD 2 domain protein [*Methanolinea tarda* NOBI-1] |
| 47 | YP 001030540.1 | queuine tRNA-ribosyltransferase [*Methanocorpusculum* |
| 48 | YP 135387.1 | helicase [*Haloarcula marismortui* ATCC 43049] |
| 49 | YP 004795935.1 | helicase [*Haloarcula hispanica* ATCC 33960] >gb|AEM56947.1| |
| 50 | YP 003178787.1 | helicase c2 [*Halomicrobium mukohataei* DSM 12286] |
| 51 | YP 003895110.1 | DEAD 2 domain-containing protein [*Methanoplanus* |
| 52 | ABQ75766.1 | DNA repair helicase Rad3 [uncultured haloarchaeon] |
| 53 | YP 003535402.1 | helicase [*Haloferax volcanii* DS2] >gb|ADE04644.1|helicase |
| 54 | YP 502434.1 | helicase c2 [*Methanospirillum hungatei* JF-1] >gb|ABD40715.1| |
| 55 | CCC40051.1 | DNA repair helicase Rad3 [*Haloquadratum walsbyi* C23] |
| 56 | YP 657741.1 | DNA repair helicase Rad3 [*Haloquadratum walsbyi* DSM |
| 57 | YP 004424267.1 | DNA repair helicase rad3 [*Pyrococcus* sp. NA2] |
| 58 | NP 578662.1 | DNA repair helicase rad3, putative [*Pyrococcus furiosus* DSM |
| 59 | BAB59155.1 | DNA repair helicase [*Thermoplasma volcanium* GSS1] |
| 60 | NP 110532.1 | Rad3-related DNA helicase [*Thermoplasma volcanium* GSS1] |
| 61 | YP 004036893.1 | DNA helicase, rad3 [*Halogeometricum borinquense* DSM |
| 62 | CBH38285.1 | putative helicase [uncultured archaeon] |
| 63 | AAU82137.1 | conserved hypothetical protein [uncultured archaeon |
| 64 | YP 844078.1 | helicase c2 [*Methanosaeta thermophila* PT] >gb|ABK15438.1| |
| 65 | NP 127020.1 | DNA repair helicase rad3 [*Pyrococcus abyssi* GE5] |
| 66 | YP 001404278.1 | DEAD 2 domain-containing protein [*Candidatus* |
| 67 | NP 280229.1 | helicase [*Halobacterium* sp. NRC-1] >ref|YP 001689339.1| |
| 68 | YP 002994616.1 | ERCC2/XPD/Rad3-related DNA repair helicase [*Thermococcus* |
| 69 | NP 393536.1 | Rad3-related DNA helicase [*Thermoplasma acidophilum* DSM |
| 70 | YP 004071335.1 | DNA repair Rad3-like helicase [*Thermococcus barophilus* MP] |
| 71 | YP 002307425.1 | ERCC2/XPD/Rad3-related DNA repair helicase [*Thermococcus* |
| 72 | YP 002466730.1 | DEAD 2 domain protein [*Methanosphaerula palustris* E1-9c] |
| 73 | ZP 04876197.1 | DEAD 2 family [*Aciduliprofundum boonei* T469] |
| 74 | YP 004623247.1 | DNA repair helicase rad3 [*Pyrococcus yayanosii* CH1] |
| 75 | YP 002583205.1 | DNA repair helicase Rad3 [*Thermococcus* sp. AM4] |
| 76 | YP 004763640.1 | ERCC2/XPD/Rad3-related DNA repair helicase [*Thermococcus* |
| 77 | ZP 08857944.1 | hypothetical protein HMPREF9022 03601 [*Erysipelotrichaceae* |
| 78 | ZP 04875144.1 | DEAD 2 family [*Aciduliprofundum boonei* T469] |

TABLE 4-continued

Preferred XPD helicases

| # | Accession | Description |
|---|---|---|
| 79 | ZP 07832784.1 | DEAD2 domain protein [*Clostridium* sp. HGF2] |
| 80 | Q9HM14.1 | RecName: Full = ATP-dependent DNA helicase Ta0057 |
| 81 | XP 001736798.1 | regulator of telomere elongation helicase 1 rtel1 [*Entamoeba* |
| 82 | YP 004038234.1 | DEAD 2 domain-containing protein [*Halogeometricum*] |
| 83 | EET89549.1 | DEAD 2 domain protein [*Candidatus Micrarchaeum*] |
| 84 | NP 142644.1 | hypothetical protein PH0697 [*Pyrococcus horikoshii* OT3] |
| 85 | EGQ39936.1 | Rad3-related DNA helicase [*Candidatus Nanosalinarum* sp.] |
| 86 | NP 348298.1 | Rad3-related DNA helicase [*Clostridium acetobutylicum* ATCC |
| 87 | ZP 05426745.1 | helicase [*Enterococcus faecalis* T2] >gb|EET99653.1|helicase |
| 88 | EFU12338.1 | DEAD 2 protein [*Enterococcus faecalis* TX1341] |
| 89 | ZP 07559866.1 | DEAD 2 protein [*Enterococcus faecalis* TX0860] |
| 90 | ZP 02638747.1 | putative ATP-dependent helicase [*Clostridium perfringens* CPE |
| 91 | EGQ43484.1 | Rad3-related DNA helicase [*Candidatus Nanosalina* sp.] |
| 92 | YP 695853.1 | putative ATP-dependent helicase [*Clostridium perfringens*] |
| 93 | XP 651401.1 | DNA repair helicase [*Entamoeba histolytica* HM-1: IMSS] |
| 94 | YP 004094073.1 | helicase c2 [*Bacillus cellulosilyticus* DSM 2522] |
| 95 | ZP 02635303.1 | putative ATP-dependent helicase [*Clostridium perfringens* B str. |
| 96 | YP 002459406.1 | DEAD/DEAH box helicase [*Desulfitobacterium hafniense*] |
| 97 | ZP 02631448.1 | putative ATP-dependent helicase [*Clostridium perfringens* E str. |
| 98 | YP 183197.1 | ERCC2/XPD/Rad3-related DNA repair helicase [*Thermococcus*] |
| 99 | XP 003386532.1 | PREDICTED: TFIIH basal transcription factor complex helicase |
| 100 | YP 698539.1 | ATP-dependent helicase [*Clostridium perfringens* SM101] |
| 101 | ZP 06870390.1 | ATP-dependent helicase [*Fusobacterium nucleatum* subsp. |
| 102 | YP 003851460.1 | DEAD 2 domain-containing protein [*Thermoanaerobacterium*] |
| 103 | YP 001046704.1 | helicase c2 [*Methanoculleus marisnigri* JR1] >gb|ABN56722.1| |
| 104 | ZP 01860521.1 | probable helicase protein [*Bacillus* sp. SG-1] >gb|EDL64380.1| |
| 105 | YP 518026.1 | hypothetical protein DSY1793 [*Desulfitobacterium hafniense*] |
| 106 | NP 562113.1 | helicase protein [*Clostridium perfringens* str. 13] |
| 107 | ZP 02643466.1 | putative ATP-dependent helicase [*Clostridium perfringens*] |
| 108 | NP 603640.1 | ATP-dependent helicase DinG [*Fusobacterium nucleatum* subsp. |
| 109 | XP 003488158.1 | PREDICTED: Fanconi anemia group J protein-like [*Bombus*] |
| 110 | ZP 05562829.1 | helicase [*Enterococcus faecalis* DS5] >ref|ZP 05572349.1| |
| 111 | AEA93627.1 | DNA-directed DNA polymerase III epsilon subunit |
| 112 | ZP 07571029.1 | DEAD 2 protein [*Enterococcus faecalis* TX0411] |
| 113 | ZP 07550093.1 | DEAD 2 protein [*Enterococcus faecalis* TX4248] |
| 114 | ZP 07758962.1 | DEAD 2 protein [*Enterococcus faecalis* TX0470] |
| 115 | EFT88579.1 | DEAD 2 protein [*Enterococcus faecalis* TX2141] |
| 116 | ZP 05472340.1 | helicase [*Anaerococcus vaginalis* ATCC 51170] |
| 117 | ZP 06629187.1 | putative helicase [*Enterococcus faecalis* R712] |
| 118 | EFT95025.1 | Dead 2 protein [*Enterococcus faecalis* TX0012] |
| 119 | ZP 03982997.1 | DNA-directed DNA polymerase III epsilon subunit |
| 120 | ZP 05595984.1 | DEAD 2 family protein [*Enterococcus faecalis* T11] |
| 121 | ZP 05566414.1 | DEAD 2 [*Enterococcus faecalis* Merz96] >gb|EEU69371.1| |
| 122 | ZP 05592774.1 | helicase [*Enterococcus faecalis* AR01/DG] >gb|EEU87568.1| |
| 123 | EFU14918.1 | DEAD 2 protein [*Enterococcus faecalis* TX1342] |
| 124 | ZP 05599911.1 | helicase [*Enterococcus faecalis* X98] >gb|EEU94705.1|helicase |
| 125 | ZP 05569608.1 | DEAD 2 [*Enterococcus faecalis* HIP11704] >gb|EEU72565.1| |
| 126 | NP 814892.1 | helicase [*Enterococcus faecalis* V583] >gb|AAO80962.1| |
| 127 | ZP 05423702.1 | helicase [*Enterococcus faecalis* T1] >gb|EET96610.1|helicase |
| 128 | ZP 04439070.1 | DNA-directed DNA polymerase III epsilon subunit |
| 129 | ZP 05579939.1 | DNA repair helicase [*Enterococcus faecalis* Fly1] |
| 130 | ZP 05558182.1 | DEAD 2 protein [*Enterococcus faecalis* T8] >gb|EEU26309.1| |
| 131 | ZP 04971104.1 | ATP-dependent helicase [*Fusobacterium nucleatum* subsp. |
| 132 | ZP 05577237.1 | DNA repair helicase [*Enterococcus faecalis* E1Sol] |
| 133 | ZP 03948465.1 | DNA-directed DNA polymerase III epsilon subunit |
| 134 | ZP 05502750.1 | helicase [*Enterococcus faecalis* T3] >gb|EEU23116.1|helicase |
| 135 | ZP 04434884.1 | DNA-directed DNA polymerase III epsilon subunit |
| 136 | ZP 08170094.1 | DEAD2 domain protein [*Anaerococcus hydrogenalis* ACS-025- |
| 137 | EGG57994.1 | DEAD2 domain protein [*Enterococcus faecalis* TX1467] |
| 138 | EFT39574.1 | DEAD 2 protein [*Enterococcus faecalis* TX2137] |
| 139 | ZP 05580877.1 | DEAD 2 domain-containing protein [*Enterococcus faecalis* D6] |
| 140 | ZP 07761503.1 | DEAD 2 protein [*Enterococcus faecalis* TX0635] |
| 141 | ZP 05583934.1 | helicase [*Enterococcus faecalis* CH188] >gb|EEU84905.1| |
| 142 | ZP 07568518.1 | DEAD 2 protein [*Enterococcus faecalis* TX0109] |
| 143 | XP 001943653.1 | PREDICTED: TFIIH basal transcription factor complex helicase |
| 144 | XP 003397282.1 | PREDICTED: Fanconi anemia group J protein homolog |
| 145 | AAB62733.1 | RepD [*Dictyostelium discoideum*] |
| 146 | XP 647302.1 | transcription factor IIH component [*Dictyostelium discoideum*] |
| 147 | ZP 04666640.1 | DEAD 2 domain-containing protein [*Clostridiales bacterium*] |
| 148 | ZP 05475592.1 | helicase [*Enterococcus faecalis* ATCC 4200] >gb|EEU17449.1| |
| 149 | XP 002172261.1 | DNA repair helicase RAD3 [*Schizosaccharomyces japonicus*] |
| 150 | YP 002959163.1 | DNA repair helicase, ERCC2/XPD/rad3/TFIIH helicase beta |
| 151 | ZP 08958775.1 | hypothetical protein HAL1 05693 [*Halomonas* sp. HAL1] |
| 152 | ZP 07555075.1 | DEAD 2 protein [*Enterococcus faecalis* TX0855] |
| 153 | ZP 06600298.1 | ATP-dependent helicase [*Fusobacterium periodonticum* ATCC |
| 154 | ZP 07106135.1 | DEAD2 domain protein [*Enterococcus faecalis* TUSoD Ef11] |
| 155 | NP 593025.1 | transcription factor TFIIH complex subunit Rad15 |
| 156 | XP 001605333.2 | PREDICTED: TFIIH basal transcription factor complex helicase |

TABLE 4-continued

Preferred XPD helicases

| | | |
|---|---|---|
| 157 | CAA45870.1 | rhp3+ [*Schizosaccharomyces pombe*] |
| 158 | CAA43022.1 | rad15 [*Schizosaccharomyces pombe*] |
| 159 | EGG04750.1 | hypothetical protein MELLADRAFT 108080 [*Melampsora* |
| 160 | EEH20175.1 | TFIIH basal transcription factor complex helicase subunit |
| 161 | ZP 02430992.1 | hypothetical protein CLOSCI 01208 [*Clostridium scindens* |
| 162 | ZP 08601936.1 | hypothetical protein HMPREF0993 01313 [*Lachnospiraceae* |
| 163 | XP 780825.2 | PREDICTED: similar to TFIIH basal transcription factor |
| 164 | XP 003307004.1 | hypothetical protein PTT 20325 [*Pyrenophora teres* f. *teres* 0-1] |
| 165 | ADD93161.1 | hypothetical protein [uncultured archaeon MedDCM-OCT-S05- |
| 166 | EFW43568.1 | nucleotide excision repair protein [*Capsaspora owczarzaki* |
| 167 | ZP 03759096.1 | hypothetical protein CLOSTASPAR 03119 [*Clostridium* |
| 168 | YP 003246012.1 | DEAD 2 domain-containing protein [*Paenibacillus* sp. |
| 169 | AAA85822.1 | ERCC2/XPD [*Xiphophorus maculatus*] |
| 170 | XP 002796308.1 | DNA repair helicase RAD3 [*Paracoccidioides brasiliensis* Pb01] |
| 171 | EFT92378.1 | DEAD 2 protein [*Enterococcus faecalis* TX4244] |
| 172 | EGF80866.1 | hypothetical protein BATDEDRAFT 29908 [*Batrachochytrium* |
| 173 | ZP 07897118.1 | DEAD 2 domain protein [*Paenibacillus vortex* V453] |
| 174 | CBQ68748.1 | probable RAD3-DNA helicase/ATPase [*Sporisorium reilianum* |
| 175 | EGP86663.1 | hypothetical protein MYCGRDRAFT 43883 [*Mycosphaerella* |
| 176 | EGW30235.1 | DNA helicase component of transcription factor b [*Spathaspora* |
| 177 | ZP 03166460.1 | hypothetical protein RUMLAC 00106 [*Ruminococcus lactaris* |
| 178 | YP 003152744.1 | DEAD 2 domain-containing protein [*Anaerococcus prevotii* |
| 179 | ZP 06750962.1 | ATP-dependent helicase. DinG family [*Fusobacterium* sp. |
| 180 | ZP 07670993.1 | putative helicase [*Erysipelotrichaceae bacterium* 3 1 53] |
| 181 | ZP 04572193.1 | ATP-dependent helicase DinG [*Fusobacterium* sp. 4 1 13] |
| 182 | ZP 06673551.1 | DNA helicase [*Enterococcus faecium* E1039] >gb|EFF33221.1| |
| 183 | EFU18615.1 | DEAD 2 protein [*Enterococcus faecalis* TX1346] |
| 184 | EGG20082.1 | transcription factor IIH component [*Dictyostelium fasciculatum*] |
| 185 | YP 002944692.1 | DEAD 2 domain-containing protein [*Variovorax paradoxus* |
| 186 | EHA50547.1 | DNA repair helicase rad15 [*Magnaporthe oryzae* 70-15] |
| 187 | EEQ84204.1 | DNA repair helicase RAD3 [*Ajellomyces dermatitidis* ER-3] |
| 188 | CCE41018.1 | hypothetical protein CPAR2 300070 [*Candida parapsilosis*] |
| 189 | ZP 05550498.1 | ATP-dependent helicase [*Fusobacterium* sp. 3 1 36A2] |
| 190 | XP 003292674.1 | hypothetical protein DICPUDRAFT 50564 [*Dictyostelium* |
| 191 | YP 003821569.1 | helicase c2 [*Clostridium saccharolyticum* WM1] |
| 192 | XP 002550658.1 | DNA repair helicase RAD3 [*Candida tropicalis* MYA-3404] |
| 193 | ZP 08689728.1 | ATP-dependent helicase [*Fusobacterium* sp. 2 1 31] |
| 194 | XP 002499882.1 | predicted protein [*Micromonas* sp. RCC299] >gb|ACO61140.1] |
| 195 | ZP 06747464.1 | ATP-dependent helicase, DinG family [*Fusobacterium* sp. |
| 196 | CBK74961.1 | Rad3-related DNA helicases [*Butyrivibrio fibrisolvens* 16/4] |
| 197 | ABZ07948.1 | putative DEAD 2 [uncultured marine microorganism |
| 198 | EEH08589.1 | DNA repair helicase RAD3 [*Ajellomyces capsulatus* G186AR] |
| 199 | YP 003959319.1 | hypothetical protein ELI 1370 [*Eubacterium limosum* KIST612] |
| 200 | XP 001727494.1 | DNA repair helicase rad15 [*Aspergillus oryzae* RIB40] |
| 201 | NP 001133411.1 | TFIIH basal transcription factor complex helicase subunit |
| 202 | EGM49944.1 | DEAD2 domain protein [*Lactobacillus salivarius* GJ-24] |
| 203 | ADJ78619.1 | Superfamily II DNA and RNA helicase [*Lactobacillus salivarius* |
| 204 | ZP 04009603.1 | superfamily II DNA/RNA helicase [*Lactobacillus salivarius* |
| 205 | XP 003456443.1 | PREDICTED: TFIIH basal transcription factor complex helicase |
| 206 | ZP 05922403.1 | helicase [*Enterococcus faecium* TC 6] >ref|ZP 06446725.1] |
| 207 | ZP 00604560.1 | DEAD 2 [*Enterococcus faecium* DO] >ref|ZP 05657789.1] |
| 208 | ADY43014.1 | TFIIH basal transcription factor complex helicase XPD subunit, |
| 209 | ZP 06680717.1 | DNA helicase [*Enterococcus faecium* E1071] >gb|EFF19797.1] |
| 210 | XP 001210680.1 | DNA repair helicase RAD3 [*Aspergillus terreus* NIH2624] |
| 211 | ZP 05664394.1 | DEAD 2 helicase [*Enterococcus faecium* 1,231,501] |
| 212 | ZP 07872333.1 | helicase c2 domain-containing protein [*Listeria ivanovii* FSL F6- |
| 213 | XP 002375772.1 | TFIIH complex helicase Rad3, putative [*Aspergillus flavus* |
| 214 | XP 002995821.1 | hypothetical protein NCER 101193 [*Nosema ceranae* BRL01] |
| 215 | EGE80033.1 | DNA repair helicase RAD3 [*Ajellomyces dermatitidis* ATCC |
| 216 | XP 001930685.1 | TFIIH basal transcription factor complex helicase subunit |
| 217 | ZP 05678362.1 | DEAD 2 helicase [*Enterococcus faecium* Com15] |
| 218 | ZP 08193463.1 | helicase c2 [*Clostridium papyrosolvens* DSM 2782] |
| 219 | XP 002432433.1 | TFIIH basal transcription factor complex helicase subunit, |
| 220 | ZP 08278913.1 | DEAD2 domain protein [*Paenibacillus* sp. HGF5] |
| 221 | EFY84841.1 | DNA repair helicase RAD3 [*Metarhizium acridum* CQMa 102] |
| 222 | EFY99240.1 | DNA repair helicase RAD3 [*Metarhizium anisopliae* ARSEF |
| 223 | XP 001638817.1 | predicted protein [*Nematostella vectensis*] >gb|EDO46754.1] |
| 224 | ZP 08401953.1 | helicase c2 [*Rubrivivax benzoatilyticus* JA2] >gb|EGJ10286.1] |
| 225 | YP 004886930.1 | hypothetical protein TEH 14390 [*Tetragenococcus halophilus* |
| 226 | XP 001749760.1 | hypothetical protein [*Monosiga brevicollis* MX1] |
| 227 | YP 535245.1 | superfamily II DNA/RNA helicase [*Lactobacillus salivarius* |
| 228 | XP 002126055.1 | PREDICTED: similar to ERCC2/XPD gene product [*Ciona* |
| 229 | EGC43631.1 | DNA repair helicase RAD3 [*Ajellomyces capsulatus* H88] |
| 230 | ZP 07207225.1 | DEAD2 domain protein [*Lactobacillus salivarius* ACS-116-V- |
| 231 | EEH44570.1 | DNA repair helicase RAD3 [*Paracoccidioides brasiliensis* Pb18] |
| 232 | ZP 03981356.1 | DNA-directed DNA polymerase III epsilon subunit |
| 233 | EFX74423.1 | hypothetical protein DAPPUDRAFT 324413 [*Daphnia pulex*] |
| 234 | ZP 06696925.1 | DNA helicase [*Enterococcus faecium* E1679] >gb|EFF27693.1] |

TABLE 4-continued

Preferred XPD helicases

| | | |
|---|---|---|
| 235 | YP 608233.1 | hypothetical protein PSEEN2644 [*Pseudomonas entomophila* |
| 236 | ZP 08007354.1 | hypothetical protein HMPREF1013 03969 [*Bacillus* sp. |
| 237 | CBF88902.1 | TPA: 5' to 3' DNA helicase (Eurofung) [*Aspergillus nidulans* |
| 238 | ZP 03952877.1 | DNA-directed DNA polymerase III epsilon subunit |
| 239 | EGU74151.1 | hypothetical protein FOXB 15338 [*Fusarium oxysporum* |
| 240 | EER42275.1 | DNA repair helicase RAD3 [*Ajellomyces capsulatus* H143] |
| 241 | ZP 06682941.1 | DNA helicase [*Enterococcus faecium* E980] >gb\|EFF37253.1\| |
| 242 | XP 001799767.1 | hypothetical protein SNOG 09475 [*Phaeosphaeria nodorum* |
| 243 | ZP 06623685.1 | DEAD2 domain protein [*Enterococcus faecium* PC4.1] |
| 244 | XP 002850254.1 | DNA repair helicase RAD3 [*Arthroderma otae* CBS 113480] |
| 245 | ZP 03939707.1 | DNA-directed DNA polymerase III epsilon subunit |
| 246 | ZP 03942652.1 | DNA-directed DNA polymerase III epsilon subunit |
| 247 | ZP 05667230.1 | DEAD 2 helicase [*Enterococcus faecium* 1,141,733] |
| 248 | ZP 08142092.1 | DEAD 2 domain-containing protein [*Pseudomonas* sp. TJI-51] |
| 249 | EGL98319.1 | DinG family ATP-dependent helicase [*Lactobacillus salivarius* |
| 250 | EGX45813.1 | hypothetical protein AOL s00117g18 [*Arthrobotrys oligospora* |
| 251 | YP 001374582.1 | bifunctional ATP-dependent DNA helicase/DNA polymerase III |
| 252 | XP 384471.1 | hypothetical protein FG04295.1 [*Gibberella zeae* PH-1] |
| 253 | XP 002610234.1 | hypothetical protein BRAFLDRAFT 286830 [*Branchiostoma* |
| 254 | ZP 05103122.1 | hypothetical protein MDMS009 258 [*Methylophaga* |
| 255 | XP 002177848.1 | xeroderma pigmentosum group D complementing protein |
| 256 | YP 901517.1 | DEAD 2 domain-containing protein [*Pelobacter propionicus* |
| 257 | YP 004646156.1 | Rtel-1 [*Paenibacillus mucilaginosus* KNP414] >gb\|AEI46286.1] |
| 258 | EHE97994.1 | hypothetical protein HMPREF9469 03327 [*Clostridium* |
| 259 | ZP 07913491.1 | ATP-dependent helicase DinG [*Fusobacterium gonidiaformans* |
| 260 | XP 001264365.1 | TFIIH complex helicase Rad3, putative [*Neosartorya fischeri* |
| 261 | CBK81746.1 | Rad3-related DNA helicases [*Coprococcus catus* GD/7] |
| 262 | NP 001104820.1 | FancJ-like protein [*Bombyx mori*] >dbj\|BAF94023.1\|FancJ-like |
| 263 | EFN69563.1 | TFIIH basal transcription factor complex helicase subunit |
| 264 | EGX89191.1 | DNA repair helicase RAD3 [*Cordyceps militaris* CM01] |
| 265 | YP 003463379.1 | hypothetical protein lse 0136 [*Listeria seeligeri* serovar 1/2b str. |
| 266 | ZP 04851424.1 | DEAD 2 domain-containing protein [*Paenibacillus* sp. oral |
| 267 | ZP 06525127.1 | ATP-dependent helicase DinG [*Fusobacterium* sp. D11] |
| 268 | ZP 08598770.1 | ATP-dependent helicase, DinG family [*Fusobacterium* sp. |
| 269 | YP 004155261.1 | helicase c2 [*Variovorax paradoxus* EPS] >gb\|ADU37150.1\| |
| 270 | CBX95892.1 | similar to TFIIH basal transcription factor complex helicase |
| 271 | EFQ33459.1 | DNA repair helicase [*Glomerella graminicola* M1.001] |
| 272 | ZP 07775478.1 | DEAD 2 [*Pseudomonas fluorescens* WH6] >gb\|EFQ63207.1] |
| 273 | ZP 05814223.1 | ATP-dependent helicase [*Fusobacterium* sp. 3 1 33] |
| 274 | ADD93162.1 | hypothetical protein [uncultured archaeon MedDCM-OCT-S05- |
| 275 | YP 004383205.1 | hypothetical protein MCON 0548 [*Methanosaeta concilii* GP6] |
| 276 | ZP 08687376.1 | ATP-dependent helicase DinG [*Fusobacterium mortiferum* |
| 277 | XP 752761.1 | TFIIH complex helicase Rad3 [*Aspergillus fumigatus* Af293] |
| 278 | YP 004701945.1 | DEAD 2 domain-containing protein [*Pseudomonas putida* S16] |
| 279 | XP 505677.1 | YALI0F20746p [*Yarrowia lipolytica*] >emb\|CAG78486.1\| |
| 280 | YP 004399302.1 | DEAD 2 domain-containing protein [*Lactobacillus buchneri* |
| 281 | YP 003278262.1 | hypothetical protein CtCNB1 2220 [*Comamonas testosteroni* |
| 282 | XP 003464723.1 | PREDICTED: TFIIH basal transcription factor complex helicase |
| 283 | XP 003048472.1 | predicted protein [*Nectria haematococca* mpVI 77-13-4] |
| 284 | XP 760298.1 | hypothetical protein UM04151.1 [*Ustilago maydis* 521] |
| 285 | YP 004840690.1 | hypothetical protein LSA 03010 [*Lactobacillus sanfranciscensis* |
| 286 | YP 002872713.1 | hypothetical protein PFLU3138 [*Pseudomonas fluorescens* |
| 287 | YP 004853959.1 | putative ATP dependent helicase [*Listeria ivanovii* subsp. |
| 288 | XP 001324631.1 | helicase [*Trichomonas vaginalis* G3] >gb\|EAY12408.1\| |
| 289 | ZP 08581874.1 | hypothetical protein HMPREF0404 01165 [*Fusobacterium* sp. |
| 290 | EFS01538.1 | helicase c2 domain-containing protein [*Listeria seeligeri* FSL |
| 291 | XP 001189997.1 | PREDICTED: similar to TFIIH basal transcription factor |
| 292 | XP 360589.2 | hypothetical protein MGG 03132 [*Magnaporthe oryzae* 70-15] |
| 293 | EGR44274.1 | DNA excision repair helicase [*Trichoderma reesei* QM6a] |
| 294 | XP 002115878.1 | hypothetical protein TRIADDRAFT 30066 [*Trichoplax* |
| 295 | YP 002140828.1 | DNA helicase, DEAD 2 domain-containing protein [*Geobacter* |
| 296 | CBK93524.1 | DEAD 2 [*Eubacterium rectale* M104/1] |
| 297 | CBK90099.1 | DEAD 2 [*Eubacterium rectale* DSM 17629] |
| 298 | ZP 04574821.1 | ATP-dependent helicase DinG [*Fusobacterium* sp. 7 1] |
| 299 | XP 001500524.3 | PREDICTED: LOW QUALITY PROTEIN: TFIIH basal |
| 300 | EFR92206.1 | helicase c2 domain-containing protein [*Listeria innocua* FSL S4- |
| 301 | NP 967260.1 | ATP dependent helicase [*Bdellovibrio bacteriovorus* HD100] |
| 302 | ZP 06645172.1 | putative helicase [*Erysipelotrichaceae bacterium* 5 2 54FAA] |
| 303 | YP 002937404.1 | putative ATP-dependent DNA-repair helicase [*Eubacterium* |
| 304 | AEO61831.1 | hypothetical protein MYCTH 104059 [*Myceliophthora* |
| 305 | XP 002723661.1 | PREDICTED: excision repair cross-complementing rodent |
| 306 | ZP 07928170.1 | helicase c2 [*Fusobacterium ulcerans* ATCC 49185] |
| 307 | EFS04602.1 | helicase c2 domain-containing protein [*Listeria seeligeri* FSL |
| 308 | ZP 05792445.1 | putative helicase [*Butyrivibrio crossotus* DSM 2876] |
| 309 | XP 002829448.1 | PREDICTED: LOW QUALITY PROTEIN: TFIIH basal |
| 310 | ZP 02358461.1 | DNA repair helicase [*Burkholderia oklahomensis* EO147] |
| 311 | AAB58296.1 | DNA helicase [*Mus musculus*] |
| 312 | XP 003245432.1 | PREDICTED: Fanconi anemia group J protein homolog isoform |

TABLE 4-continued

Preferred XPD helicases

| | | |
|---|---|---|
| 313 | XP 001943091.2 | PREDICTED: Fanconi anemia group J protein homolog isoform |
| 314 | YP 004232710.1 | DEAD 2 domain-containing protein [*Acidovorax avenae* subsp. |
| 315 | EGY20402.1 | DNA repair helicase RAD3 [*Verticillium dahliae* VdLs.17] |
| 316 | ZP 08812184.1 | DEAD 2 family protein [*Desulfosporosinus* sp. OT] |
| 317 | BAJ21097.1 | excision repair cross-complementing rodent repair deficiency, |
| 318 | BAE26794.1 | unnamed protein product [*Mus musculus*] |
| 319 | ZP 08130487.1 | putative helicase [*Clostridium* sp. D5] >gb|EGB92074.1| |
| 320 | XP 868818.1 | hypothetical protein AN9436.2 [*Aspergillus nidulans* FGSC A4] |
| 321 | XP 001656074.1 | DNA repair helicase rad3/xp-d [*Aedes aegypti*] |
| 322 | ZP 07045589.1 | DeaD2 [*Comamonas testosteroni* S44] >gb|EF160820.1|DeaD2 |
| 323 | NP 031975.2 | TFIIH basal transcription factor complex helicase XPD subunit |
| 324 | YP 001353393.1 | Rad3-related DNA helicases [*Janthinobacterium* sp. Marseille] |
| 325 | NP 001166280.1 | excision repair cross-complementing rodent repair deficiency, |
| 326 | AAH34517.1 | Ercc2 protein [*Mus musculus*] |
| 327 | NP 001231320.1 | TFIIH basal transcription factor complex helicase XPD subunit |
| 328 | XP 002561536.1 | Pc16g12370 [*Penicillium chrysogenum* Wisconsin 54-1255] |
| 329 | AEO71602.1 | hypothetical protein THITE 2124189 [*Thielavia terrestris* |
| 330 | YP 968571.1 | helicase c2 [*Acidovorax citrulli* AAC00-1] >gb|ABM30797.1| |
| 331 | XP 001548663.1 | conserved hypothetical protein [*Botryotinia fuckeliana* B05.10] |
| 332 | YP 004752764.1 | DinG family ATP-dependent helicase [*Collimonas fungivorans* |
| 333 | CCD46916.1 | similar to DNA repair helicase RAD3 [*Botryotinia fuckeliana*] |
| 334 | XP 001392821.1 | DNA repair helicase rad15 [*Aspergillus niger* CBS 513.88] |
| 335 | ZP 02466136.1 | putative ATP-dependent helicase [*Burkholderia thailandensis* |
| 336 | YP 004230200.1 | helicase c2 [*Burkholderia* sp. CCGE1001] >gb|ADX57140.1| |
| 337 | YP 002538024.1 | DEAD/DEAH box helicase [*Geobacter* sp. FRC-32] |
| 338 | EGJ23664.1 | Helicase c2 domain protein [*Listeria monocytogenes* str. Scott |
| 339 | ZP 02365524.1 | DNA repair helicase [*Burkholderia oklahomensis* C6786] |
| 340 | ZP 08637589.1 | hypothetical protein GME 12875 [*Halomonas* sp. TD01] |
| 341 | YP 012782.1 | hypothetical protein LMOf2365 0172 [*Listeria monocytogenes* |
| 342 | YP 003967478.1 | helicase c2 [*Ilyobacter polytropus* DSM 2926] |
| 343 | ZP 05230929.1 | conserved hypothetical protein [*Listeria monocytogenes* FSL J1- |
| 344 | XP 311900.4 | AGAP002988-PA [*Anopheles gambiae*str. PEST] |
| 345 | YP 848334.1 | helicase c2 domain-containing protein [*Listeria welshimeri* |
| 346 | EGG19835.1 | DEAD/DEAH box helicase [*Dictyostelium fasciculatum*] |
| 347 | EFD93152.1 | DEAD 2 domain protein [*Candidatus Parvarchaeum* |
| 348 | EFD92202.1 | DEAD 2 domain protein [*Candidatus Parvarchaeum* |
| 349 | XP 003007283.1 | DNA repair helicase RAD3 [*Verticillium albo-atrum* VaMs.102] |
| 350 | ZP 07896115.1 | DNA-directed DNA polymerase III epsilon subunit |
| 351 | ZP 02078033.1 | hypothetical protein EUBDOL 01841 [*Eubacterium dolichum* |
| 352 | XP 003082439.1 | DNA repair/transcription factor protein (ISS) [*Ostreococcus* |
| 353 | ZP 06555278.1 | conserved hypothetical protein [*Listeria monocytogenes* FSL J2- |
| 354 | YP 002756898.1 | ATP dependent helicase [*Listeria monocytogenes* serotype 4b |
| 355 | ZP 00230627.1 | conserved hypothetical protein [*Listeria monocytogenes* str. 4b |
| 356 | ZP 07707600.1 | DEAD 2 domain protein [*Bacillus* sp. m3-13] |
| 357 | ZP 02376616.1 | helicase c2 [*Burkholderia ubonensis* Bu] |
| 358 | YP 003305885.1 | helicase c2 [*Streptobacillus moniliformis* DSM 12112] |
| 359 | XP 001539110.1 | DNA repair helicase RAD3 [*Ajellomyces capsulatus* NAm1] |
| 360 | NP 469540.1 | hypothetical protein lin0195 [*Listeria innocua* Clip11262] |
| 361 | ZP 03777358.1 | hypothetical protein CLOHYLEM 04410 [*Clostridium* |
| 362 | ZP 02501541.1 | hypothetical protein Bpse112 28444 [*Burkholderia* |
| 363 | EGD01053.1 | helicase c2 [*Burkholderia* sp. TJI49] |
| 364 | YP 001513884.1 | DEAD 2 domain-containing protein [*Alkaliphilus oremlandii* |
| 365 | YP 004029082.1 | DNA REPAIR HELICASE (RAD3/RAD15/XPD FAMILY) |
| 366 | EFR95270.1 | helicase c2 domain-containing protein [*Listeria innocua* FSL J1- |
| 367 | AAM45142.1 | excision repair cross-complementing rodent repair deficiency, |
| 368 | BAB23443.1 | unnamed protein product [*Mus musculus*] |
| 369 | ZP 02384949.1 | DNA repair helicase [*Burkholderia thailandensis* Bt4] |
| 370 | AAI10524.1 | Excision repair cross-complementing rodent repair deficiency, |
| 371 | NP 000391.1 | TFIIH basal transcription factor complex helicase XPD subunit |
| 372 | NP 001233519.1 | TFIIH basal transcription factor complex helicase subunit [*Pan* |
| 373 | ZP 02414937.1 | Uvs006 [*Burkholderia pseudomallei* 14] |
| 374 | CAA36463.1 | ercc2 gene product [*Homo sapiens*] |
| 375 | YP 002908815.1 | putative ATP-dependent helicase *Burkholderia glumae* BGR1] |
| 376 | ZP 03462972.1 | hypothetical protein BACPEC 02058 [[*Bacteroides*] |
| 377 | AEO05170.1 | hypothetical protein LMRG 02402 [*Listeria monocytogenes* |
| 378 | ZP 00234550.1 | conserved hypothetical protein [*Listeria monocytogenes* str. 1/2a |
| 379 | NP 463690.1 | hypothetical protein lmo0157 [*Listeria monocytogenes* EGD-e] |
| 380 | YP 001321959.1 | DEAD 2 domain-containing protein [*Alkaliphilus* |
| 381 | ZP 08090025.1 | hypothetical protein HMPREF9474 01776 [*Clostridium* |
| 382 | CBL13167.1 | DEAD 2 [*Roseburia intestinalis* XB6B4] |
| 383 | ZP 02206869.1 | hypothetical protein COPEUT 01661 [*Coprococcus eutactus* |
| 384 | XP 003510809.1 | PREDICTED: Fanconi anemia group J protein homolog |
| 385 | EGS23598.1 | hypothetical protein CTHT 0002930 [*Chaetomium* |
| 386 | XP 970844.1 | PREDICTED: similar to *Xeroderma pigmentosum* D CG9433- |
| 387 | NP 001096787.1 | TFIIH basal transcription factor complex helicase XPD subunit |
| 388 | EFX06354.1 | tfiih complex helicase [*Grosmannia clavigera* kw1407] |
| 389 | ZP 05591145.1 | DNA repair helicase [*Burkholderia thailandensis* E264] |
| 390 | ABM06129.1 | excision repair cross-complementing rodent repair deficiency, |

TABLE 4-continued

Preferred XPD helicases

| | | |
|---|---|---|
| 391 | YP 001075221.1 | putative ATP-dependent helicase [*Burkholderia pseudomallei* |
| 392 | ZP 08274812.1 | DinG family ATP-dependent helicase [*Oxalobacteraceae* |
| 393 | YP 439745.1 | DNA repair helicase [*Burkholderia thailandensis* E264] |
| 394 | ZP 02406424.1 | hypothetical protein BpseD 29478 [*Burkholderia pseudomallei* |
| 395 | ZP 01893211.1 | DEAD 2 [*Marinobacter algicola* DG893] >gb\|EDM48600.1\| |
| 396 | YP 337604.1 | Uvs006 [*Burkholderia pseudomallei* 1710b] >gb\|ABA53062.1\| |
| 397 | ZP 01739164.1 | hypothetical protein MELB17 23815 [*Marinobacter* sp. ELB17] |
| 398 | YP 110868.1 | hypothetical protein BPSS0856 [*Burkholderia pseudomallei* |
| 399 | CBL41994.1 | Rad3-related DNA helicases [butyrate-producing bacterium |
| 400 | ZP 02459185.1 | hypothetical protein Bpseu9 28802 [*Burkholderia pseudomallei* |
| 401 | YP 001062257.1 | putative ATP-dependent helicase [*Burkholderia pseudomallei* |
| 402 | ZP 02451021.1 | hypothetical protein Bpseu9 29690 [*Burkholderia pseudomallei* |
| 403 | ZP 02493334.1 | hypothetical protein BpseN 28103 [*Burkholderia pseudomallei* |
| 404 | NP 497182.2 | hypothetical protein Y50D7A.2 [*Caenorhabditis elegans*] |
| 405 | XP 002640826.1 | Hypothetical protein CBG15713 [*Caenorhabditis briggsae*] |
| 406 | ZP 06114232.1 | putative helicase [*Clostridium hathewavi* DSM 13479] |
| 407 | YP 002351431.1 | helicase c2 domain protein [*Listeria monocytogenes* HCC23] |
| 408 | YP 003898973.1 | hypothetical protein HELO 3904 [*Halomonas elongata* DSM |
| 409 | ZP 03450263.1 | putative ATP-dependent helicase [*Burkholderia pseudomallei* |
| 410 | ZP 02474695.1 | hypothetical protein BpseB 28268 [*Burkholderia pseudomallei* |
| 411 | BAF62336.1 | DNA-repair protein complementing XP-D cells [*Sus scrofa*] |
| 412 | ZP 04588908.1 | DEAD 2 protein [*Pseudomonas syringae* pv. *oryzae* str. 1 6] |
| 413 | EGH68459.1 | hypothetical protein PSYAC 26881 [*Pseudomonas syringae* pv. |
| 414 | ZP 03569477.1 | helicase c2 [*Burkholderia multivorans* CGD2M] |
| 415 | ZP 08477214.1 | Rad3-related DNA helicase [*Lactobacillus coryniformis* subsp. |
| 416 | ZP 03543327.1 | DEAD 2 domain protein [*Comamonas testosteroni* KF-1] |
| 417 | ZP 08976894.1 | DEAD 2 domain protein [*Desulfitobacterium metallireducens* |
| 418 | ZP 05232273.1 | conserved hypothetical protein [*Listeria monocytogenes* FSL |
| 419 | ZP 04744708.1 | putative ATP-dependent helicase [*Roseburia intestinalis* L1-82] |
| 420 | YP 001584206.1 | helicase c2 [*Burkholderia multivorans* ATCC 17616] |
| 421 | EHF07121.1 | hypothetical protein HMPREF1020 01003 [*Clostridium* sp. |
| 422 | YP 001948666.1 | putative ATP-dependent DNA helicase [*Burkholderia* |
| 423 | CAF32100.1 | DNA repair helicase, putative [*Aspergillus fumigatus*] |
| 424 | EHB09904.1 | TFIIH basal transcription factor complex helicase subunit, |
| 425 | ZP 09000595.1 | helicase c2 [*Paenibacillus lactis* 154] >gb\|EHB65769.1\|helicase |
| 426 | ZP 02881609.1 | DEAD 2 domain protein [*Burkholderia graminis* C4D1M] |
| 427 | XP 003341121.1 | PREDICTED: LOW QUALITY PROTEIN: TFIIH basal |
| 428 | ZP 08574707.1 | DNA helicase (putative) [*Lactobacillus coryniformis* subsp. |
| 429 | ZP 03583039.1 | helicase c2 [*Burkholderia multivorans* CGD1] >gb\|EEE03212.1\| |
| 430 | YP 002234127.1 | hypothetical protein BCAM1516A [*Burkholderia cenocepacia* |
| 431 | NP 784122.1 | DNA helicase (putative) [*Lactobacillus plantarum* WCFS1] |
| 432 | YP 372388.1 | Rad3-related DNA helicases-like [*Burkholderia* sp. 383] |
| 433 | XP 002025881.1 | GL10160 [*Drosophila persimilis*] >ref\|XP 002138963.1\| |
| 434 | YP 003607521.1 | helicase c2 [*Burkholderia* sp. CCGE1002] >gb\|ADG18010.1\| |
| 435 | ZP 08981155.1 | DEAD 2 domain protein [*Desulfosporosinus meridiei* DSM |
| 436 | XP 001910036.1 | hypothetical protein [*Podospora anserina* S mat+] |
| 437 | CBY20154.1 | unnamed protein product [*Oikopleura dioica*] |
| 438 | YP 001557350.1 | DEAD 2 domain-containing protein [*Clostridium* |
| 439 | EHB06437.1 | Fanconi anemia group J protein [*Heterocephalus glaber*] |
| 440 | AAS21351.1 | helicase-like protein NHL-like protein [*Oikopleura dioica*] |
| 441 | YP 001117339.1 | helicase c2 [*Burkholderia vietnamiensis* G4] >gb\|ABO57874.1\| |
| 442 | ZP 06248030.1 | DEAD 2 domain protein [*Clostridium thermocellum* JW20] |
| 443 | ZP 03626657.1 | DEAD 2 domain protein [bacterium Ellin514] |
| 444 | EGC82354.1 | DEAD2 domain protein [*Anaerococcus prevotii* ACS-065-V- |
| 445 | YP 001669171.1 | DEAD 2 domain-containing protein [*Pseudomonas putida* GB- |
| 446 | YP 001779577.1 | helicase c2 [*Burkholderia cenocepacia* MC0-3] |
| 447 | EGX97283.1 | superfamily II DNA/RNA helicase [*Lactobacillus ruminis* |
| 448 | YP 001036721.1 | DEAD 2 [*Clostridium thermocellum* ATCC 27405] |
| 449 | EDM05558.1 | BRCA1 interacting protein C-terminal helicase 1 (predicted) |
| 450 | ZP 08564414.1 | superfamily II DNA/RNA helicase [*Lactobacillus ruminis* |
| 451 | YP 338478.1 | DNA repair helicase, truncation [*Burkholderia mallei* ATCC |
| 452 | ZP 05429973.1 | DEAD 2 domain protein [*Clostridium thermocellum* DSM |
| 453 | ZP 02908774.1 | helicase c2 [*Burkholderia ambifaria* MEX-5] >gb\|EDT40109.1\| |
| 454 | YP 003074789.1 | hypothetical protein TERTU 3456 [*Teredinibacter turnerae* |
| 455 | CBL10637.1 | DEAD 2 [*Roseburia intestinalis* M50/1] |
| 456 | ZP 08080348.1 | superfamily II DNA/RNA helicase [*Lactobacillus ruminis* |
| 457 | ZP 05714130.1 | helicase, putative [*Enterococcus faecium* DO] |
| 458 | YP 002505020.1 | DEAD 2 domain-containing protein [*Clostridium* |
| 459 | XP 002762284.1 | PREDICTED: TFIIH basal transcription factor complex |
| 460 | ZP 07869402.1 | helicase c2 domain-containing protein [*Listeria marthii* FSL S4- |
| 461 | YP 004394741.1 | hypothetical protein CbC4 0061 [*Clostridium botulinum* |
| 462 | YP 004681432.1 | Rad3-like DNA helicase [*Cupriavidus necator* N-1] |
| 463 | ZP 00442058.1 | putative ATP-dependent helicase [*Burkholderia mallei* GB8 |
| 464 | EHA18240.1 | DNA repair helicase, subunit of TFIIH [*Aspergillus niger* |
| 465 | EGT47910.1 | hypothetical protein CAEBREN 01520 [*Caenorhabditis* |
| 466 | ZP 03929588.1 | DNA-directed DNA polymerase III epsilon subunit |
| 467 | YP 001889149.1 | DEAD 2 domain-containing protein [*Burkholderia* |
| 468 | ZP 04156392.1 | DnaO family exonuclease/DinG family helicase [*Bacillus* |

TABLE 4-continued

Preferred XPD helicases

| | | |
|---|---|---|
| 469 | YP 003050181.1 | helicase c2 [*Methylovorus glucosetrophus* SIP3-4] |
| 470 | XP 002063431.1 | GK21904 [*Drosophila willistoni*] >gb|EDW74417.1|GK21904 |
| 471 | YP 235981.1 | DEAD 2 [*Pseudomonas syringae* pv. *syringae* B728a] |
| 472 | ZP 07004902.1 | ATP-dependent helicase [*Pseudomonas savastanoi* pv. |
| 473 | ZP 02371055.1 | DNA repair helicase [*Burkholderia thailandensis* TXDOH] |
| 474 | XP 002006040.1 | GI20811 [*Drosophila mojavensis*] >gb|EDW09975.1|GI20811 |
| 475 | ADI95426.1 | DEAD-2 domain-containing protein [*Pseudomonas putida*] |
| 476 | NP 744983.1 | DEAD 2 domain-containing protein [*Pseudomonas putida*] |
| 477 | ADR60507.1 | DEAD 2 domain protein [*Pseudomonas putida* BIRD-1] |
| 478 | ZP 06493673.1 | DEAD 2 [*Pseudomonas syringae* pv. *syringae* FF5] |
| 479 | YP 001311945.1 | DEAD 2 domain-containing protein [*Clostridium beijerinckii* |
| 480 | ADP99485.1 | Rad3-related DNA helicase [*Marinobacter adhaerens* HP15] |
| 481 | YP 001268166.1 | DEAD 2 domain-containing protein [*Pseudomonas putida* F1] |
| 482 | YP 003923571.1 | DNA helicase ( ) [*Lactobacillus plantarum* subsp. *plantarum* ST- |
| 483 | XP 340870.3 | PREDICTED: BRCA1 interacting protein C-terminal helicase 1 |
| 484 | YP 004619190.1 | ATP-dependent helicase-like protein [*Ramlibacter tataouinensis* |
| 485 | ZP 04947353.1 | Rad3-related DNA helicase [*Burkholderia dolosa* AUO158] |
| 486 | YP 623840.1 | helicase c2 [*Burkholderia cenocepacia* AU 1054] |
| 487 | YP 877033.1 | DNA repair helicase. truncation [*Clostridium novvi* NT] |
| 488 | ZP 02083792.1 | hypothetical protein CLOBOL 01315 [*Clostridium bolteae* |
| 489 | ZP 03212705.1 | Rad3-related DNA helicase [*Lactobacillus rhamnosus* HN001] |
| 490 | ZP 04941727.1 | Rad3-related DNA helicase [*Burkholderia cenocepacia* PC184] |
| 491 | ZP 02889716.1 | helicase c2 [*Burkholderia ambifaria* IOP40-10] |
| 492 | YP 775689.1 | helicase c2 [*Burkholderia ambifaria* AMMD] >gb|ABI89355.1| |
| 493 | ZP 04150622.1 | DnaQ family exonuclease/DinG family helicase [*Bacillus* |
| 494 | XP 001653621.1 | regulator of telomere elongation helicase 1 rtel1 [*Aedes aegypti*] |
| 495 | YP 001230873.1 | DEAD 2 domain-containing protein [*Geobacter uraniireducens* |
| 496 | YP 840785.1 | Rad3-related DNA helicase [*Ralstonia eutropha* H16] |
| 497 | ZP 07324798.1 | DEAD 2 domain protein [*Acetivibrio cellulolvticus* CD2] |
| 498 | ZP 05132613.1 | DEAD 2 domain-containing protein [*Clostridium* sp. |
| 499 | ZP 05347278.1 | putative helicase [*Bryantella formatexigens* DSM 14469] |
| 500 | ZP 08980710.1 | Exonuclease RNase T and DNA polymerase III |

The XPD helicase is more preferably one of the helicases shown in Table 5 below or a variant thereof. The XPD helicase more preferably comprises the sequence of one of the helicases shown in Table 5, i.e. one of SEQ ID NOs: 10, 13, 16, 18, 20, 22, 25, 28, 31, 33, 35, 38, 41, 43, 44, 46, 49, 52, 55, 57, 59, 61 and 62, or a variant thereof.

TABLE 5

More preferred XPD helicases and most preferred XPD motifs V and VI

| SEQ ID NO | Name | Strain | Accession No. | % Identity to XPD Mbu | Motif V (SEQ ID NO) | Motif VI (SEQ ID NO) |
|---|---|---|---|---|---|---|
| 10 | XPD Mbu | *Methanococcoides burtonii* | YP_566221.1 GI:91773529 | — | YLWGT LSEG (11) | QAMGR VVRSP TDYGA RILLDG R (12) |
| 13 | XPD Hla | *Halorubrum lacusprofundi* | YP_002567268.1 GI:222481031 | 42 | SLWGT LAEG (14) | QAIGR VVRGP DDFGV RILADR R (15) |
| 16 | XPD Mac | *Methanosarcina acetivorans* C2A | NP_615308.1 GI:20089233 | 55 | YLWGT LSEG (11) | QAMGR VVRSP GDFGV RILLDA R (17) |
| 18 | XPD Mzh | *Methanosalsum zhilinae* | YP_004617026.1 GI:336477885 | 71 | YLWGT LSEG (11) | QAMGR VVRSPS DYGAR ILLDGR (19) |
| 20 | XPD Nph | *Natronomonas pharaonis* | YP_326312.1 GI:76801304 | 43 | SLWGT LAEG (14) | QALGR VVRSP TDFGV RVLVD ER (21) |

TABLE 5-continued

More preferred XPD helicases and most preferred XPD motifs V and VI

| SEQ ID NO | Name | Strain | Accession No. | % Identity to XPD Mbu | Motif V (SEQ ID NO) | Motif VI (SEQ ID NO) |
|---|---|---|---|---|---|---|
| 22 | XPD Hoc | Haliangium ochraceum DSM | YP_003265400.1 GI:262194191 | 15 | VTGGV FAEG (23) | QAAGR VLRTPE DRGVI ALLGR R (24) |
| 25 | XPD Sbe | Shewanella benthica | ZP_02159638.1 GI:163752447 | 21 | LGTGA FWEG (26) | QGVGR LIRDER DRGVLI LCDNR (27) |
| 28 | XPD Mev | Methanohalobium evestigatum | YP_003727831.1 GI:298676081 | 71 | YIWGT LSEG (29) | QAMGR VVRSP TDYGA RILIDG R (30) |
| 31 | XPD Mba | Methanosarcina barkeri fusaro | YP_304917.1 GI:73668902 | 56 | YLWGT LSEG (11) | QAMGR IVRSPD DYGVR ILLDSR (32) |
| 33 | XPD Hvo | Haloferax volcanii | YP_003534113.1 GI:292654216 | 43 | SLWGT LAEG (14) | QALGR VIRAPD DFGVR VLADK R (34) |
| 35 | XPD Tac | Thermoplasma acidophilum | NP_393536.1 GI:16082477 | 24 | VSGGR LSEG (36) | QEIGRL IRSAED TGACVI LDKR (37) |
| 38 | XPD Tsi | Thermococcus sibiricus | YP_002994616.1 GI:242399192 | 24 | VMGGR NSEG (39) | QAAGR VHRSE EEKGA VVVLD YR (40) |
| 41 | XPD Pab | Pyrococcus abyssi | NP_127020.1 GI:14521544 | 24 | VMGGR NSEG (39) | QAAGR VHRSE EEKGSI VILDYR (42) |
| 43 | XPD Pfu | Pyrococcus furiosus | NP_578662.1 GI:18977305 | 25 | VMGGR NSEG (39) | QAAGR VHRSE EEKGSI VILDYR (42) |
| 44 | XPD Hsp | Halobacterium sp. NRC-1 | NP_281042.1 GI:15791218 | 41 | SLWGT LAEG 14) | QAMGR VIRSPE DFGVR MLVDR R (45) |
| 46 | XPD Mja | Methanocaldococcus jannaschii | NP_247937.1 GI:15669132 | 19 | LATGR FAEG (47) | QMIGR LIRTEN DYGVV VIQDK R (48) |
| 49 | XPD Sso | Sulfolobus solfataricus | NP_341859.1 GI:15897254 | 19 | IARGKL AEG (50) | QSIGRA IRGPTD NATIW LLDKR (51) |

TABLE 5-continued

More preferred XPD helicases and most preferred XPD motifs V and VI

| SEQ ID NO | Name | Strain | Accession No. | % Identity to XPD Mbu | Motif V (SEQ ID NO) | Motif VI (SEQ ID NO) |
|---|---|---|---|---|---|---|
| 52 | XPD Sac | Sulfolobus acidocaldarius | YP_254904.1 GI:70606034 | 20 | VGKGK LAEG (53) | QAIGR AIRDV NDKCN VWLLD KR (54) |
| 55 | XPD Tba | Thermococcus barophilus MP | YP_004071335.1 GI:315230899 | 25 | VMGGR NSEG (39) | QAAGR VHRSA EEKGAI IILDYR (56) |
| 57 | XPD Nma | Natrialba magadii | YP_003479905.1 GI:289581439 | 42 | SLWGT LAEG (14) | QALGR VIRSPE DVGVR ALLDR R (58) |
| 59 | XPD Hpa | Haladaptatus paucihalophilus | ZP_08042768.1 GI: 322368199 | 40 | SLWGT LAEG (14) | QALGR VIRSPE DFGVRI LLDKR (60) |
| 61 | XPD Htu | Haloterrigena turkmenica | YP_003401909.1 GI:284163630 | 38 | SLWGT LAEG (14) | QALGR VIRSPE DVGVR ALLDR R (58) |
| 62 | XPD Mmaz | Methanosarcina mazei | NP_633611.1 GI:21227689 | 55 | YLWGT LSEG (11) | QAMGR VVRSP GDFGV RILLDA R (17) |

The XPD helicase most preferably comprises the sequence shown in SEQ ID NO: 10 or a variant thereof.

A variant of a XPD helicase is an enzyme that has an amino acid sequence which varies from that of the wild-type helicase and which retains polynucleotide binding activity. In particular, a variant of any one of SEQ ID NOs: 10, 13, 16, 18, 20, 22, 25, 28, 31, 33, 35, 38, 41, 43, 44, 46, 49, 52, 55, 57, 59, 61 and 62 is an enzyme that has an amino acid sequence which varies from that of any one of SEQ ID NOs: 10, 13, 16, 18, 20, 22, 25, 28, 31, 33, 35, 38, 41, 43, 44, 46, 49, 52, 55, 57, 59, 61 and 62 and which retains polynucleotide binding activity. A variant of SEQ ID NO: 10 is an enzyme that has an amino acid sequence which varies from that of SEQ ID NO: 10 and which retains polynucleotide binding activity. The variant retains helicase activity. Methods for measuring helicase activity are known in the art. Helicase activity can also be measured as described in the Examples. The variant must work in at least one of the two modes discussed below. Preferably, the variant works in both modes. The variant may include modifications that facilitate handling of the polynucleotide encoding the helicase and/or facilitate its activity at high salt concentrations and/or room temperature. Variants typically differ from the wild-type helicase in regions outside of XPD motifs V and VI discussed above. However, variants may include modifications within one or both of these motifs.

Over the entire length of the amino acid sequence of any one of SEQ ID NOs: 10, 13, 16, 18, 20, 22, 25, 28, 31, 33, 35, 38, 41, 43, 44, 46, 49, 52, 55, 57, 59, 61 and 62, such as SEQ ID NO: 10, a variant will preferably be at least 10%, preferably 30% homologous to that sequence based on amino acid identity. More preferably, the variant polypeptide may be at least 40%, at least 45%, at least 50%, at least 55%, at least 60%, at least 65%, at least 70%, at least 75%, at least 80%, at least 85%, at least 90% and more preferably at least 95%, 97% or 99% homologous based on amino acid identity to the amino acid sequence of any one of SEQ ID NOs: 10, 13, 16, 18, 20, 22, 25, 28, 31, 33, 35, 38, 41, 43, 44, 46, 49, 52, 55, 57, 59, 61 and 62, such as SEQ ID NO: 10, over the entire sequence. There may be at least 70%, for example at least 80%, at least 85%, at least 90% or at least 95%, amino acid identity over a stretch of 150 or more, for example 200, 300, 400, 500, 600, 700, 800, 900 or 1000 or more, contiguous amino acids ("hard homology"). Homology is determined as described above. The variant may differ from the wild-type sequence in any of the ways discussed above with reference to SEQ ID NOs: 2 and 4.

In particular, variants may include fragments of SEQ ID NOs: 10, 13, 16, 18, 20, 22, 25, 28, 31, 33, 35, 38, 41, 43, 44, 46, 49, 52, 55, 57, 59, 61 and 62. Such fragments retain polynucleotide binding activity. Fragments may be at least about 200, at least about 300, at least about 400, at least about 500, at least about 600 or at least about 700 amino acids in length. The length of the fragment will typically depend on the length of the wild-type sequence. As discussed in more detail below, fragments preferably comprise the XPD motif V and/or the XPD motif VI of the relevant wild-type sequence.

Amino acid substitutions may be made to the amino acid sequence of SEQ ID NO: 10, 13, 16, 18, 20, 22, 25, 28, 31, 33, 35, 38, 41, 43, 44, 46, 49, 52, 55, 57, 59, 61 or 62, for example up to 1, 2, 3, 4, 5, 10, 20 or 30 substitutions. The substitutions are preferably conservative substitutions as discussed above.

A variant, such as a fragment, of any one of SEQ ID NOs: 10, 13, 16, 18, 20, 22, 25, 28, 31, 33, 35, 38, 41, 43, 44, 46, 49, 52, 55, 57, 59, 61 and 62 preferably comprises the XPD motif V and/or the XPD motif VI of the relevant wild-type sequence. A variant, such as a fragment, of any one of SEQ ID NOs: 10, 13, 16, 18, 20, 22, 25, 28, 31, 33, 35, 38, 41, 43, 44, 46, 49, 52, 55, 57, 59, 61 and 62 more preferably comprises the XPD motif V and the XPD motif VI of the relevant wild-type sequence. For instance, a variant of SEQ ID NO: 10 preferably comprises XPD motif V of SEQ ID NO: 10 (YLWGTLSEG; SEQ ID NO: 11) and/or XPD motif VI of SEQ ID NO: 10 (QAMGRVVRSPTDYGARILL-DGR; SEQ ID NO: 12). A variant of SEQ ID NO: 10 more preferably comprises both XPD motifs V and VI of SEQ ID NO: 10. The XPD motifs V and VI of each of SEQ ID NOs: 10, 13, 16, 18, 20, 22, 25, 28, 31, 33, 35, 38, 41, 43, 44, 46, 49, 52, 55, 57, 59, 61 and 62 are shown in Table 5. However, a variant of any one SEQ ID NOs 10, 13, 16, 18, 20, 22, 25, 28, 31, 33, 35, 38, 41, 43, 44, 46, 49, 52, 55, 57, 59, 61 and 62 may comprise XPD motifs V and/or VI from a different wild-type sequence. For instance, a variant of SEQ ID NO: 10 may comprise XPD motif V of SEQ ID NO: 13 (SLWGT-LAEG; SEQ ID NO: 14) and/or XPD motif VI of SEQ ID NO: 13 (QAIGRVVRGPDDFGVRILADRR; SEQ ID NO: 15). A variant of any one SEQ ID NOs: 10, 13, 16, 18, 20, 22, 25, 28, 31, 33, 35, 38, 41, 43, 44, 46, 49, 52, 55, 57, 59, 61 and 62 may comprise any one of the preferred motifs shown in Table 5. Variants of any one of SEQ ID NOs: 10, 13, 16, 18, 20, 22, 25, 28, 31, 33, 35, 38, 41, 43, 44, 46, 49, 52, 55, 57, 59, 61 and 62 may also include modifications within XPD motif V and/or XPD motif VI of the relevant wild-type sequence. Suitable modifications to these motifs are discussed above when defining the two motifs.

The helicase may be covalently attached to the pore. The helicase is preferably not covalently attached to the pore. The application of a voltage to the pore and helicase typically results in the formation of a sensor that is capable of sequencing target polynucleotides. This is discussed in more detail below.

Any of the proteins described herein, i.e. the transmembrane protein pores or XPD helicases, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the pore or helicase. An example of this would be to react a gel-shift reagent to a cysteine engineered on the outside of the pore. This has been demonstrated as a method for separating hemolysin hetero-oligomers (Chem. Biol. 1997 July; 4(7): 497-505).

The pore and/or helicase may be labelled with a revealing label. The revealing label may be any suitable label which allows the pore to be detected. Suitable labels include, but are not limited to fluorescent molecules, radioisotopes, e.g. $^{125}I$, $^{35}S$, enzymes, antibodies, antigens, polynucleotides and ligands such as biotin.

Proteins may be made synthetically or by recombinant means. For example, the pore and/or helicase may be synthesized by in vitro translation and transcription (IVTT). The amino acid sequence of the pore and/or helicase may be modified to include non-naturally occurring amino acids or to increase the stability of the protein. When a protein is produced by synthetic means, such amino acids may be introduced during production. The pore and/or helicase may also be altered following either synthetic or recombinant production.

The pore and/or helicase may also be produced using D-amino acids. For instance, the pore or helicase may comprise a mixture of L-amino acids and D-amino acids. This is conventional in the art for producing such proteins or peptides.

The pore and/or helicase may also contain other non-specific modifications as long as they do not interfere with pore formation or helicase function. A number of non-specific side chain modifications are known in the art and may be made to the side chains of the protein(s). Such modifications include, for example, reductive alkylation of amino acids by reaction with an aldehyde followed by reduction with $NaBH_4$, amidination with methylacetimidate or acylation with acetic anhydride.

The pore and helicase can be produced using standard methods known in the art. Polynucleotide sequences encoding a pore or helicase may be derived and replicated using standard methods in the art. Polynucleotide sequences encoding a pore or helicase may be expressed in a bacterial host cell using standard techniques in the art. The pore and/or helicase may be produced in a cell by in situ expression of the polypeptide from a recombinant expression vector. The expression vector optionally carries an inducible promoter to control the expression of the polypeptide. These methods are described in described in Sambrook, J. and Russell, D. (2001). Molecular Cloning: A Laboratory Manual, 3rd Edition. Cold Spring Harbor Laboratory Press, Cold Spring Harbor, N.Y.

The pore and/or helicase may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

The method of the invention involves measuring one or more characteristics of the target polynucleotide. The method may involve measuring two, three, four or five or more characteristics of the target polynucleotide. The one or more characteristics are preferably selected from (i) the length of the target polynucleotide, (ii) the identity of the target polynucleotide, (iii) the sequence of the target polynucleotide, (iv) the secondary structure of the target polynucleotide and (v) whether or not the target polynucleotide is modified. Any combination of (i) to (v) may be measured in accordance with the invention.

For (i), the length of the polynucleotide may be measured using the number of interactions between the target polynucleotide and the pore.

For (ii), the identity of the polynucleotide may be measured in a number of ways. The identity of the polynucleotide may be measured in conjunction with measurement of the sequence of the target polynucleotide or without measurement of the sequence of the target polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the target polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem. Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the target polynucleotide is modified by methylation, by oxidation, by damage, with one or more proteins or with one or more labels, tags or spacers. Specific modifications will result in specific interactions with the pore which can be measured using the methods described below. For instance, methylcyotsine may be distinguished from cytosine on the basis of the current flowing through the pore during its interaction with each nucleotide.

A variety of different types of measurements may be made. This includes without limitation: electrical measurements and optical measurements. Possible electrical measurements include: current measurements, impedance measurements, tunneling measurements (Ivanov A P et al., Nano Lett. 2011 Jan. 12; 11(1):279-85), and FET measurements (International Application WO 2005/124888). Optical measurements may be combined 10 with electrical measurements (Soni G V et al., Rev Sci Instrum. 2010 January; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem. Soc. 2010; 132(50):17961-72, and International Application WO-2000/28312. Alternatively, electrical measurements may be made using a multi-channel system, for example as described in International Application WO-2009/077734 and International Application WO-2011/067559.

In a preferred embodiment, the method comprises:

(a) contacting the target polynucleotide with a transmembrane pore and a XPD helicase such that the target polynucleotide moves through the pore and the XPD helicase controls the movement of the target polynucleotide through the pore; and (b) measuring the current passing through the pore as the polynucleotide moves with respect to the pore wherein the current is indicative of one or more characteristics of the target polynucleotide and thereby characterising the target polynucleotide.

The methods may be carried out using any apparatus that is suitable for investigating a membrane/pore system in which a pore is inserted into a membrane. The method may be carried out using any apparatus that is suitable for transmembrane pore sensing. For example, the apparatus comprises a chamber comprising an aqueous solution and a barrier that separates the chamber into two sections. The barrier has an aperture in which the membrane containing the pore is formed.

The methods may be carried out using the apparatus described in International Application No. PCT/GB08/000, 562 (WO 2008/102120).

The methods may involve measuring the current passing through the pore as the polynucleotide moves with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore as the polynucleotide moves with respect to the pore. Suitable conditions for measuring ionic currents through transmembrane protein pores are known in the art and disclosed in the Example. The method is typically carried out with a voltage applied across the membrane and pore. The voltage used is typically from +2 V to −2 V, typically −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl) or caesium chloride (CsCl) is typically used. KCl is preferred. The salt concentration may be at saturation. The salt concentration may be 3M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. As discussed above, XPD helicases surprisingly work under high salt concentrations. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is HEPES. Another suitable buffer is Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

The method is typically carried out in the presence of free nucleotides or free nucleotide analogues and an enzyme cofactor that facilitate the action of the helicase. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the helicase to function. The enzyme cofactor is preferably one or more divalent metal cations. Suitable divalent metal cations include, but are not limited to, $Mg^{2+}$, $Mn^{2+}$, $Ca^{2+}$, $Co^{2+}$ and $Fe^{2+}$. The enzyme cofactor is preferably $Fe^{2+}$ or $Mg^{2+}$. The enzyme cofactor is most preferably $Fe^{2+}$ and $Mg^{2+}$ The target polynucleotide may be contacted with the XPD helicase and the pore in any order. In is preferred that, when the target polynucleotide is contacted with the XPD helicase and the pore, the target polynucleotide firstly forms a complex with the helicase. When the voltage is applied across the pore, the target polynucleotide/helicase complex then forms a complex with the pore and controls the movement of the polynucleotide through the pore.

As discussed above, XPD helicases may work in two modes with respect to the pore. First, the method is preferably carried out using the XPD helicase such that it moves the target sequence through the pore with the field resulting from the applied voltage. In this mode the 5' end of the DNA is first captured in the pore, and the enzyme moves the DNA into the pore such that the target sequence is passed through the pore with the field until it finally translocates through to the trans side of the bilayer. Alternatively, the method is preferably carried out such that the enzyme moves the target sequence through the pore against the field resulting from the applied voltage. In this mode the 3' end of the DNA is first captured in the pore, and the enzyme moves the DNA through the pore such that the target sequence is pulled out of the pore against the applied field until finally ejected back to the cis side of the bilayer.

The method of the invention most preferably involves a pore derived from MspA and a helicase comprising the sequence shown in SEQ ID NO: 8 or a variant thereof. Any of the embodiments discussed above with reference to MspA and SEQ ID NO: 8 may be used in combination.

Other Methods

The invention also provides a method of forming a sensor for characterising a target polynucleotide. The method comprises forming a complex between a pore and a XPD helicase. The complex may be formed by contacting the pore and the helicase in the presence of the target polynucleotide and then applying a potential across the pore. The applied potential may be a chemical potential or a voltage potential as described above. Alternatively, the complex may be formed by covalently attaching the pore to the helicase. Methods for covalent attachment are known in the art and disclosed, for example, in International Application Nos. PCT/GB09/001,679 (published as WO 2010/004265) and PCT/GB10/000,133 (published as WO 2010/086603). The complex is a sensor for characterising the target polynucleotide. The method preferably comprises forming a complex between a pore derived from Msp and a XPD helicase. Any of the embodiments discussed above with reference to the method of the invention equally apply to this method.

Kits

The present invention also provides kits for characterising a target polynucleotide. The kits comprise (a) a pore and (b) a XPD helicase. Any of the embodiments discussed above with reference to the method of the invention equally apply to the kits.

The kit may further comprise the components of a membrane, such as the phospholipids needed to form an amphiphilic layer, such as a lipid bilayer.

The kits of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

Apparatus

The invention also provides an apparatus for characterising a target polynucleotide. The apparatus comprises a plurality of pores and a plurality of a XPD helicase. The apparatus preferably further comprises instructions for carrying out the method of the invention. The apparatus may be any conventional apparatus for polynucleotide analysis, such as an array or a chip. Any of the embodiments discussed above with reference to the methods of the invention are equally applicable to the apparatus of the invention.

The apparatus is preferably set up to carry out the method of the invention.

The apparatus preferably comprises:

a sensor device that is capable of supporting the membrane and plurality of pores and being operable to perform polynucleotide characterising using the pores and helicases;

at least one reservoir for holding material for performing the characterising;

a fluidics system configured to controllably supply material from the at least one reservoir to the sensor device; and a plurality of containers for receiving respective samples, the fluidics system being configured to supply the samples selectively from the containers to the sensor device. The apparatus may be any of those described in International Application No. PCT/GB08/004,127 (published as WO 2009/077734), PCT/GB10/000,789 (published as WO 2010/122293), International Application No. PCT/GB10/002,206 (not yet published) or International Application No. PCT/US99/25679 (published as WO 00/28312).

Characterisation without a Pore

In some embodiments, the target polynucleotide is characterised, such as partially or completely sequenced, using a XPD helicase, but without using a pore. In particular, the invention also provides a method of characterising a target polynucleotide which comprises contacting the target polynucleotide with a XPD helicase such that the XPD helicase controls the movement of the target polynucleotide. In this method, the target polynucleotide is preferably not contacted with a pore, such as a transmembrane pore. The method involves taking one or more measurements as the XPD helicase controls the movement of the polynucleotide and thereby characterising the target polynucleotide. The measurements are indicative of one or more characteristics of the target polynucleotide. Any such measurements may be taken in accordance with the invention. They include without limitation: electrical measurements and optical measurements. These are discussed in detail above. Any of the embodiments discussed above with reference to the pore-based method of the invention may be used in the method lacking a pore. For instance, any of the XPD helicases discussed above may be used.

The invention also provides an analysis apparatus comprising a XPD helicase. The invention also provides a kit a for characterising a target polynucleotide comprising (a) an analysis apparatus for characterising target polynucleotides and (b) a XPD helicase. These apparatus and kits preferably do not comprise a pore, such as a transmembrane pore. Suitable apparatus are discussed above.

The following Examples illustrate the invention.

Example 1

This example illustrates the use of a XPD helicase (XPD MBu) to control the movement of intact DNA strands through a nanopore. The general method and substrate employed throughout this example is shown in FIG. 1 and described in the figure caption.

Materials and Methods

Primers were designed to amplify a ~400 bp fragment of PhiX174. Each of the 5'-ends of these primers included a 50 nucleotide non-complimentary region, either a homopolymeric stretch or repeating units of 10 nucleotide homopolymeric sections. These serve as identifiers for controlled translocation of the strand through a nanopore, as well as determining the directionality of translocation. In addition, the 5'-end of the forward primer was "capped" to include four 2'-O-Methyl-Uracil (mU) nucleotides and the 5'-end of the reverse primer was chemically phosphorylated. These primer modifications then allow for the controlled digestion of predominantly only the antisense strand, using lambda exonuclease. The mU capping protects the sense strand from nuclease digestion whilst the PO4 at the 5' of the antisense strand promotes it. Therefore after incubation with lambda exonuclease only the sense strand of the duplex remains intact, now as single stranded DNA (ssDNA). The generated ssDNA was then PAGE purified as previously described.

Figure 1B:
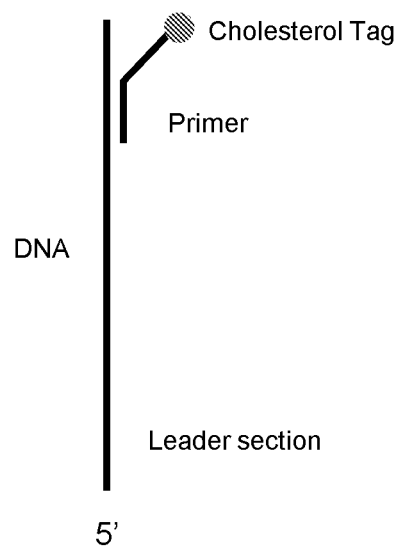

The DNA substrate design used in all the experiments described here is shown in FIG. 1B. The DNA substrate consists of a 400 base section of ssDNA from PhiX, with a 50T 5'-leader to aid capture by the nanopore (SEQ ID NO: 63). Annealed to this strand just after the 50T leader is a primer (SEQ ID NO: 64) containing a 3' cholesterol tag to enrich the DNA on the surface of the bilayer, and thus improve capture efficiency. An additional primer (SEQ ID NO: 65) is used towards the 3' end of the strand to aid the capture of the strand by the 3' end.

Buffered solution: 400 mM NaCl, 10 mM Hepes pH 8.0, 1 mM ATP, 1 mM $MgCl_2$, 1 mM DTT Nanopore: E. coli MS (B2)8 MspA ONLP3476 MS-(L88N/D90N/D91N/D93N/D118R/D134R/E139K)8

Enzyme: XPD Mbu (ONLP3696, ~6.2 µM) 16.1 µl→100 nM final.

Electrical measurements were acquired from single MspA nanopores inserted in 1,2-diphytanoyl-glycero-3-phosphocholine lipid (Avanti Polar Lipids) bilayers. Bilayers were formed across ~100 µm diameter apertures in 20 µm thick PTFE films (in custom Delrin chambers) via the Montal-Mueller technique, separating two 1 mL buffered solutions. All experiments were carried out in the stated buffered solution. Single-channel currents were measured on Axopatch 200B amplifiers (Molecular Devices) equipped with 1440A digitizers. Ag/AgCl electrodes were connected to the buffered solutions so that the cis compartment (to which both nanopore and enzyme/DNA are added) is connected to the ground of the Axopatch headstage, and the trans compartment is connected to the active electrode of the headstage. After achieving a single pore in the bilayer, DNA polynucleotide and helicase were added to 100 µL of buffer and pre-incubated for 5 mins (DNA=6 nM, Enzyme=1 µM) This pre-incubation mix was added to 900 µL of buffer in the cis compartment of the electrophysiology chamber to initiate capture of the helicase-DNA complexes in the MspA nanopore (to give final concentrations of DNA=0.6 nM, Enzyme=0.1 µM). Helicase ATPase activity was initiated as required by the addition of divalent metal (1 mM $MgCl_2$) and NTP (1 mM ATP) to the cis compartment. Experiments were carried out at a constant potential of +140 mV.

Results and Discussion

Figure 2:
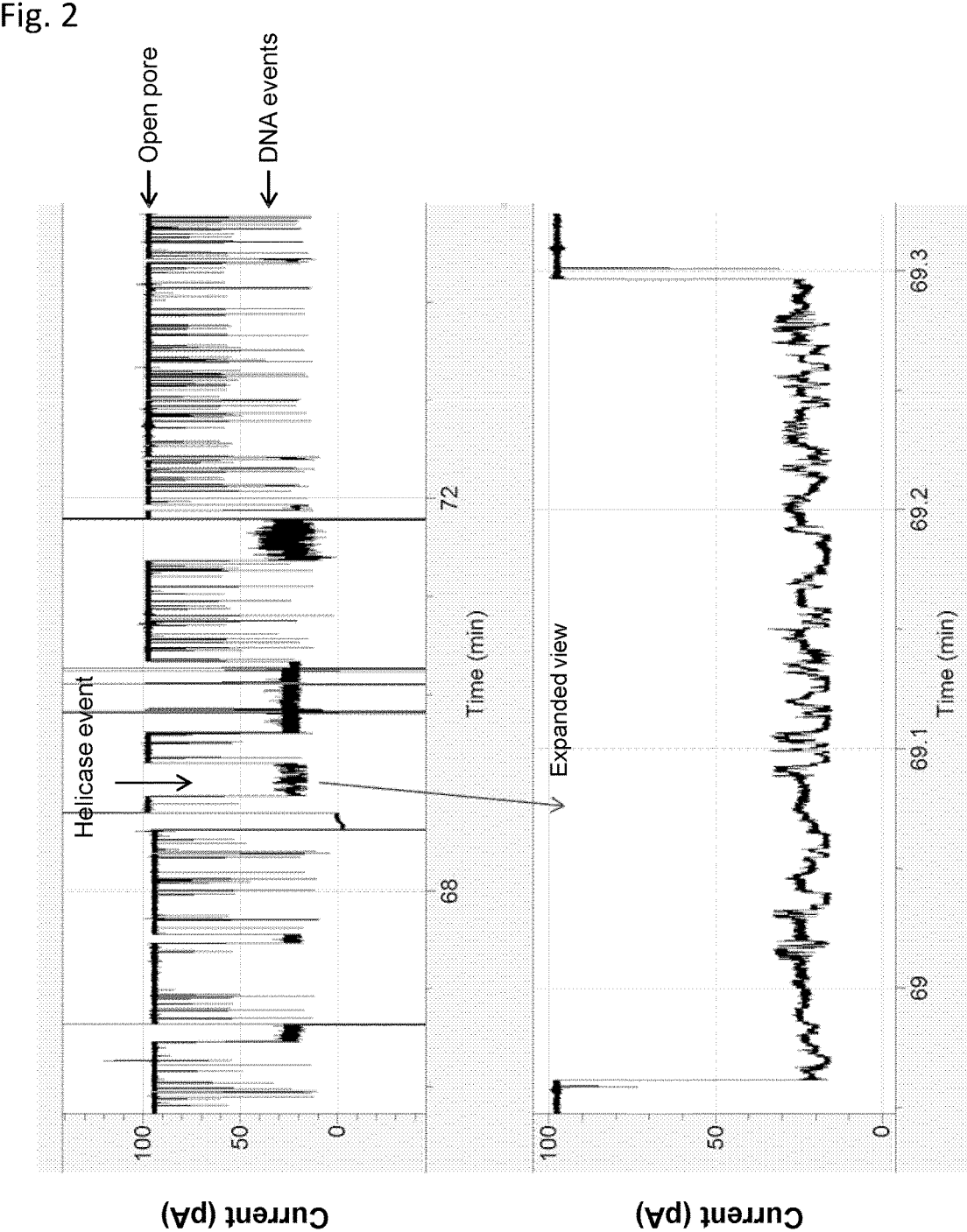
FIG. 2. Helicase is able to move DNA through a nanopore in a controlled fashion, producing stepwise changes in current as the DNA moves through the nanopore. Example helicase-DNA events (140 mV, 400 mM NaCl, Hepes pH 8.0, 0.6 nM 400 mer DNA, 100 nM XPD Mbu, 1 mM DTT, 1 mM ATP, 1 mM MgCl$_2$). Top) Section of current vs. time acquisition of XPD 400mer DNA events through an MspA B2 nanopore. The open-pore current is ~95 pA. DNA is captured by the nanopore under the force of the applied potential (+140 mV). DNA with enzyme attached results in a long block (at ~25 pA in this condition) that shows stepwise changes in current as the enzyme moves the DNA through the pore. Bottom) The bottom traces shows an enlargement of one of the helicase controlled DNA movement events, showing DNA-enzyme capture, stepwise current changes as the DNA is pulled through the pore.
Figure 3:
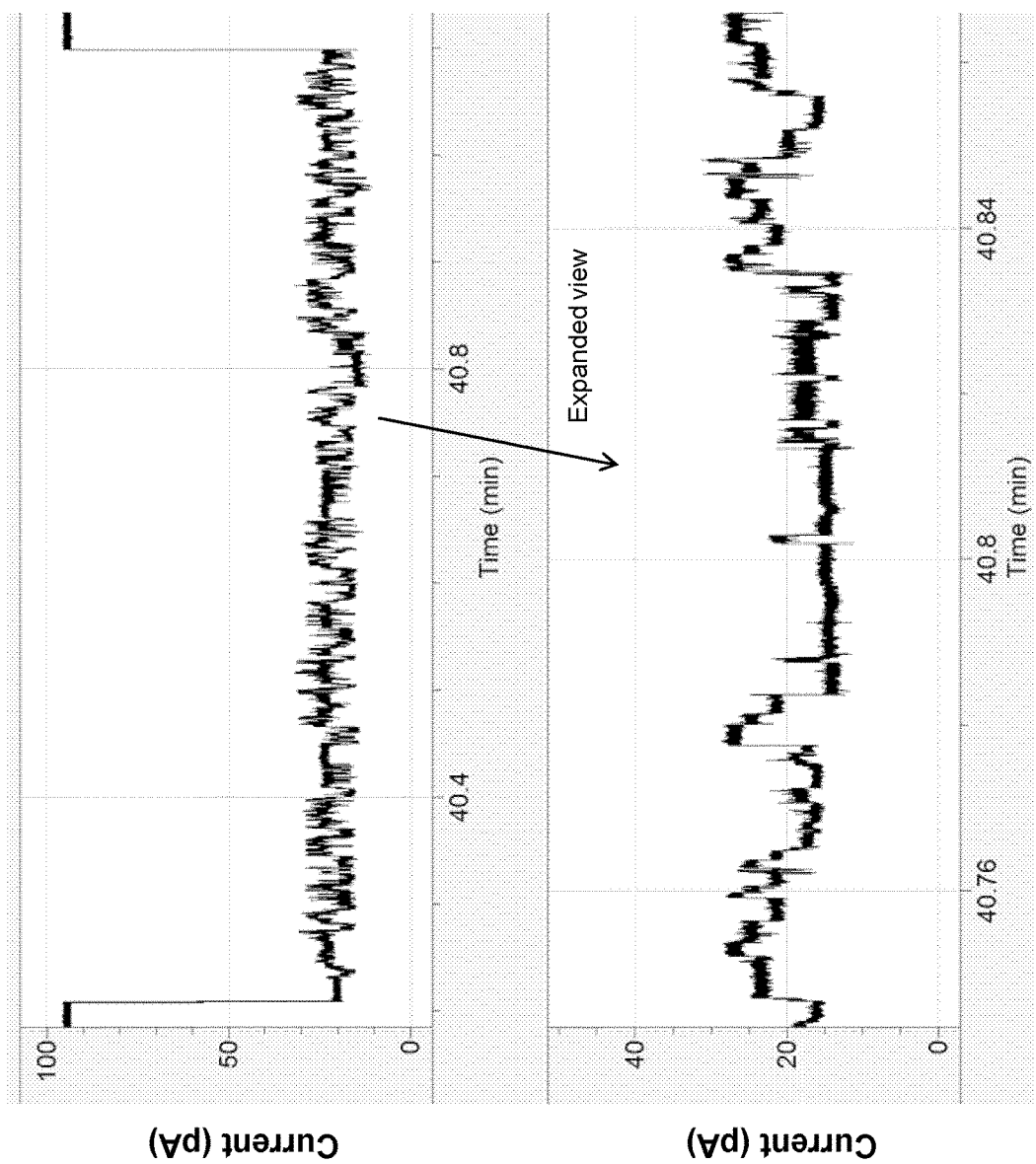
FIG. 3. A further example of helicase controlled DNA movement event. Bottom) An enlargement of a section of the event showing the stepwise changes in current from the different sections of DNA as the strand moves through the nanopore.

The addition of Helicase-DNA substrate to MspA nanopores as shown in FIG. 1 produces characteristic current blocks as shown in FIGS. 2 and 3. DNA which is not complexed with a helicase interacts transiently with the nanopore producing short-lived blocks in current (<<1 second). DNA with helicase bound and active (ie. moving along the DNA strand under ATPase action) produces long characteristic block levels with stepwise changes in current as shown in FIGS. 2 and 3. Different DNA motifs in the nanopore give rise to unique current block levels. For a given substrate, we observe a characteristic pattern of current transitions that reflects the DNA sequence.

In the implementation shown in FIG. 1, the DNA strand is sequenced from a random starting point as the DNA is captured with a helicase at a random position along the strand.

Salt Tolerance

Nanopore strand sequencing experiments of this type generally require ionic salts. The ionic salts are necessary to create a conductive solution for applying a voltage offset to capture and translocate DNA, and to measure the resulting sequence dependent current changes as the DNA passes through the nanopore. Since the measurement signal is dependent in the concentration of the ions, it is advantageous to use high concentration ionic salts to increase the magnitude of the acquired signal. For nanopore sequencing salt concentrations in excess of 100 mM KCl are ideal, and salt concentrations in excess of 400 mM are preferred.

However, many enzymes (including some helicases and DNA motor proteins) do not tolerate high salt conditions. Under high salt conditions the enzymes either unfold or lose structural integrity, or fail to function properly. The current literature for known and studied helicases shows that almost all helicases fail to function above salt concentrations of approximately 100 mM KCl/NaCl, and there are no reported helicases that show correct activity in conditions of 400 mM KCl and above. While potentially halophilic variants of similar enzymes from halotolerant species exist, they are extremely difficult to express and purify in standard expression systems (e.g. E. coli).

We surprisingly show in this Example that XPD from Mbu displays salt tolerance up to very high levels of salt. We find that the enzyme retains functionality in salt concentrations of 400 mM KCl through to 1 M KCl, either in fluorescence experiments or in nanopore experiments.

Forward and Reverse Modes of Operation

Figure 4:
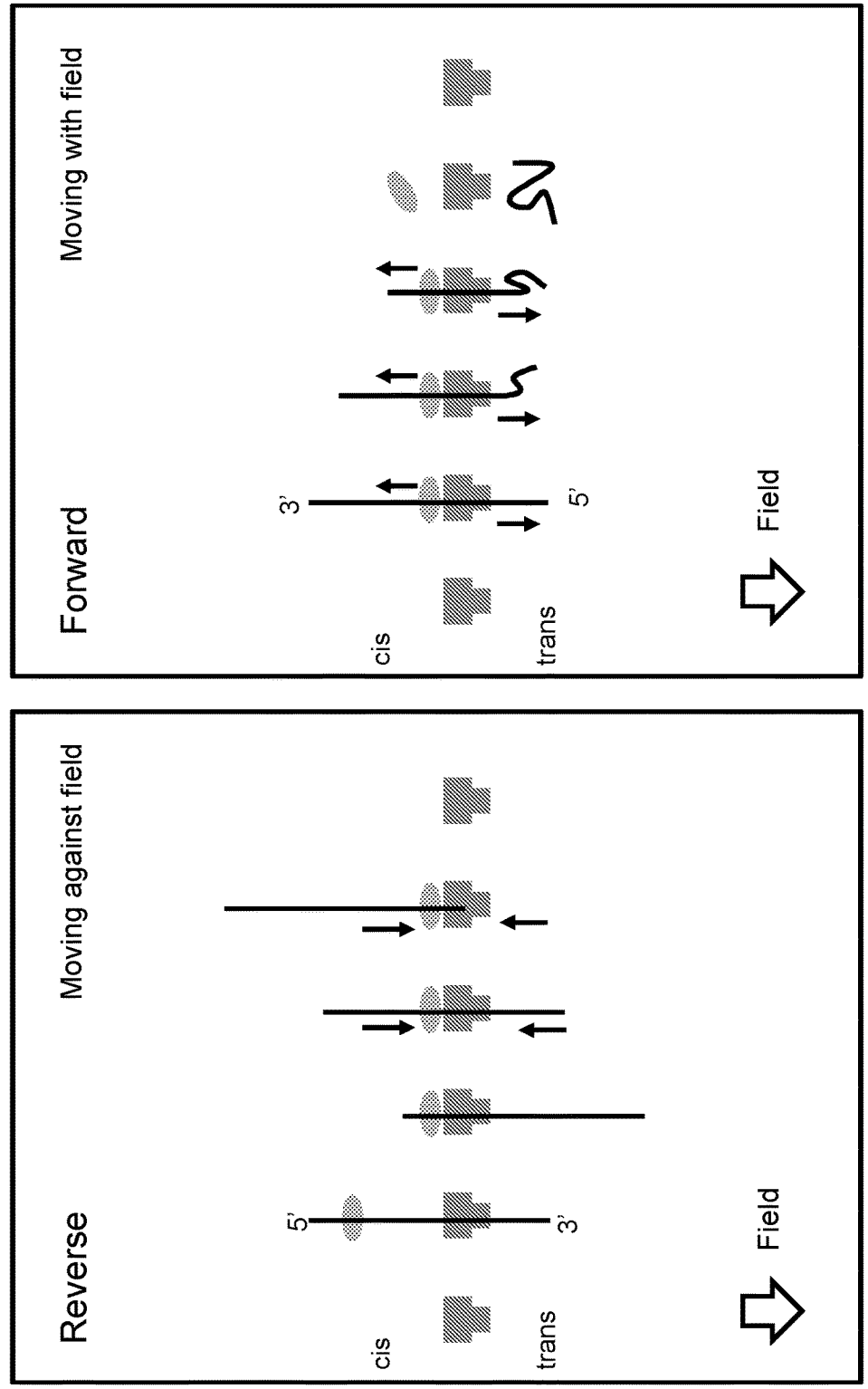
FIG. 4. The helicase can control the movement of DNA in at least two modes of operation. The helicase moves along the DNA in the 5'-3' direction, but the orientation of the DNA in the nanopore (dependent on which end of the DNA is captured) means that the enzyme can be used to either move the DNA out of the nanopore against the applied field, or move the DNA into the nanopore with the applied field. Left) When the 3' end of the DNA is captured the helicase works against the direction of the field applied by the voltage, pulling the threaded DNA out of the nanopore and into the cis chamber. Right) When the DNA is captured 5'-down in the nanopore, the enzyme moves the DNA into the nanopore in the direction of the field into the trans side of the bilayer.

Most helicases move along single-stranded polynucleotide substrates in uni-directional manner, moving a specific number of bases for each NTPase turned over. Although FIG. 1 illustrates the use of this movement to feed threaded DNA through the nanopore into the trans chamber in the same direction as the applied potential, helicase movement could be exploited in other manners to feed DNA through the nanopore in a controlled fashion. FIG. 4 illustrates two basic 'forward' and 'reverse' modes of operation. In the forward mode, the DNA is fed into the pore by the helicase in the same direction as the DNA would move under the force of the applied field. The direction of movement of the DNA is shown by the trans arrows. For XPD Mbu, which is a 5'-3' helicase, this requires capturing the 5' end of the DNA in the nanopore until a helicase contacts the top of the nanopore, and the DNA is then fed into the nanopore under the control of the helicase with the field from the applied potential, moving from cis to trans. The reverse mode requires capturing the 3' end of the DNA, after which the helicase proceeds to pull the threaded DNA back out of the nanopore against the field from the applied potential, moving the DNA from cis to trans as indicated by the arrows. FIG. 4 shows these two modes of operation using XPD Mbu.

Example 2

This example illustrates the salt tolerance of a XPD helicase (XPD Mbu) using a fluorescence assay for testing enzyme activity.

Figure 5A:
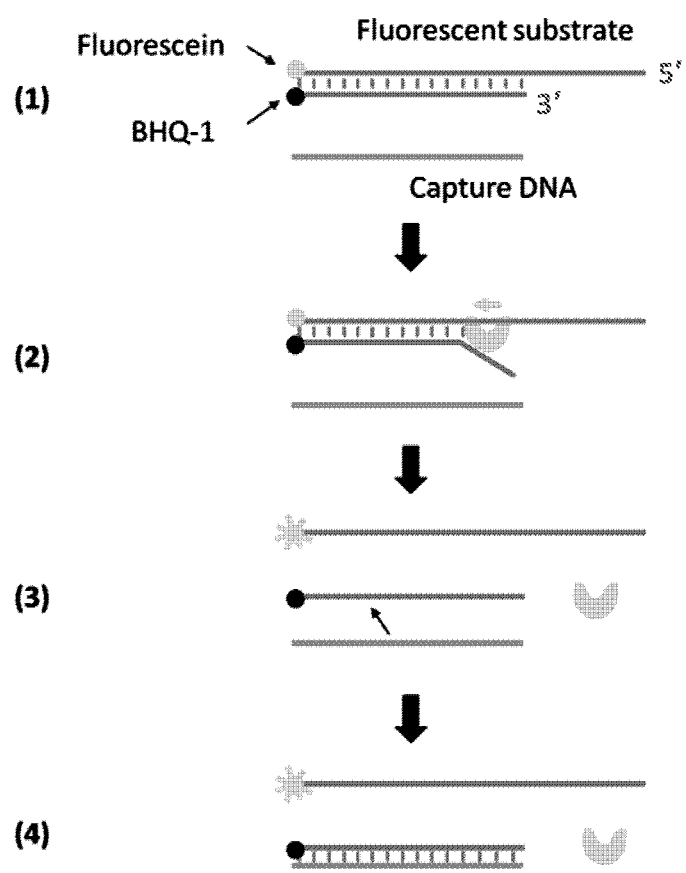
FIG. 5. Fluorescence assay for testing enzyme activity. A) A custom fluorescent substrate was used to assay the ability of the helicase to displace hybridised dsDNA. 1) The fluorescent substrate strand (50 nM final) has a 5' ssDNA overhang, and a 40 base section of hybridised dsDNA. The major upper strand has a carboxyfluorescein base at the 3' end, and the hybridised complement has a black-hole quencher (BHQ-1) base at the 5' end. When hybridised the fluorescence from the fluorescein is quenched by the local BHQ-1, and the substrate is essentially non-fluorescent. 1 µM of a capture strand that is complementary to the shorter strand of the fluorescent substrate is included in the assay. 2) In the presence of ATP (1 mM) and MgCl$_2$ (10 mM), helicase (150 nM) added to the substrate binds to the 5' tail of the fluorescent substrate, moves along the major strand, and displaces the complementary strand as shown. 3) Once the complementary strand with BHQ-1 is fully displaced the fluorescein on the major strand fluoresces. 4) Excess of capture strand preferentially anneals to the complementary DNA to prevent re-annealing of initial substrate and loss of fluorescence. B) Graph of the initial rate of Mbu XPD helicase activity in buffer solutions (100 mM Hepes pH 8.0, 1 mM ATP, 10 mM MgCl$_2$, 50 nM fluorescent substrate DNA, 1 µM capture DNA) containing different concentrations of KCl from 100 mM to 2 M.

A custom fluorescent substrate was used to assay the ability of the helicase to displace hybridised dsDNA (FIG. 5A). As shown in 1) of FIG. 5A, the fluorescent substrate strand (50 nM final) has a 5' ssDNA overhang, and a 40 base section of hybridised dsDNA. The major upper strand has a carboxyfluorescein base at the 3' end, and the hybrised complement has a black-hole quencher (BHQ-1) base at the 5' end. When hybrised the fluorescence from the fluorescein is quenched by the local BHQ-1, and the substrate is essentially non-fluorescent. 1 μM of a capture strand that is complementary to the shorter strand of the fluorescent substrate is included in the assay. As shown in 2), in the presence of ATP (1 mM) and $MgCl_2$ (10 mM), helicase (150 nM) added to the substrate binds to the 5' tail of the fluorescent substrate, moves along the major strand, and displaces the complementary strand as shown. As shown in 3), once the complementary strand with BHQ-1 is fully displaced the fluorescein on the major strand fluoresces. As shown in 4), an excess of capture strand preferentially anneals to the complementary DNA to prevent re-annealing of initial substrate and loss of fluorescence.

Substrate DNA: SEQ ID NO 66 with a carboxyfluorescein near the 3' end and SEQ ID NO: 67 with a Black Hole Quencher-1 at the 5' end.

Capture DNA: SEQ ID NO: 68 with a carboxyfluorescein near the 3' end.

Figure 5B:
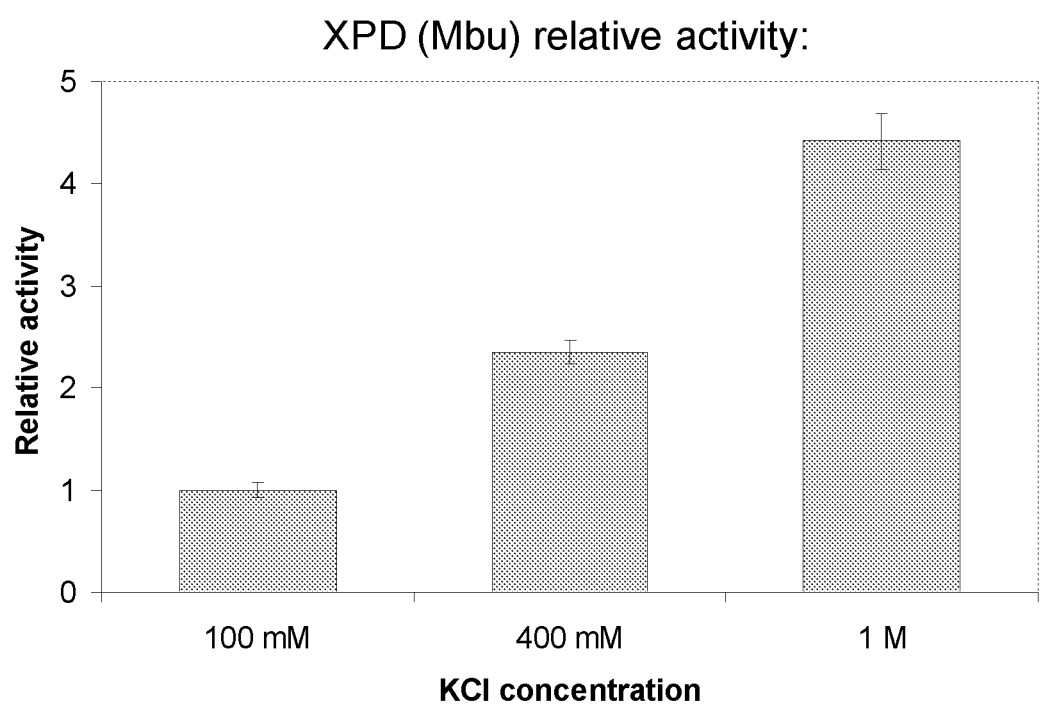
Figure 6:
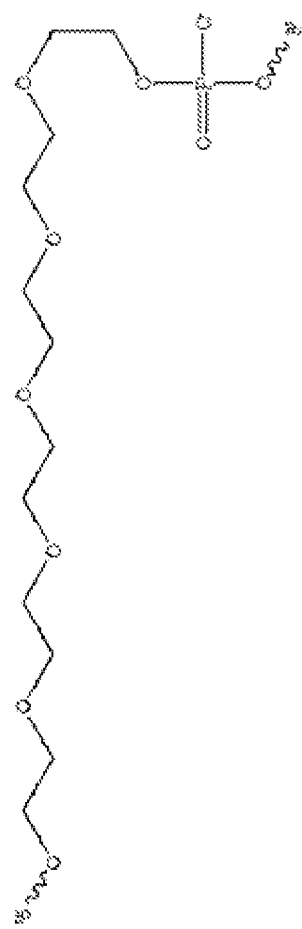
FIG. 6. The structure of the spacer iSp18 used in Example 1.

The graph in FIG. 5B shows the initial rate of activity in buffer solutions (100 mM Hepes pH 8.0, 1 mM ATP, 10 mM $MgCl_2$, 50 nM fluorescent substrate DNA, 1 μM capture DNA) containing different concentrations of KCl from 100 mM to 1 M. The helicase works at 1 M.

The invention claimed is:

1. A method of characterising a target polynucleotide, comprising:
   (a) providing a transmembrane nanopore and a membrane in an aqueous solution, wherein the transmembrane nanopore is present in the membrane, and wherein the aqueous solution comprises a salt at a concentration in a range of 0.3 M to 1 M;
   (b) combining in the aqueous solution of step (a) a target polynucleotide and a XPD helicase under conditions in which the helicase binds to the target polynucleotide and controls the movement of the target polynucleotide through the nanopore; and
   (c) measuring, during application of a potential across the nanopore, ion flow through the transmembrane nanopore as the polynucleotide moves through the nanopore wherein the ion flow measurements are indicative of one or more characteristics of the target polynucleotide, wherein the one or more characteristics are selected from (i) the length of the target polynucleotide, (ii) the identity of the target polynucleotide, (iii) the sequence of the target polynucleotide, (iv) the secondary structure of the target polynucleotide and (v) whether or not the target polynucleotide is modified, and thereby characterising the target polynucleotide.

2. The method according to claim 1, wherein the target polynucleotide is modified by methylation, by oxidation, by damage, with one or more proteins or with one or more labels, tags or spacers.

3. The method according to claim 1, wherein the ion flow measurements comprise a current measurement, an impedance measurement, a tunnelling measurement or a field effect transistor (FET) measurement.

4. The method according to claim 1, wherein the method further comprises the step of applying a voltage across the nanopore to form a complex between the nanopore and the helicase.

5. The method according to claim 1, wherein at least a portion of the polynucleotide is double stranded.

6. The method according to claim 1, wherein the nanopore is a transmembrane protein nanopore or a solid state nanopore, optionally wherein the transmembrane protein nanopore is selected from α-hemolysin, leukocidin, *Mycobacterium smegmatis* porin A (MspA), outer membrane porin F (OmpF), outer membrane porin G (OmpG), outer membrane phospholipase A, *Neisseria* autotransporter lipoprotein (NalP) and WZA.

7. The method according to claim 6, wherein the transmembrane protein nanopore is (a) formed of eight identical subunits as shown in SEQ ID NO: 2 or a variant thereof in which one or more of the seven subunits has at least 50% homology to SEQ ID NO: 2 based on amino acid identity over the entire sequence and retains pore activity, or (b) α-hemolysin formed of seven identical subunits as shown in SEQ ID NO: 4 or a variant thereof in which one or more of the seven subunits has at least 50% homology to SEQ ID NO: 4 based on amino acid identity over the entire sequence and retains pore activity.

8. The method according to claim 1, wherein the XPD helicase comprises:

the amino acid motif X1-X2-X3-G-X4-X5-X6-E-G (SEQ ID NO: 8), wherein X1, X2, X5 and X6 are independently selected from any amino acid except D, E, K and R and wherein X3 and X4 may be any amino acid residue: and/or the amino acid motif Q-Xa-Xb-G-R-Xc-Xd-R-(Xe)$_3$-Xf-(Xg)$_7$-D-Xh-R (SEQ ID NO: 9), wherein Xa, Xe and Xg may be any amino acid residue and wherein Xb, Xc and Xd are independently selected from any amino acid except D, E, K and R, optionally wherein X1, X2, X5 and X6 and/or Xb, Xc and Xd are independently selected from G, P, A, V, L, I, M, C, F, Y, W, H, Q, N, S and T.

9. The method according to claim 8, wherein the helicase comprises the following motifs:

(a)
```
                                              (SEQ ID NO: 11)
YLWGTLSEG
```
and/or
```
                                              (SEQ ID NO: 12)
QAMGRVVRSPTDYGARILLDGR;
```

(b)
SLWGTLAEG (SEQ ID NO: 14)
and/or

QAIGRVVRGPDDFGVRILADRR; (SEQ ID NO: 15)

(c)
YLWGTLSEG (SEQ ID NO: 11)
and/or

QAMGRVVRSPGDFGVRILLDAR; (SEQ ID NO: 17)

(d)
YLWGTLSEG (SEQ ID NO: 11)
and/or

QAMGRVVRSPSDYGARILLDGR (SEQ ID NO: 19)

(e)
SLWGTLAEG (SEQ ID NO: 14)
and/or

QALGRVVRSPTDFGVRVLVDER; (SEQ ID NO: 21)

(f)
VTGGVFAEG (SEQ ID NO: 23)
and/or

QAAGRVLRTPEDRGVIALLGRR; (SEQ ID NO: 24)

(g)
LGTGAFWEG (SEQ ID NO: 26)
and/or

QGVGRLIRDERDRGVLILCDNR; (SEQ ID NO: 27)

(h)
YIWGTLSEG (SEQ ID NO: 29)
and/or

QAMGRVVRSPTDYGARILIDGR; (SEQ ID NO: 30)

(i)
YLWGTLSEG (SEQ ID NO: 11)
and/or

QAMGRIVRSPDDYGVRILLDSR; (SEQ ID NO: 32)

(j)
SLWGTLAEG (SEQ ID NO: 14)
and/or

QALGRVIRAPDDFGVRVLADKR; (SEQ ID NO: 34)

(k)
VSGGRLSEG (SEQ ID NO: 36)
and/or

QEIGRLIRSAEDTGACVILDKR; (SEQ ID NO: 37)

(l)
VMGGRNSEG (SEQ ID NO: 39)
and/or

QAAGRVHRSEEEKGAVVVLDYR; (SEQ ID NO: 40)

(m)
VMGGRNSEG (SEQ ID NO: 39)
and/or

QAAGRVHRSEEEKGSIVILDYR; (SEQ ID NO: 42)

(n)
SLWGTLAEG (SEQ ID NO: 14)
and/or

QAMGRVIRSPEDFGVRMLVDRR; (SEQ ID NO: 45)

(o)
LATGRFAEG (SEQ ID NO: 47)
and/or

QMIGRLIRTENDYGVVVIQDKR; (SEQ ID NO: 48)

(p)
IARGKLAEG (SEQ ID NO: 50)
and/or

QSIGRAIRGPTDNATIWLLDKR; (SEQ ID NO: 51)

(q)
VGKGKLAEG (SEQ ID NO: 53)
and/or

QAIGRAIRDVNDKCNVWLLDKR; (SEQ ID NO: 54)

(r)
VMGGRNSEG (SEQ ID NO: 39)
and/or

QAAGRVHRSAEEKGAIIILDYR; (SEQ ID NO: 56)

(s)
SLWGTLAEG (SEQ ID NO: 14)
and/or

QALGRVIRSPEDVGVRALLDRR; (SEQ ID NO: 58)

(t)
SLWGTLAEG (SEQ ID NO: 14)
and/or

QALGRVIRSPEDFGVRILLDKR; (SEQ ID NO: 60)
or

-continued (u)
YLWGTLSEG
and/or
(SEQ ID NO: 11)

QAMGRVVRSPGDFGVRILLDAR.
(SEQ ID NO: 17)

10. The method according to claim 1, wherein the XPD helicase is one of the helicases shown in Table 4 or 5 or a variant thereof, optionally wherein the XPD helicase comprises (a) the sequence shown in any one of SEQ ID NOs: 10, 13, 16, 18, 20, 22, 25, 28, 31, 33, 35, 38, 41, 43, 44, 46, 49, 52, 55, 57, 59, 61 and 62 or (b) a variant thereof having at least 30% homology to the relevant sequence based on amino acid identity over the entire sequence and retains helicase activity.

11. The method according to claim 10, wherein the XPD helicase comprises (a) the sequence shown in SEQ ID NO: 10 or (b) a variant thereof having at least 40% homology to the SEQ ID NO: 10 based on amino acid identity over the entire sequence and retains helicase activity.

12. The method according to claim 1, wherein the salt is KCl.

* * * * *

SEQUENCE LISTING

```
<160> NUMBER OF SEQ ID NOS: 68

<210> SEQ ID NO 1
<211> LENGTH: 558
<212> TYPE: DNA
<213> ORGANISM: Artificial Sequence
<220> FEATURE:
<223> OTHER INFORMATION: Codon optimised sequence encoding MS-B1 mutant
      MspA monomer

<400> SEQUENCE: 1
atgggtctgg ataatgaact gagcctggtg gacggtcaag atcgtaccct gacggtgcaa      60
caatgggata cctttctgaa tggcgttttt ccgctggatc gtaatcgcct gacccgtgaa     120
tggtttcatt ccggtcgcgc aaaatatatc gtcgcaggcc cgggtgctga cgaattcgaa     180
ggcacgctgg aactgggtta tcagattggc tttccgtggt cactgggcgt tggtatcaac     240
ttctcgtaca ccacgccgaa tattctgatc aacaatggta acattaccgc accgccgttt     300
ggcctgaaca gcgtgattac gccgaacctg tttccgggtg ttagcatctc tgcccgtctg     360
ggcaatggtc cgggcattca agaagtggca acctttagtg tgcgcgtttc cggcgctaaa     420
```

```
ggcggtgtcg cggtgtctaa cgcccacggt accgttacgg gcgcggccgg cggtgtcctg    480
ctgcgtccgt tcgcgcgcct gattgcctct accggcgaca cgttacgac ctatggcgaa      540 ccgtggaata tgaactaa                                                    558
```

```
<210> SEQ ID NO 2
<211> LENGTH: 184
<212> TYPE: PRT
<213> ORGANISM: Artificial Sequence
<220> FEATURE:
<223> OTHER INFORMATION: Mature form of the MS-B1 mutant MspA monomer

<400> SEQUENCE: 2
```

```
Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asn Asn Gly Asn Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Arg Leu Gly Asn Gly Pro Gly Ile Gln Glu Val
        115                 120                 125

Ala Thr Phe Ser Val Arg Val Ser Gly Ala Lys Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180
```

```
<210> SEQ ID NO 3
<211> LENGTH: 885
<212> TYPE: DNA
<213> ORGANISM: Artificial Sequence
<220> FEATURE:
<223> OTHER INFORMATION: Alpha-hemolysin-NN

<400> SEQUENCE: 3
```

```
atggcagatt ctgatattaa tattaaaacc ggtactacag atattggaag caatactaca    60
gtaaaaacag gtgatttagt cacttatgat aaagaaaatg gcatgcacaa aaaagtattt    120
tatagtttta tcgatgataa aaatcacaat aaaaaactgc tagttattag aacaaaaggt    180
accattgctg gtcaatatag agtttatagc gaagaaggtg ctaacaaaag tggtttagcc    240
tggcctccag cctttaaggt acagttgcaa ctacctgata tgaagtagc tcaaatatct    300 gattactatc caagaaattc gattgataca aaaaactata tgagtacttt aacttatgga    360
ttcaacggta atgttactgg tgatgataca ggaaaaattg gcggccttat tggtgcaaat    420
gtttcgattg gtcatacact gaactatgtt caacctgatt caaaacaat tttagagagc    480 ccaactgata aaaagtagg ctggaaagtg atatttaaca atatggtgaa tcaaaattgg    540
```

```
ggaccatacg atcgagattc ttggaacccg gtatatggca atcaactttt catgaaaact    600
agaaatggtt ctatgaaagc agcagataac ttccttgatc ctaacaaagc aagttctcta    660
ttatcttcag ggttttcacc agacttcgct acagttatta ctatggatag aaaagcatcc    720
aaacaacaaa caaatataga gtaatatac gaacgagttc gtgatgatta ccaattgcat    780
tggacttcaa caaattggaa aggtaccaat actaaagata atggacaga tcgttcttca    840 gaaagatata aaatcgattg ggaaaaagaa gaaatgacaa attaa    885
```

<210> SEQ ID NO 4
<211> LENGTH: 293
<212> TYPE: PRT
<213> ORGANISM: Artificial Sequence
<220> FEATURE:
<223> OTHER INFORMATION: Alpha-hemolysin-NN

<400> SEQUENCE: 4

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290
```

<210> SEQ ID NO 5
<211> LENGTH: 184
<212> TYPE: PRT
<213> ORGANISM: Mycobacterium smegmatis

<400> SEQUENCE: 5

```
Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Gly Val Ala Val
    130                 135                 140

Ser Asn Ala His Gly Thr Val Thr Gly Ala Ala Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180
```

<210> SEQ ID NO 6
<211> LENGTH: 184
<212> TYPE: PRT
<213> ORGANISM: Mycobacterium smegmatis

<400> SEQUENCE: 6

```
Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Gly
                85                  90                  95

Pro Pro Phe Gly Leu Glu Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Gly Val Ala Val
    130                 135                 140
```

```
Ser Asn Ala His Gly Thr Val Thr Gly Ala Ala Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 7
<211> LENGTH: 183
<212> TYPE: PRT
<213> ORGANISM: Mycobacterium smegmatis

<400> SEQUENCE: 7

Val Asp Asn Gln Leu Ser Val Val Asp Gly Gln Gly Arg Thr Leu Thr
1               5                   10                  15

Val Gln Gln Ala Glu Thr Phe Leu Asn Gly Val Phe Pro Leu Asp Arg
                20                  25                  30

Asn Arg Leu Thr Arg Glu Trp Phe His Ser Gly Arg Ala Thr Tyr His
            35                  40                  45

Val Ala Gly Pro Gly Ala Asp Glu Phe Glu Gly Thr Leu Glu Leu Gly
        50                  55                  60

Tyr Gln Val Gly Phe Pro Trp Ser Leu Gly Val Gly Ile Asn Phe Ser
65                  70                  75                  80

Tyr Thr Thr Pro Asn Ile Leu Ile Asp Gly Asp Ile Thr Gln Pro
                85                  90                  95

Pro Phe Gly Leu Asp Thr Ile Ile Thr Pro Asn Leu Phe Pro Gly Val
            100                 105                 110

Ser Ile Ser Ala Asp Leu Gly Asn Gly Pro Gly Ile Gln Glu Val Ala
        115                 120                 125

Thr Phe Ser Val Asp Val Lys Gly Ala Lys Gly Ala Val Ala Val Ser
130                 135                 140

Asn Ala His Gly Thr Val Thr Gly Ala Ala Gly Gly Val Leu Leu Arg
145                 150                 155                 160

Pro Phe Ala Arg Leu Ile Ala Ser Thr Gly Asp Ser Val Thr Thr Tyr
                165                 170                 175

Gly Glu Pro Trp Asn Met Asn
            180

<210> SEQ ID NO 8
<211> LENGTH: 9
<212> TYPE: PRT
<213> ORGANISM: Artificial Sequence
<220> FEATURE:
<223> OTHER INFORMATION: XPD motif V
<220> FEATURE:
<221> NAME/KEY: MISC_FEATURE
<222> LOCATION: (1)..(1)
<223> OTHER INFORMATION: Any amino acid except D, E, K or R.
      Preferably not charged or H. More preferably V, L, I, S or Y.
<220> FEATURE:
<221> NAME/KEY: MISC_FEATURE
<222> LOCATION: (2)..(2)
<223> OTHER INFORMATION: Any amino acid except D, E, K or R.
      Preferably not charged or H.
<220> FEATURE:
<221> NAME/KEY: MISC_FEATURE
<222> LOCATION: (3)..(3)
<223> OTHER INFORMATION: Any amino acid.
<220> FEATURE:
<221> NAME/KEY: MISC_FEATURE
<222> LOCATION: (5)..(5)
<223> OTHER INFORMATION: Any amino acid.  Preferably K, R or T.
```

```
<220> FEATURE:
<221> NAME/KEY: MISC_FEATURE
<222> LOCATION: (6)..(6)
<223> OTHER INFORMATION: Any amino acid except D, E, K or R.
      Preferably not charged or H. More preferably V, L, I, N or F.
<220> FEATURE:
<221> NAME/KEY: MISC_FEATURE
<222> LOCATION: (7)..(7)
<223> OTHER INFORMATION: Any amino acid except D, E, K or R.
      Preferably not charged or H. More preferably S or A.

<400> SEQUENCE: 8

Xaa Xaa Xaa Gly Xaa Xaa Xaa Glu Gly
1               5

<210> SEQ ID NO 9
<211> LENGTH: 22
<212> TYPE: PRT
<213> ORGANISM: Artificial Sequence
<220> FEATURE:
<223> OTHER INFORMATION: XPD motif VI
<220> FEATURE:
<221> NAME/KEY: MISC_FEATURE
<222> LOCATION: (2)..(2)
<223> OTHER INFORMATION: Any amino acid
<220> FEATURE:
<221> NAME/KEY: MISC_FEATURE
<222> LOCATION: (3)..(3)
<223> OTHER INFORMATION: Any amino acid except D, E, K, R.
      Typically G, P, A, V, L, I, M, C, F, Y, W, H, Q, N, S or T.
      Preferably not charged.  Preferably not H.  More preferably
      V, A, L, I or M.
<220> FEATURE:
<221> NAME/KEY: MISC_FEATURE
<222> LOCATION: (6)..(6)
<223> OTHER INFORMATION: Any amino acid except D, E, K, R.  Typically
      G, P, A, V, L, I, M, C, F, Y, W, H, Q, N, S or T.  Preferably not
      charged.  Preferably not H.  More preferably V, A, L, I, M or C.
<220> FEATURE:
<221> NAME/KEY: MISC_FEATURE
<222> LOCATION: (7)..(7)
<223> OTHER INFORMATION: Any amino acid except D, E, K, R.  Typically
      G, P, A, V, L, I, M, C, F, Y, W, H, Q, N, S or T.  Preferably not
      charged.  Preferably not H.  More preferably I, H, L, F, M or V.
<220> FEATURE:
<221> NAME/KEY: MISC_FEATURE
<222> LOCATION: (9)..(11)
<223> OTHER INFORMATION: Any amino acid.
<220> FEATURE:
<221> NAME/KEY: MISC_FEATURE
<222> LOCATION: (12)..(12)
<223> OTHER INFORMATION: D or E
<220> FEATURE:
<221> NAME/KEY: MISC_FEATURE
<222> LOCATION: (13)..(13)
<223> OTHER INFORMATION: Any amino acid.
<220> FEATURE:
<221> NAME/KEY: MISC_FEATURE
<222> LOCATION: (14)..(14)
<223> OTHER INFORMATION: Any amino acid.  Preferably G, A, S or C
<220> FEATURE:
<221> NAME/KEY: MISC_FEATURE
<222> LOCATION: (15)..(16)
<223> OTHER INFORMATION: Any amino acid.
<220> FEATURE:
<221> NAME/KEY: MISC_FEATURE
<222> LOCATION: (17)..(17)
<223> OTHER INFORMATION: Any amino acid. Preferably F, V, L, I, M, A, W
      or Y
<220> FEATURE:
<221> NAME/KEY: MISC_FEATURE
<222> LOCATION: (18)..(18)
<223> OTHER INFORMATION: Any amino acid. Preferably L, F, Y, M, I or V.
<220> FEATURE:
<221> NAME/KEY: MISC_FEATURE
<222> LOCATION: (19)..(19)
<223> OTHER INFORMATION: Any amino acid. Preferably A, C, V, L, I, M or
```

```
S.

<400> SEQUENCE: 9

Gln Xaa Xaa Gly Arg Xaa Xaa Arg Xaa Xaa Xaa Xaa Xaa Xaa Xaa Xaa
1               5                   10                  15

Xaa Xaa Xaa Asp Asn Arg
            20

<210> SEQ ID NO 10
<211> LENGTH: 726
<212> TYPE: PRT
<213> ORGANISM: Methanococcoides burtonii

<400> SEQUENCE: 10

Met Ser Asp Lys Pro Ala Phe Met Lys Tyr Phe Thr Gln Ser Cys
1               5                   10                  15

Tyr Pro Asn Gln Gln Glu Ala Met Asp Arg Ile His Ser Ala Leu Met
                20                  25                  30

Gln Gln Gln Leu Val Leu Phe Glu Gly Ala Cys Gly Thr Gly Lys Thr
            35                  40                  45

Leu Ser Ala Leu Val Pro Ala Leu His Val Gly Lys Met Leu Gly Lys
        50                  55                  60

Thr Val Ile Ile Ala Thr Asn Val His Gln Gln Met Val Gln Phe Ile
65                  70                  75                  80

Asn Glu Ala Arg Asp Ile Lys Lys Val Gln Asp Val Lys Val Ala Val
                85                  90                  95

Ile Lys Gly Lys Thr Ala Met Cys Pro Gln Glu Ala Asp Tyr Glu Glu
            100                 105                 110

Cys Ser Val Lys Arg Glu Asn Thr Phe Glu Leu Met Glu Thr Glu Arg
        115                 120                 125

Glu Ile Tyr Leu Lys Arg Gln Glu Leu Asn Ser Ala Arg Asp Ser Tyr
130                 135                 140

Lys Lys Ser His Asp Pro Ala Phe Val Thr Leu Arg Asp Glu Leu Ser
145                 150                 155                 160

Lys Glu Ile Asp Ala Val Glu Glu Lys Ala Arg Gly Leu Arg Asp Arg
                165                 170                 175

Ala Cys Asn Asp Leu Tyr Glu Val Leu Arg Ser Asp Ser Glu Lys Phe
            180                 185                 190

Arg Glu Trp Leu Tyr Lys Glu Val Arg Ser Pro Glu Glu Ile Asn Asp
        195                 200                 205

His Ala Ile Lys Asp Gly Met Cys Gly Tyr Glu Leu Val Lys Arg Glu
    210                 215                 220

Leu Lys His Ala Asp Leu Leu Ile Cys Asn Tyr His His Val Leu Asn
225                 230                 235                 240

Pro Asp Ile Phe Ser Thr Val Leu Gly Trp Ile Glu Lys Glu Pro Gln
                245                 250                 255

Glu Thr Ile Val Ile Phe Asp Glu Ala His Asn Leu Glu Ser Ala Ala
            260                 265                 270

Arg Ser His Ser Ser Leu Ser Leu Thr Glu His Ser Ile Glu Lys Ala
        275                 280                 285

Ile Thr Glu Leu Glu Ala Leu Asp Leu Leu Ala Asp Asp Asn Ile
    290                 295                 300

His Asn Leu Phe Asn Ile Phe Leu Glu Val Ile Ser Asp Thr Tyr Asn
305                 310                 315                 320

Ser Arg Phe Lys Phe Gly Glu Arg Glu Arg Val Arg Lys Asn Trp Tyr
```

325                 330                 335
Asp Ile Arg Ile Ser Asp Pro Tyr Glu Arg Asn Asp Ile Val Arg Gly
                340                 345                 350
Lys Phe Leu Arg Gln Ala Lys Gly Asp Phe Gly Glu Lys Asp Asp Ile
                355                 360                 365
Gln Ile Leu Leu Ser Glu Ala Ser Glu Leu Gly Ala Lys Leu Asp Glu
                370                 375                 380
Thr Tyr Arg Asp Gln Tyr Lys Lys Gly Leu Ser Ser Val Met Lys Arg
385                 390                 395                 400
Ser His Ile Arg Tyr Val Ala Asp Phe Met Ser Ala Tyr Ile Glu Leu
                405                 410                 415
Ser His Asn Leu Asn Tyr Tyr Pro Ile Leu Asn Val Arg Arg Asp Met
                420                 425                 430
Asn Asp Glu Ile Tyr Gly Arg Val Glu Leu Phe Thr Cys Ile Pro Lys
                435                 440                 445
Asn Val Thr Glu Pro Leu Phe Asn Ser Leu Phe Ser Val Ile Leu Met
                450                 455                 460
Ser Ala Thr Leu His Pro Phe Glu Met Val Lys Lys Thr Leu Gly Ile
465                 470                 475                 480
Thr Arg Asp Thr Cys Glu Met Ser Tyr Gly Thr Ser Phe Pro Glu Glu
                485                 490                 495
Lys Arg Leu Ser Ile Ala Val Ser Ile Pro Pro Leu Phe Ala Lys Asn
                500                 505                 510
Arg Asp Asp Arg His Val Thr Glu Leu Leu Glu Gln Val Leu Leu Asp
                515                 520                 525
Ser Ile Glu Asn Ser Lys Gly Asn Val Ile Leu Phe Phe Gln Ser Ala
                530                 535                 540
Phe Glu Ala Lys Arg Tyr Tyr Ser Lys Ile Glu Pro Leu Val Asn Val
545                 550                 555                 560
Pro Val Phe Leu Asp Glu Val Gly Ile Ser Ser Gln Asp Val Arg Glu
                565                 570                 575
Glu Phe Phe Ser Ile Gly Glu Glu Asn Gly Lys Ala Val Leu Leu Ser
                580                 585                 590
Tyr Leu Trp Gly Thr Leu Ser Glu Gly Ile Asp Tyr Arg Asp Gly Arg
                595                 600                 605
Gly Arg Thr Val Ile Ile Gly Val Gly Tyr Pro Ala Leu Asn Asp
                610                 615                 620
Arg Met Asn Ala Val Glu Ser Ala Tyr Asp His Val Phe Gly Tyr Gly
625                 630                 635                 640
Ala Gly Trp Glu Phe Ala Ile Gln Val Pro Thr Ile Arg Lys Ile Arg
                645                 650                 655
Gln Ala Met Gly Arg Val Val Arg Ser Pro Thr Asp Tyr Gly Ala Arg
                660                 665                 670
Ile Leu Leu Asp Gly Arg Phe Leu Thr Asp Ser Lys Lys Arg Phe Gly
                675                 680                 685
Lys Phe Ser Val Phe Glu Val Phe Pro Pro Ala Glu Arg Ser Glu Phe
                690                 695                 700
Val Asp Val Asp Pro Glu Lys Val Lys Tyr Ser Leu Met Asn Phe Phe
705                 710                 715                 720
Met Asp Asn Asp Glu Gln
                725

<210> SEQ ID NO 11

```
<211> LENGTH: 9
<212> TYPE: PRT
<213> ORGANISM: Artificial Sequence
<220> FEATURE:
<223> OTHER INFORMATION: Motif V

<400> SEQUENCE: 11

Tyr Leu Trp Gly Thr Leu Ser Glu Gly
1               5

<210> SEQ ID NO 12
<211> LENGTH: 22
<212> TYPE: PRT
<213> ORGANISM: Artificial Sequence
<220> FEATURE:
<223> OTHER INFORMATION: Motif VI

<400> SEQUENCE: 12

Gln Ala Met Gly Arg Val Val Arg Ser Pro Thr Asp Tyr Gly Ala Arg
1               5                   10                  15

Ile Leu Leu Asp Gly Arg
            20

<210> SEQ ID NO 13
<211> LENGTH: 723
<212> TYPE: PRT
<213> ORGANISM: Halorubrum lacusprofundi

<400> SEQUENCE: 13

Met Ser Glu Ala Pro His Leu Arg Phe Phe Pro Tyr Glu Pro Tyr
1               5                   10                  15

Pro Asn Gln Arg Glu Ala Met Asp Arg Val Ala Asn Ala Leu Asp Arg
                20                  25                  30

Gly Gln Asp Val Leu Phe Glu Gly Ala Pro Gly Thr Gly Lys Thr Leu
            35                  40                  45

Ser Ala Leu Val Pro Ala Leu Glu His Ala Arg Glu His Asp Arg Thr
50                  55                  60

Val Val Ile Thr Thr Asn Val His Gln Gln Met Arg Gln Phe Val Glu
65                  70                  75                  80

Asp Ala Arg Ala Ile Thr Arg Glu Thr Pro Ile Arg Ala Val Val Phe
                85                  90                  95

Lys Gly Lys Ser Ser Met Cys His Ile Asp Val Asp Tyr Gln Glu Cys
            100                 105                 110

Gln Thr Leu Arg Asp Thr Thr Arg Glu Met Val Glu Thr Glu Ser Glu
        115                 120                 125

Val Arg Glu Leu Glu Thr Arg Gln Arg Glu Leu Leu Ala Glu Ser Arg
130                 135                 140

Glu Gly Asp Ala Gly Ala Ala Glu Ala Arg Glu Ser Val Met Asp Glu
145                 150                 155                 160

Leu Asp Glu Leu Glu Ala Asp Ile Asp Glu Tyr Asp Ala Ala Asn Val
                165                 170                 175

Cys Ala His Tyr Arg Asn Asn Leu Val Glu Asp Thr Asp Glu Phe Phe
            180                 185                 190

Gly Trp Leu Phe Glu Asp Val Arg Thr Pro Gly Asp Val Tyr Ala Tyr
        195                 200                 205

Ala Asp Glu Arg Glu Leu Cys Gly Tyr Glu Leu Leu Lys Glu Gly Met
    210                 215                 220

Glu Gly Val Asp Leu Val Val Cys Asn Tyr His His Leu Leu Asp Pro
225                 230                 235                 240
```

```
Asn Ile Arg Glu Gln Phe Phe Arg Trp Ile Asp Arg Asp Pro Ser Glu
                245                 250                 255
Ile Ile Thr Val Phe Asp Glu Ala His Asn Val Glu Asp Ala Ala Arg
            260                 265                 270
Asp His Ala Thr Arg Thr Leu Thr Glu Asn Thr Leu Asp Ala Ala Leu
        275                 280                 285
Asp Glu Leu Thr Glu Ser Asp Asp Ser Arg Ala Glu Ala Ala Glu Asn
290                 295                 300
Val Val Arg Ala Phe Arg Asp Ala Leu Val Glu Thr Arg Asp Asp Ala
305                 310                 315                 320
Leu Gly Val Gly Lys His Glu Ser Ile Gly Asn Trp Glu Asp Ile
                325                 330                 335
Ser Ile Ala Asn Asp Asp Arg Arg Asp Asp Leu Thr Leu Ala Phe Leu
            340                 345                 350
Arg Asn Tyr Glu Gly Lys Gly Ile Asp Thr Glu Thr Glu Leu Ala Val
        355                 360                 365
Gln Leu Gly Gln Ala Leu Asp Glu Glu Tyr Glu Arg Arg Tyr Arg Asp
    370                 375                 380
Gly Glu Thr Thr Thr Arg Thr Glu Cys Gln Ile Leu Gln Ala Ala Arg
385                 390                 395                 400
Phe Val Ser Thr Trp Met Glu Glu Gly Thr Glu Leu Gly Gln Tyr Pro
                405                 410                 415
Val Val Ser Val Arg Arg Asp Gly Ala Thr Glu Glu Val Tyr Gly Arg
            420                 425                 430
Ala Glu Leu Tyr Thr Cys Ile Pro Arg Arg Val Thr Glu Glu Leu Phe
        435                 440                 445
Asp Glu Val Ala Ala Ser Val Leu Met Ser Ala Thr Leu Arg Pro Phe
    450                 455                 460
Asp Val Thr Lys Asp Val Leu Gly Leu Glu Asp Val Ala Ser Leu Ala
465                 470                 475                 480
Tyr Gly Met Gly Tyr Pro Glu Glu Asn Arg Arg Thr Phe Ala Val Asp
                485                 490                 495
Thr Pro Pro Leu Phe Ala Ser Glu Arg Asn Asp Pro Gly Thr Gln Glu
            500                 505                 510
Thr Val Ala Ser Leu Leu Arg Asp Ala Ile Arg Phe Thr Pro Gly Asn
        515                 520                 525
Thr Leu Ala Phe Phe Pro Ser Tyr Ala Glu Ala Glu Arg Tyr Tyr Glu
    530                 535                 540
Arg Leu Gly Gly Ala Asp Leu Gly Ser Leu Tyr Leu Asp Gly Pro Gly
545                 550                 555                 560
Glu Asp Glu Glu Lys Leu Arg Arg Arg Phe Val Glu Ser Asp Asp Ala
                565                 570                 575
Thr Leu Phe Thr Ser Leu Trp Gly Thr Leu Ala Glu Gly Val Ser Phe
            580                 585                 590
Asp Gly Asp Asp Ala Arg Thr Val Val Val Gly Val Pro Tyr Pro
        595                 600                 605
His Leu Ser Asp Arg Met Glu Ala Val Gln Asp Ala Tyr Asn Arg Val
    610                 615                 620
Phe Ala Asp Arg Asp Arg Ser Arg Asp Pro Gly Trp Ala Tyr Ala Val
625                 630                 635                 640
Glu Ile Pro Thr Ile Arg Lys Thr Arg Gln Ala Ile Gly Arg Val Val
                645                 650                 655
```

```
Arg Gly Pro Asp Asp Phe Gly Val Arg Ile Leu Ala Asp Arg Arg Tyr
            660                 665                 670

Thr Ser Ala Asp Met Gly Lys Tyr Ser Val Arg Gly Ala Phe Pro Pro
        675                 680                 685

Glu Glu Arg Glu Glu Leu Leu Asp Leu Asp Pro Glu Lys Leu Lys Phe
690                 695                 700

Ala Met Leu Asn Phe Tyr Gly Asp His Asp Ala Tyr Asp Gly Ala Pro
705                 710                 715                 720

Pro Glu Pro

<210> SEQ ID NO 14
<211> LENGTH: 9
<212> TYPE: PRT
<213> ORGANISM: Artificial Sequence
<220> FEATURE:
<223> OTHER INFORMATION: Motif V

<400> SEQUENCE: 14

Ser Leu Trp Gly Thr Leu Ala Glu Gly
1               5

<210> SEQ ID NO 15
<211> LENGTH: 22
<212> TYPE: PRT
<213> ORGANISM: Artificial Sequence
<220> FEATURE:
<223> OTHER INFORMATION: Motif VI

<400> SEQUENCE: 15

Gln Ala Ile Gly Arg Val Val Arg Gly Pro Asp Phe Gly Val Arg
1               5                   10                  15

Ile Leu Ala Asp Arg Arg
            20

<210> SEQ ID NO 16
<211> LENGTH: 802
<212> TYPE: PRT
<213> ORGANISM: Methanosarcina acetivorans

<400> SEQUENCE: 16

Met Asn Phe Gly Asp Lys Asn Arg Val Lys Arg Met Glu Gln Lys Asn
1               5                   10                  15

Gly Tyr Met Arg Tyr Phe Thr Lys Lys Ser Cys Tyr Pro Asn Gln Gly
            20                  25                  30

Glu Ala Met Glu Lys Ile His Ser Ala Leu Leu Asn Gln Lys Ile Val
        35                  40                  45

Leu Phe Glu Gly Ala Cys Gly Thr Gly Lys Thr Leu Ser Ser Leu Ala
    50                  55                  60

Pro Ala Leu His Val Gly Arg Lys Leu Asn Lys Val Val Ile Ile Val
65                  70                  75                  80

Thr Asn Val His Gln Gln Met Val Gln Phe Ile His Glu Ala Arg Asp
                85                  90                  95

Ile Asn Arg Asp Asn Ser Ile Lys Thr Ile Val Phe Lys Gly Lys Thr
            100                 105                 110

Ser Met Cys Pro Asp Asn Leu Asp Tyr Glu Glu Cys Arg Leu Lys Gly
        115                 120                 125

Glu Asn Thr Tyr Asp Leu Leu Asp Phe Glu Arg Glu Val Ser Ser Lys
    130                 135                 140

Glu Lys Glu Leu Lys Asp Ala Tyr Glu Lys Tyr Lys Arg Thr Lys Asp
```

```
                145                 150                 155                 160
Pro Ala Leu Tyr Ala Leu Arg Asn Glu Leu Glu Lys Glu Leu Glu Glu
                    165                 170                 175

Ala Arg Lys Lys Ala Gln Gly Leu Arg Ser His Ser Cys Ser Lys Leu
            180                 185                 190

Tyr Glu Val Leu Arg Phe Glu Gly Asn Glu Phe Ser Ser Trp Leu Phe
                195                 200                 205

Ser Asp Val Arg Ser Pro Glu Glu Ile Met Glu Tyr Ala Glu Asp Arg
            210                 215                 220

Gly Met Cys Gly Tyr Glu Leu Leu Lys Lys Glu Leu Lys Asn Thr Glu
225                 230                 235                 240

Leu Leu Ile Cys Asn Phe His His Val Leu Asn Ala Asp Ile Phe Met
                245                 250                 255

Thr Leu Leu Lys Trp Leu Glu Arg Asp Pro Glu Asp Ile Ile Leu Ile
                260                 265                 270

Phe Asp Glu Ala His Asn Ile Glu Ala Ser Ala Arg Ser His Ser Ser
            275                 280                 285

Val Met Leu Ser Glu Leu Thr Ile Glu Lys Ala Leu Ser Glu Val Gly
            290                 295                 300

Glu Ile Pro Glu Pro Asp Ser Ser Pro Val Phe Gly Thr Arg Thr Gly
305                 310                 315                 320

Val Ser Gly Thr Gly Ser Gly Ser Gly Pro Gly Ile Pro Leu Asp Gln
                325                 330                 335

Asp Tyr Ala Ser Arg Leu Tyr Ala Lys Arg Leu Phe Ser Cys Leu Leu
            340                 345                 350

Asn Ala Val Arg Glu Thr Tyr Asp Ser Lys Leu Lys Phe Gly Glu Arg
            355                 360                 365

Asn Arg Leu Gly Lys His Trp Gln Asp Ile Gln Ile Ser Asp Pro Tyr
            370                 375                 380

Glu Arg Leu Asp Ile Leu Lys Ala Arg Phe Leu Arg Asp Ala Lys Lys
385                 390                 395                 400

Glu Gly Phe Ala Asp Glu Glu Lys Val Leu Thr Arg Leu Arg Glu Ile
                405                 410                 415

Gly Glu Phe Gly Gly Arg Leu Glu Asp Ile Tyr Ala Glu Asn Tyr Lys
                420                 425                 430

Lys Gly Leu Leu Pro Val Pro Lys Arg Ser Gln Ile Arg Tyr Val Ala
            435                 440                 445

Asp Phe Leu Ser Ser Tyr Leu Val Leu Ser Asp Arg Gln Asn Tyr Tyr
450                 455                 460

Pro Ile Leu Asn Met Arg Arg Asp Phe Lys Ser Asp Arg Val Val Gly
465                 470                 475                 480

Arg Leu Glu Leu Phe Thr Cys Ile Pro Lys Asn Val Thr Gln Pro Leu
                485                 490                 495

Leu Asp Ser Val Tyr Ser Ala Val Leu Met Ser Ala Thr Leu Arg Pro
            500                 505                 510

Phe Glu Met Ile Lys Ser Thr Leu Gly Ile Thr Arg Glu Val Glu Glu
            515                 520                 525

Ile Ile Tyr Gly Ile Thr Phe Pro Lys Glu Arg Arg Leu Thr Leu Ala
            530                 535                 540

Val Ser Val Pro Pro Leu Phe Ala Lys Asn Arg Asp Ser Pro Glu Thr
545                 550                 555                 560

Leu Glu Ser Leu Lys Glu Ser Leu Leu Ala Ala Thr Ala Ala Ser Pro
            565                 570                 575
```

-continued

```
Gly Asn Val Ile Ile Tyr Phe Gln Ser Tyr Ala Glu Ala Leu Arg Tyr
            580                 585                 590

Thr Lys Leu Leu Glu Pro Glu Leu Ser Val Pro Val Phe Leu Asp Glu
        595                 600                 605

Ile Gly Val Ser Ala Gln Glu Ile Arg Gln Lys Phe Phe Lys Lys Gly
610                 615                 620

Glu Gln Gly Gly Lys Ala Val Leu Ile Thr Tyr Leu Trp Gly Thr Leu
625                 630                 635                 640

Ser Glu Gly Val Asp Phe Arg Asp Ser Arg Gly Arg Thr Val Ile Val
                645                 650                 655

Val Gly Val Gly Tyr Pro Ala Leu Asn Asp Arg Ile Lys Ala Val Glu
            660                 665                 670

Ser Ala Tyr Asp Thr Val Phe Gly Cys Gly Glu Gly Trp Glu Phe Ala
        675                 680                 685

Val Gln Val Pro Thr Ile Arg Lys Val Arg Gln Ala Met Gly Arg Val
690                 695                 700

Val Arg Ser Pro Gly Asp Phe Gly Val Arg Ile Leu Leu Asp Ala Arg
705                 710                 715                 720

Tyr Gln Gly Ser Gln Ala Arg Lys Leu Gly Lys Phe Ser Val Phe Gly
                725                 730                 735

Tyr Phe Pro Pro Glu Glu Ser Lys Glu Phe Leu Asp Val Ala Pro Arg
            740                 745                 750

Asp Val Gly Ser Leu Val Glu Glu Phe Phe Ala Asn Ile Val Pro Tyr
        755                 760                 765

Ser Pro Glu Lys Lys Asp His Gly Asn Lys Glu Asn Glu Lys Lys Gly
770                 775                 780

Leu Lys Ser Pro Ala Ser Gly Arg Leu Glu Phe Gly Ser Leu Ala Glu
785                 790                 795                 800

Lys Leu

<210> SEQ ID NO 17
<211> LENGTH: 22
<212> TYPE: PRT
<213> ORGANISM: Artificial Sequence
<220> FEATURE:
<223> OTHER INFORMATION: Motif VI

<400> SEQUENCE: 17

Gln Ala Met Gly Arg Val Val Arg Ser Pro Gly Asp Phe Gly Val Arg
1               5                   10                  15

Ile Leu Leu Asp Ala Arg
            20

<210> SEQ ID NO 18
<211> LENGTH: 726
<212> TYPE: PRT
<213> ORGANISM: Methanosalsum zhilinae

<400> SEQUENCE: 18

Met Ala Gln Arg Gly Gly Tyr Leu Lys Tyr Phe Pro Lys Ser Ser Cys
1               5                   10                  15

Tyr Pro Asn Gln Lys Asp Ala Met Asp Arg Ile Tyr Ser Ala Leu Leu
            20                  25                  30

Glu Lys Glu Ile Val Leu Phe Glu Gly Ala Cys Gly Thr Gly Lys Thr
        35                  40                  45

Leu Ser Ala Leu Ala Pro Ala Leu His Val Gly Arg Gln Gln Asp Lys
```

```
                 50                  55                  60
Thr Val Ile Ile Ala Thr Asn Val His Gln Gln Met Val Gln Phe Val
 65                  70                  75                  80

Asn Glu Ala Arg Glu Ile Lys Lys Asn Asn Asp Ile Arg Val Ala Val
                     85                  90                  95

Val Lys Gly Lys Ala Ala Val Cys Pro His Glu Leu Asp Tyr Glu Glu
                100                 105                 110

Cys Asn Leu Arg Arg Glu Asn Thr Phe Glu Val Leu Glu Leu Glu Lys
                115                 120                 125

Glu Ile Gln Leu Lys Lys Gln Glu Ile Lys Ser Ala Ser Gln Asn Tyr
                130                 135                 140

Lys Glu Ser Arg Asp Pro Ser Met Val Ser Leu Arg Asp Glu Leu Val
145                 150                 155                 160

Lys Glu Leu Asp Ala Ala Gln Glu Lys Ala Arg Thr Val Arg Asn Arg
                165                 170                 175

Ser Cys Asn Glu Leu Tyr Glu Val Leu Arg Tyr Asp Ser Glu Met Phe
                180                 185                 190

Arg Asn Trp Leu Phe Asp Asp Val Arg Thr Pro Glu Glu Val Asn Asp
                195                 200                 205

Phe Ala Phe Gly Lys Gly Met Cys Gly Tyr Glu Leu Leu Lys Arg Glu
210                 215                 220

Leu Lys Tyr Ala Asp Leu Val Ile Cys Asn Phe His His Ile Leu Asn
225                 230                 235                 240

Gly Asp Ile Phe Ser Thr Leu Leu Gly Trp Leu Glu Lys Glu Pro Gly
                245                 250                 255

Asp Val Ile Val Ile Phe Asp Glu Ala His Asn Ile Glu Ser Ser Ala
                260                 265                 270

Arg Ser His Ser Ser Ile Thr Leu Thr Glu His Thr Val Glu Lys Thr
                275                 280                 285

Ile Ser Glu Ile Asp Ala Asn Ser Asp Gln Ile Pro Glu Glu Gly Leu
                290                 295                 300

His Asn Leu Phe Ser Leu Leu Ser Thr Ile Gln Asp Thr Tyr Asn
305                 310                 315                 320

Ser Arg Phe Arg Phe Gly Glu Arg Glu Arg Val Gly Arg Arg Trp Tyr
                325                 330                 335

Asp Ile Arg Ile Ser Asp Pro Tyr Glu Arg Asn Asp Ile Ile Arg Ala
                340                 345                 350

Arg Phe Leu Arg Ser Ala Arg Glu Asn Gly Phe Ala Asp Glu Lys Ser
                355                 360                 365

Ile Gln Glu Leu Leu Ala Thr Ala Val Glu Phe Gly Ser Gln Leu Asp
                370                 375                 380

Glu Thr Tyr Arg Asp Gln Tyr Lys Lys Gly Leu Thr Thr Val Leu Lys
385                 390                 395                 400

Arg Ser His Ile His Gln Thr Ala Ala Phe Leu Ser Ser Tyr Leu Tyr
                405                 410                 415

Leu Ser Asn Asn Pro Asn Tyr Tyr Pro Val Leu Asn Val Arg Arg Asp
                420                 425                 430

Ser Asn Asn Glu Ile Tyr Gly Arg Leu Glu Leu Phe Thr Cys Ile Pro
                435                 440                 445

Lys Asn Val Thr Gln Pro Leu Phe Glu Ser Leu Tyr Ser Ala Ile Leu
                450                 455                 460

Met Ser Ala Thr Leu Arg Pro Phe Asn Met Val Lys Thr Cys Gly
465                 470                 475                 480
```

```
Ile Asn Arg Asn Thr Cys Glu Ile Ala Tyr Ala Thr Ser Phe Pro Leu
                485                 490                 495

Glu Lys Arg Leu Thr Ile Ala Val Ser Ile Pro Pro Leu Phe Ser Lys
            500                 505                 510

Asn Arg Asp Asp Ile Gln Ala Ser Glu Ala Ile Glu Lys Gly Leu Leu
            515                 520                 525

Asp Ser Ile Glu Tyr Ser Ala Gly Asn Val Ile Phe Phe Gln Asn
            530                 535                 540

Ser Phe Glu Ala Ala Arg Tyr Tyr Glu Lys Ile Gln Ser Lys Met Glu
545                 550                 555                 560

Asp Ile Pro Val Phe Leu Asp Glu Val Gly Val Ser Ala Gln Asn Val
                565                 570                 575

Arg Thr Glu Phe Phe Arg Ile Gly Glu Ser Gly Glu Lys Ala Val Leu
                580                 585                 590

Ile Ser Tyr Leu Trp Gly Thr Leu Ser Glu Gly Ile Asp Tyr Arg Asp
                595                 600                 605

Glu Arg Ala Arg Thr Val Val Ile Val Gly Val Gly Tyr Pro Gly Leu
                610                 615                 620

Asp Asp Arg Met Arg Ala Val Glu Ser Ala Tyr Asp His Ala Phe Gly
625                 630                 635                 640

Tyr Gly Ser Gly Trp Glu Tyr Ala Val Gln Ile Pro Thr Ile Arg Lys
                645                 650                 655

Ile Arg Gln Ala Met Gly Arg Val Val Arg Ser Pro Ser Asp Tyr Gly
                660                 665                 670

Ala Arg Ile Leu Leu Asp Gly Arg Phe Leu Thr Asp Ser Lys Lys Arg
                675                 680                 685

Phe Gly Lys Phe Ser Val Phe Lys Glu Phe Pro Pro Glu Gln Lys
                690                 695                 700

Glu Ile Val Asp Val Glu Leu Asp Lys Met Lys Asn Ser Leu Met Asn
705                 710                 715                 720

Phe Phe Met Glu Asn Gly
                725

<210> SEQ ID NO 19
<211> LENGTH: 22
<212> TYPE: PRT
<213> ORGANISM: Artificial Sequence
<220> FEATURE:
<223> OTHER INFORMATION: Motif VI

<400> SEQUENCE: 19

Gln Ala Met Gly Arg Val Val Arg Ser Pro Ser Asp Tyr Gly Ala Arg
1               5                   10                  15

Ile Leu Leu Asp Gly Arg
            20

<210> SEQ ID NO 20
<211> LENGTH: 722
<212> TYPE: PRT
<213> ORGANISM: Natronomonas pharaonis

<400> SEQUENCE: 20

Met Ser Arg Ser Asp Gly Ser Arg Gln Phe Phe Pro Tyr Asp Gln Pro
1               5                   10                  15

Tyr Asp His Gln Ser Asp Ala Met Glu Arg Ile Arg Glu Ala Leu Val
            20                  25                  30
```

Glu Glu Arg Asp Val Leu Phe Glu Gly Ala Cys Gly Thr Gly Lys Thr
            35                  40                  45

Leu Ala Ala Leu Val Pro Ala Leu Glu Tyr Ala Arg Ala Ala Gly Lys
 50                  55                  60

Thr Val Val Ile Thr Thr Asn Val His Gln Gln Thr Arg Gln Phe Ile
 65                  70                  75                  80

Glu Glu Ala Arg Ala Ile Asn Glu Gln Thr Pro Ile Arg Ser Val Val
                85                  90                  95

Phe Arg Gly Lys Ala Ser Met Cys His Ile Asp Val Gly Tyr Glu Glu
            100                 105                 110

Cys Gln Ala Leu Arg Asp Thr Thr Arg Glu Leu Val Glu Thr Glu Gln
            115                 120                 125

Asp Ile Ala Glu Leu Glu Ala Arg Glu Ser Glu Leu Arg Asp Ala Ser
        130                 135                 140

Lys Ala Gly Asp Gly Asp Ala Ala Glu Ala Arg Gly Thr Val Leu Asp
145                 150                 155                 160

Glu Leu Asp Glu Leu Glu Ala Ser Ala Glu Ala Leu Arg Glu Glu Arg
                165                 170                 175

Asn Val Cys Asp Arg Tyr Tyr Lys Asn Leu Thr Gly Glu Thr Asp Glu
            180                 185                 190

Phe Tyr Gln Trp Leu Tyr Glu Asp Val Arg Thr Pro Glu Glu Ile Tyr
        195                 200                 205

Glu Tyr Ala Asp Arg Gln Gly Leu Cys Gly Tyr Glu Leu Leu Lys Asp
            210                 215                 220

Gly Ile Glu Gly Ile Asp Leu Val Ile Cys Asn Tyr His His Leu Leu
225                 230                 235                 240

Asp Pro Met Ile Arg Glu Gln Phe Phe Arg Trp Leu Gly Arg Asp Pro
                245                 250                 255

Glu Asp Val Ile Ala Val Phe Asp Glu Ala His Asn Val Ala Asp Ala
            260                 265                 270

Ala Arg Asp His Ala Arg Arg Thr Leu Ala Glu Arg Thr Leu Asp Gly
        275                 280                 285

Ala Leu Asp Glu Leu Glu Asp Val Ser Asp Ala Arg Ala Asp Ala Ala
290                 295                 300

Ala Asn Val Val Gly Ala Phe Lys Asp Ala Leu Val Glu Thr Tyr Glu
305                 310                 315                 320

Ser Ser Phe Gly Tyr Gly Asp Arg Glu Ala Val Gly Glu Glu Trp Glu
                325                 330                 335

Asp Val Pro Val Asp Ser Glu Ser Gly Arg Asp Asp Leu Ser Val Ala
            340                 345                 350

Phe Leu Glu Ala Tyr Thr Gly Gln Gly Phe Glu Thr Asp Leu Glu Ser
        355                 360                 365

Ala Leu Ser Leu Gly Glu Glu Leu Asp Arg Arg Tyr Glu Gln Glu Tyr
370                 375                 380

Lys Asp Gly Glu Thr Thr Thr Arg Lys Glu Cys Pro Thr Leu Thr Ala
385                 390                 395                 400

Ala Ala Phe Ile Glu Thr Trp Met Asp Ala Ser Val Glu Pro Gly Glu
                405                 410                 415

Tyr Pro Val Val Gly Val Arg Arg Ser Glu Thr Gly Ile Val Gly Arg
            420                 425                 430

Ala Glu Leu Tyr Thr Cys Leu Pro Arg Arg Val Thr Glu Pro Leu Phe
        435                 440                 445

Glu Glu Leu His Gly Thr Val Leu Met Ser Ala Thr Leu Arg Pro Phe

-continued

```
                450                 455                 460
Asp Val Thr Glu Asp Val Leu Gly Leu Glu Glu Pro Leu Thr Met Ala
465                 470                 475                 480

Tyr Gly Glu Gln Phe Pro Asp Glu Arg Arg Thr Tyr Ala Val Glu
                485                 490                 495

Thr Pro Ala Leu Phe Ala Ser Lys Arg Asp Pro Gln Val Gln Glu
                500                 505                 510

Thr Val Gly Asn Val Ile Ala Glu Thr Val Ala Phe Thr Pro Gly Asn
                515                 520                 525

Thr Leu Ala Phe Phe Pro Ser Tyr Ala Glu Ala Glu Arg Tyr Tyr His
                530                 535                 540

Arg Tyr Ala Gly Glu Ala Thr Pro Tyr Leu Asp Glu Pro Gly Val Glu
545                 550                 555                 560

Ala Glu Ser Leu Arg Gln Ser Phe Ile Glu Asp Gln Ala Val Leu
                565                 570                 575

Phe Thr Ser Leu Trp Gly Thr Leu Ala Glu Gly Val Ser Phe Asp Gly
                580                 585                 590

Asp Asp Ala Arg Ser Val Leu Val Gly Val Pro Tyr Pro His Leu
                595                 600                 605

Asp Glu Arg Met Glu Ala Val Gln Gly Ala Tyr Asp Gly Ala Phe Gly
                610                 615                 620

Asp Gly Thr Asp Asp Ala Gly Trp Arg Tyr Ala Val Glu Ile Pro Thr
625                 630                 635                 640

Val Arg Lys Thr Arg Gln Ala Leu Gly Arg Val Val Arg Ser Pro Thr
                645                 650                 655

Asp Phe Gly Val Arg Val Leu Val Asp Glu Arg Tyr Thr Gln Ser Lys
                660                 665                 670

Arg Ala Asp Leu Gly Glu Tyr Ser Val Tyr Pro Glu Phe Pro Pro Glu
                675                 680                 685

Glu Arg Asn Glu His Ile Asp Ile Gly Pro Glu Lys Leu Lys Phe Ala
                690                 695                 700

Met Leu Asn Phe Tyr Ser Asp Met Asp Ala Trp Asp Gly Asp Pro Pro
705                 710                 715                 720

Thr Pro

<210> SEQ ID NO 21
<211> LENGTH: 22
<212> TYPE: PRT
<213> ORGANISM: Artificial Sequence
<220> FEATURE:
<223> OTHER INFORMATION: Motif VI

<400> SEQUENCE: 21

Gln Ala Leu Gly Arg Val Val Arg Ser Pro Thr Asp Phe Gly Val Arg
1               5                   10                  15

Val Leu Val Asp Glu Arg
                20

<210> SEQ ID NO 22
<211> LENGTH: 647
<212> TYPE: PRT
<213> ORGANISM: Haliangium ochraceum

<400> SEQUENCE: 22

Met Ser Asp Tyr Ile Asp Thr Val Phe Gly Pro Asp Gly Leu Leu Ala
1               5                   10                  15
```

-continued

```
Asp Arg Phe Pro Ala Tyr Ala Pro Arg Pro Gly Gln Ile Ser Leu Ala
             20                  25                  30
Arg Ala Val Asp Ala Ala Ile Ala Asp Gly Ala His Leu Leu Ala Glu
         35                  40                  45
Ala Pro Thr Gly Cys Gly Lys Gly Ile Gly Tyr Ala Val Pro Ala Ser
     50                  55                  60
Tyr His Ala Ala His Asn Gly Leu Arg Val Val Leu Ala Thr Ser Ser
 65                  70                  75                  80
Ile Asn Leu Gln Glu Gln Leu Val Thr Thr Asp Leu Pro Leu Leu Glu
                 85                  90                  95
Ser Ile Leu Pro Trp Pro Val Arg Phe Ala Leu Leu Lys Gly Lys Arg
             100                 105                 110
Asn Tyr Leu Cys Leu Ser Arg Leu Tyr Glu Gly Ser Ala Arg Ser Asp
         115                 120                 125
Phe Ala Thr Pro Ser Asp His Glu Met Arg Ser Asp Ile Arg Ala Trp
    130                 135                 140
Ala Ala Leu Thr Glu Thr Gly Asp Lys Ser Glu Leu Ser Phe Glu Pro
145                 150                 155                 160
Pro Asp Arg Val Trp Asn Asp Phe Ser Thr Ser Ala Glu Glu Cys Lys
                165                 170                 175
Gly Ser Glu Cys Arg Phe His Asp Ala Cys Phe Ala Val Lys Ala Arg
            180                 185                 190
Ala Ala Ala Glu Glu Ala Asp Ile Val Val Ser Asn Tyr His Leu Leu
        195                 200                 205
Gly Val His Leu Gln Leu Arg Glu Ala Thr Gly Arg Asn Leu Val Leu
    210                 215                 220
Pro Lys Phe Asp Val Ala Val Cys Asp Glu Gly His Lys Leu Ala Asp
225                 230                 235                 240
Ile Ala Arg Asp Phe Phe Gly Phe Arg Val Thr Leu Gly Ser Leu Arg
                245                 250                 255
Trp Leu Ala Ala Arg Leu Lys Arg Leu Gly Ala Asp Arg Leu Ser Lys
            260                 265                 270
Leu Leu His Ala Asp Gly Ser Ala Phe Phe Glu Ala Leu Gln Gly Tyr
        275                 280                 285
Gln Arg Ser Gly Ala Tyr Thr Cys Arg Leu Arg Glu Leu Glu Pro Val
    290                 295                 300
Arg Trp Leu Pro Leu His Tyr Thr Leu Arg Glu Ile Ile Asp His Tyr
305                 310                 315                 320
Glu His Ala Leu Ala Ile Ala Pro Pro Leu Asn Asp Leu Asp Pro Asp
                325                 330                 335
Leu Arg Ala Glu Glu Arg Asp Arg Arg Ala Thr Leu Glu Arg Thr Leu
            340                 345                 350
Ser Arg Ala Ser Thr Leu Ala Gln Asn Leu Thr Ala Ala Met Glu Leu
        355                 360                 365
Glu Asp Lys Gly Cys Val Tyr Tyr Leu Glu Glu Leu Pro Lys Gly Gly
    370                 375                 380
Val Ala Val Cys Cys Lys Ala Ile Asp Val Ser Glu Arg Leu Gln Asp
385                 390                 395                 400
Ser Leu Phe Ala Lys Thr Gln Ser Thr Ile Val Thr Ser Ala Thr Leu
                405                 410                 415
Thr Ala Gly Asp Ser Phe Asp Tyr Val Arg Lys Asp Leu Gly Val Gln
            420                 425                 430
Ser Pro Arg Glu Leu Val Val Asp Ser Pro Phe Asp Phe Arg Lys Gln
```

```
                435                 440                 445
Val Leu Phe Ile Val Pro Asp Cys Val Ile Asp Pro Arg Gly Pro Gly
    450                 455                 460

Phe Pro Thr Cys Val Ala Trp Thr Val Glu Gln Ala Val Arg Leu Ala
465                 470                 475                 480

Gly Gly Arg Thr Leu Gly Leu Phe Thr Ser Tyr Arg Asn Leu Asp Thr
                485                 490                 495

Ala Tyr Ala Arg Ile Ala Asp Cys Gly Tyr Arg Val Leu Arg Gln Gly
            500                 505                 510

Asp Lys Pro Arg Thr Gln Leu Val Asp Glu Phe Arg Arg Asp Val Lys
        515                 520                 525

Ser Val Leu Leu Gly Thr Glu Ser Phe Trp Ala Gly Val Asp Val Gln
530                 535                 540

Gly Glu Ala Leu Ser Cys Val Val Ile Asp Arg Leu Pro Phe Pro Pro
545                 550                 555                 560

Pro Asn Asp Pro Val Ile Asp Ala Leu Lys Glu Arg Gly Gly Asn Ser
                565                 570                 575

Phe Leu Ser Ala Ser Leu Pro Arg Ala Ile Ala Phe Lys Gln Gly
            580                 585                 590

Phe Gly Arg Leu Ile Arg Ala Ser Asp Arg Gly Val Val Val
        595                 600                 605

Leu Asp Glu Arg Leu Tyr Thr Thr Phe Tyr Gly Arg Ala Phe Leu Arg
610                 615                 620

Ser Leu Pro Ala Met Arg Lys Ser Arg Thr Leu Glu Asp Val Gln Thr
625                 630                 635                 640

Phe Leu Ala Glu Thr Pro Ala
                645

<210> SEQ ID NO 23
<211> LENGTH: 9
<212> TYPE: PRT
<213> ORGANISM: Artificial Sequence
<220> FEATURE:
<223> OTHER INFORMATION: Motif V

<400> SEQUENCE: 23

Val Thr Gly Gly Val Phe Ala Glu Gly
1               5

<210> SEQ ID NO 24
<211> LENGTH: 22
<212> TYPE: PRT
<213> ORGANISM: Artificial Sequence
<220> FEATURE:
<223> OTHER INFORMATION: Motif VI

<400> SEQUENCE: 24

Gln Ala Ala Gly Arg Val Leu Arg Thr Pro Glu Asp Arg Gly Val Ile
1               5                   10                  15

Ala Leu Leu Gly Arg Arg
            20

<210> SEQ ID NO 25
<211> LENGTH: 644
<212> TYPE: PRT
<213> ORGANISM: Shewanella benthica

<400> SEQUENCE: 25

Met Asn Ala Leu Ser Ser Arg Leu Thr Ile Asp Ser Glu Gln Ala Phe
```

-continued

```
1               5                   10                  15
Ala Ala Asp Gly Val Leu Ala Arg His Ile Asn Gly Tyr Ser Thr Arg
            20                  25                  30
Val Val Gln Lys Gln Met Ala Ser Ala Val Ser Cys Ala Ile Gly Gly
            35                  40                  45
Lys Ser Asn Leu Val Ile Glu Ala Gly Thr Gly Val Gly Lys Thr Tyr
            50                  55                  60
Ala Tyr Leu Ile Pro Ala Leu Leu Ser Gly Lys Gln Val Ile Ile Ser
65                  70                  75                  80
Thr Gly Ser Lys Asn Leu Gln Glu Gln Leu Phe Tyr Lys Asp Leu Pro
                85                  90                  95
Ala Leu Leu Asp Met Leu Ala Leu Ala Pro Lys Leu Ala Leu Leu Lys
                100                 105                 110
Gly Arg Ser Asn Tyr Leu Cys Gln Leu Leu Asp Lys Gln Leu Glu
                115                 120                 125
Ala Cys Glu Ser His Glu Pro Lys Val Leu Asp Asp Leu Leu Arg Ile
                130                 135                 140
Asn Gln Trp Ala Gly Gln Thr Ala Asp Gly Asp Leu Gly Gly Leu Thr
145                 150                 155                 160
Ser Val Ser Glu Asn Ser Glu Ala Leu Trp Leu Ile Ala Ser Gln Arg
                165                 170                 175
Asp Lys Cys Thr Gly Lys Lys Cys Val His Tyr Glu Thr Cys Phe Thr
                180                 185                 190
Arg Lys Ala Arg Val Arg Ala Met Asp Ala Lys Ile Ile Val Val Asn
                195                 200                 205
His His Leu Phe Phe Ala Asp Arg Ile Leu Lys Glu Thr Gly Phe Ala
                210                 215                 220
Glu Leu Leu Pro Asp Ala Asp Val Val Ile Phe Asp Glu Ala His Leu
225                 230                 235                 240
Leu Pro Asp Ile Ala Val Ile Tyr Phe Gly Gln Gln Ile Ser Thr Arg
                245                 250                 255
Ser Leu Asp Ser Leu Leu Gly Gln Ile Val Thr Val Tyr Arg Thr Glu
                260                 265                 270
Leu Arg Asp Ser Ala Gln Ile Glu Gln Leu Ala Ser Arg Cys Ile Ser
                275                 280                 285
Arg Leu Asn Gly Trp His Gln Gln Met Tyr Asp Val Phe Glu Thr Asp
                290                 295                 300
Trp Arg Leu Leu Met Gly Asn Lys Asn Ile Ala Ser Ala Ser Trp Ala
305                 310                 315                 320
Ile Ile Ala Glu Leu Gln Ala Leu Glu Ser Leu Leu Cys Ala His Ile
                325                 330                 335
Gly Arg Ser Glu Thr Leu Asp Glu Cys Thr Glu Lys Leu Val Thr Phe
                340                 345                 350
Ser Ser Lys Met Gly Val Phe Phe Gln Cys Glu Asn Asn Gln Ala Ala
                355                 360                 365
Tyr Ser Ile Asp Tyr Gly His Arg Tyr Leu Thr Leu Ser Ile Ala Pro
                370                 375                 380
Ile Asn Val Ala Lys Glu Cys Glu Lys Leu Phe Asp Ala Gln Thr Ser
385                 390                 395                 400
Trp Ile Phe Thr Ser Ala Thr Leu Gln Ile Asn Arg Asp Leu Ser Leu
                405                 410                 415
Phe Thr Lys Gly Leu Gly Ile Asp Lys Ser Gln Lys Ile Ile Leu Asp
                420                 425                 430
```

-continued

```
Ser Pro Phe Asp Tyr Arg Ser Asn Ala Leu Leu Cys Val Pro Arg His
        435                 440                 445
Leu Ser Lys Val Ser Asn His Glu Ala Ala Val Arg Asp Leu Val Asp
    450                 455                 460
Val Ser Val Lys Ala Ile Asn Ala Ala Lys Gly Arg Thr Phe Ile Leu
465                 470                 475                 480
Phe Thr Ser His Arg Met Met Asn Ala Val Ala Ala Arg Leu Gln Ser
                485                 490                 495
Arg Val Asn Tyr Pro Leu Leu Val Gln Gly Gln Gly Ser Lys Gln Ser
            500                 505                 510
Leu Met Lys Lys Phe Arg Gln Leu Gly Asn Ala Val Leu Leu Gly Thr
        515                 520                 525
Gly Ala Phe Trp Glu Gly Val Asp Val Arg Gly Arg Leu Leu Ser Cys
    530                 535                 540
Val Ile Ile Asp Lys Leu Pro Phe Val Ser Pro Ser Asp Thr Leu Tyr
545                 550                 555                 560
Arg Ala Arg Ala Glu Asn Val Ser Arg Asn Gly Gln Asp Pro Phe Thr
                565                 570                 575
Ser Ile Ser Leu Pro Gln Ala Val Ile Ser Leu Asn Gln Gly Val Gly
            580                 585                 590
Arg Leu Ile Arg Asp Glu Arg Asp Arg Gly Val Leu Ile Leu Cys Asp
        595                 600                 605
Asn Arg Ile Val Asn Arg Glu Tyr Gly Glu Ala Phe Leu Asn Ser Leu
    610                 615                 620
Pro Pro Met Ser Arg Thr Arg Asp Met Asp Lys Val Val Asp Phe Leu
625                 630                 635                 640
Gln Gln Ile Lys
```

<210> SEQ ID NO 26
<211> LENGTH: 9
<212> TYPE: PRT
<213> ORGANISM: Artificial Sequence
<220> FEATURE:
<223> OTHER INFORMATION: Motif V

<400> SEQUENCE: 26

```
Leu Gly Thr Gly Ala Phe Trp Glu Gly
1               5
```

<210> SEQ ID NO 27
<211> LENGTH: 22
<212> TYPE: PRT
<213> ORGANISM: Artificial Sequence
<220> FEATURE:
<223> OTHER INFORMATION: Motif VI

<400> SEQUENCE: 27

```
Gln Gly Val Gly Arg Leu Ile Arg Asp Glu Arg Asp Arg Gly Val Leu
1               5                   10                  15
Ile Leu Cys Asp Asn Arg
            20
```

<210> SEQ ID NO 28
<211> LENGTH: 726
<212> TYPE: PRT
<213> ORGANISM: Methanohalobium evestigatum

<400> SEQUENCE: 28

```
Met Lys Gly Ser Lys Gly Tyr Leu Lys Tyr Phe Thr Lys Asp Ser Cys
1               5                   10                  15
Tyr Pro Asn Gln Glu Asp Ala Met Glu Asn Ile His Ser Ala Leu Leu
            20                  25                  30
Lys Lys Gln Ile Val Leu Phe Glu Gly Ala Cys Gly Thr Gly Lys Thr
        35                  40                  45
Leu Ser Ala Leu Ala Pro Ala Leu Gln Val Gly Lys Gln Leu Asp Lys
    50                  55                  60
Thr Val Ile Ile Ala Thr Asn Val His Gln Met Val Gln Phe Ile
65                  70                  75                  80
Gln Glu Ala Arg Asp Ile Lys Lys Thr Asn Asp Ile Lys Ala Ala Val
                85                  90                  95
Ile Lys Gly Lys Thr Asn Met Cys Pro His Gly Ile Asp Tyr Asp Glu
        100                 105                 110
Cys Thr Val Lys Arg Glu Asn Thr Phe Asp Leu Ile Glu Leu Glu Lys
        115                 120                 125
Asp Ile Gln Leu Lys Arg Gln Glu Leu Lys Ser Ala Asn Lys Asn Tyr
    130                 135                 140
Lys Gln Ser Lys Asp Pro Glu Leu Ile Arg Leu Arg Asp Glu Leu Ser
145                 150                 155                 160
Lys Glu Leu Glu Asn Ser Glu Lys Ala Arg Asn Leu Arg Gly Arg
            165                 170                 175
Thr Cys Ser Glu Leu Tyr Glu Val Leu Asn Tyr Asp Ser Glu Lys Phe
            180                 185                 190
Arg Asp Trp Leu Phe Lys Asp Val Arg Thr Pro Glu Glu Val Asn Asp
        195                 200                 205
Phe Ala Tyr Gln Asn Ser Met Cys Gly Tyr Glu Leu Leu Lys Arg Glu
    210                 215                 220
Ile Lys Tyr Ala Asp Leu Val Ile Ala Asn Phe His His Val Leu Asn
225                 230                 235                 240
Gln Asp Ile Phe Ser Thr Leu Leu Ser Trp Ile Asp Arg Glu Pro Gln
                245                 250                 255
Asp Val Ile Val Ile Phe Asp Glu Ala His Asn Ile Glu Ser Ala Ala
        260                 265                 270
Arg Ser His Ser Ser Ile Thr Ile Thr Glu His Thr Ile Glu Lys Ala
        275                 280                 285
Met Ser Glu Val Asn Glu Tyr Ile Gly Gln Val Pro Asp Glu Arg Leu
    290                 295                 300
Gly Asn Leu Phe Ser Thr Leu Leu Asp Val Val Gln Asn Thr Tyr Asn
305                 310                 315                 320
Ser Arg Phe Lys Phe Gly Glu Lys Glu Lys Ile Gly Lys Tyr Trp Tyr
            325                 330                 335
Asp Ile Arg Ile Ser Asp Pro Tyr Asp Arg Asn Asp Met Val Ala Gly
                340                 345                 350
Lys Phe Leu Arg Gln Ala Lys Glu Glu Gly Phe Gly Asp Lys Lys Gln
            355                 360                 365
Ile Arg Glu Leu Leu Glu Glu Ala Ser Glu Phe Gly Ser Lys Leu Asp
    370                 375                 380
Glu Phe Tyr His Glu Gln Tyr Lys Lys Gly Leu Ser Lys Val Leu Lys
385                 390                 395                 400
His Ser Asp Ile Lys Tyr Ala Ala Asp Phe Leu Leu Ser Tyr Met Glu
                405                 410                 415
Leu Ser Asn Asn Pro His Tyr Tyr Pro Ile Leu Asn Val Arg Arg Asp
```

```
              420                 425                 430
Gln Asn Asp Glu Ile Tyr Gly Arg Ile Glu Leu Phe Thr Cys Ile Pro
            435                 440                 445

Lys Asn Val Thr Glu Pro Leu Phe Glu Ser Val Tyr Ser Ser Ile Leu
450                 455                 460

Met Ser Ala Thr Leu Arg Pro Phe Asp Met Val Lys Asn Thr Leu Gly
465                 470                 475                 480

Ile Ser Arg Glu Thr Cys Glu Leu Ala Tyr Gly Ser Ser Phe Ser Glu
                485                 490                 495

Asp Lys Arg Leu Thr Ile Ala Ala Ser Val Pro Pro Leu Phe Ala Lys
            500                 505                 510

Asn Arg Asp Asp Pro Gln Asn Ile Glu Thr Ile Glu Gln Ile Leu Leu
        515                 520                 525

Asp Ser Ile Glu Gln Ser Thr Gly Asn Val Ile Phe Phe Gln Asn
    530                 535                 540

Ser His Glu Ala Lys Arg Tyr His Gly Lys Leu Asp Ser Gln Leu Asn
545                 550                 555                 560

Ile Pro Val Phe Leu Asp Glu Val Gly Val Ser Ala Gln Gln Val Arg
                565                 570                 575

Gln Glu Phe Phe Asp Ile Gly Glu Asp Gly Gly Lys Ala Val Met Leu
            580                 585                 590

Ser Tyr Ile Trp Gly Thr Leu Ser Glu Gly Leu Asp Tyr Arg Glu Gly
        595                 600                 605

Arg Gly Arg Thr Val Ile Ile Val Gly Val Gly Tyr Pro Ala Leu Asn
    610                 615                 620

Asp Arg Met Asn Ala Val Glu Ser Ala Tyr Asp Ser Val Phe Gly Tyr
625                 630                 635                 640

Gly Ala Gly Trp Asp Tyr Ala Val Gln Ile Pro Thr Ile Arg Lys Ile
                645                 650                 655

Arg Gln Ala Met Gly Arg Val Val Arg Ser Pro Thr Asp Tyr Gly Ala
            660                 665                 670

Arg Ile Leu Ile Asp Gly Arg Phe Leu Thr Glu Ser Pro Gln Lys Phe
        675                 680                 685

Gly Lys Phe Ala Val Tyr Pro Val Phe Pro Glu Asp Glu Lys Lys Glu
    690                 695                 700

Phe Ile Asp Val Glu Pro Glu Lys Ile Lys Tyr Ser Leu Met Asn Phe
705                 710                 715                 720

Phe Met Asp Asn Ser Lys
                725

<210> SEQ ID NO 29
<211> LENGTH: 9
<212> TYPE: PRT
<213> ORGANISM: Artificial Sequence
<220> FEATURE:
<223> OTHER INFORMATION: Motif V

<400> SEQUENCE: 29

Tyr Ile Trp Gly Thr Leu Ser Glu Gly
1               5

<210> SEQ ID NO 30
<211> LENGTH: 22
<212> TYPE: PRT
<213> ORGANISM: Artificial Sequence
<220> FEATURE:
<223> OTHER INFORMATION: Motif VI
```

<400> SEQUENCE: 30

Gln Ala Met Gly Arg Val Val Arg Ser Pro Thr Asp Tyr Gly Ala Arg
1               5                   10                  15

Ile Leu Ile Asp Gly Arg
            20

<210> SEQ ID NO 31
<211> LENGTH: 773
<212> TYPE: PRT
<213> ORGANISM: Methanosarcina barkeri fusaro

<400> SEQUENCE: 31

Met Thr Gln Lys Asn Gly Tyr Met Arg Tyr Phe Thr Lys Gln Ser Cys
1               5                   10                  15

Tyr Pro Asn Gln Ala Glu Ala Met Glu Lys Ile His Ser Ala Leu Leu
            20                  25                  30

Asn Glu Lys Thr Val Leu Phe Glu Gly Ala Cys Gly Thr Gly Lys Thr
        35                  40                  45

Leu Ser Ala Leu Ala Pro Ala Leu Ser Val Gly Lys Lys Leu Asn Lys
    50                  55                  60

Val Val Ile Ile Val Thr Asn Val His Gln Gln Met Val Gln Phe Ile
65                  70                  75                  80

Asn Glu Ala Arg Glu Ile Ser Arg Asp Asn Asp Ile Lys Thr Ile Val
                85                  90                  95

Phe Lys Gly Lys Ala Ser Met Cys Pro Lys Asn Leu Asp Tyr Glu Glu
            100                 105                 110

Cys Arg Leu Lys Gly Glu Asn Thr Tyr Asp Leu Leu Asp Leu Glu Arg
        115                 120                 125

Glu Ile Ser Ser Lys Glu Lys Glu Leu Lys Asp Ala Tyr Glu Lys Tyr
    130                 135                 140

Lys Arg Thr Lys Asp Pro Ala Leu Tyr Ser Leu Arg Thr Glu Leu Glu
145                 150                 155                 160

Lys Glu Leu Glu Glu Thr Lys Lys Ser Arg Ala Leu Arg Asn Asn
                165                 170                 175

Ser Cys Leu Glu Leu Tyr Glu Val Leu Lys Phe Glu Gly Asn Glu Phe
            180                 185                 190

Ser Asn Trp Leu Phe Ser Asp Val Arg Ser Pro Glu Glu Ile Leu Glu
        195                 200                 205

Tyr Ala Glu Asp Arg Asp Met Cys Gly Tyr Glu Leu Leu Lys Lys Glu
    210                 215                 220

Leu Lys Asn Ala Glu Leu Leu Ile Cys Asn Phe His His Val Leu Ser
225                 230                 235                 240

Ala Glu Ile Phe Met Met Leu Leu Lys Trp Leu Glu Arg Asp Pro Glu
                245                 250                 255

Asp Val Ile Leu Ile Phe Asp Glu Ala His Asn Ile Glu Ala Ser Ala
            260                 265                 270

Arg Ser His Ser Ser Thr Met Leu Ser Glu Leu Thr Ile Glu Lys Ala
        275                 280                 285

Leu Ser Glu Val Gly Glu Thr Pro Glu Ser Asp Asn Ser Leu Met Leu
    290                 295                 300

Gly Lys Glu Thr Asp Ser Gly Gly Ile Pro Leu Asp Gln Asp Tyr
305                 310                 315                 320

Ala Ala Arg Leu Tyr Ala Lys Lys Leu Phe Thr Cys Leu Leu Thr Ala
                325                 330                 335

```
Leu Arg Asp Thr Tyr Ala Ala Lys Leu Lys Phe Gly Glu Arg Asn Arg
            340                 345                 350

Leu Gly Lys His Trp Gln Asp Ile Lys Ile Ser Asp Pro Tyr Glu Arg
            355                 360                 365

Phe Asp Ile Leu Lys Ala Arg Phe Leu Arg Glu Ala Met Lys Glu Gly
            370                 375                 380

Phe Ala Asp Glu Glu Lys Val Leu Thr Arg Leu Arg Glu Ile Gly Glu
385                 390                 395                 400

Phe Gly Gly Arg Leu Glu Ile Tyr Ala Glu Asn Tyr Lys Lys Gly
                405                 410                 415

Leu Leu Ala Val Pro Lys Arg Ser Gln Ile Arg Tyr Val Ala Asp Phe
            420                 425                 430

Leu Ser Ser Tyr Leu Val Leu Ser Asp Arg Gln Asn Tyr Tyr Pro Ile
            435                 440                 445

Leu Asn Val Arg Arg Asp Phe Lys Ser Asp Arg Ile Ala Gly Arg Ile
            450                 455                 460

Glu Leu Phe Thr Cys Ile Pro Lys Asn Val Thr Gln Pro Leu Phe Asp
465                 470                 475                 480

Ser Ile Tyr Ala Ala Val Leu Met Ser Ala Thr Leu Arg Pro Phe Glu
            485                 490                 495

Met Ile Lys Ser Thr Leu Gly Ile Ser Arg Glu Val Glu Ile Ser
            500                 505                 510

Tyr Ser Thr Thr Phe Pro Arg Glu Arg Arg Leu Thr Leu Ala Val Ser
            515                 520                 525

Ile Pro Pro Leu Phe Ala Lys Asn Arg Asp Ser Pro Glu Thr Leu Glu
            530                 535                 540

Ser Ile Lys Glu Ala Leu Leu Ala Ala Thr Val Ala Ser Pro Gly Asn
545                 550                 555                 560

Val Ile Ile Tyr Phe Gln Ser Tyr Ala Glu Ala Leu Arg Tyr Thr Lys
                565                 570                 575

Leu Leu Glu Pro Glu Leu Ser Ile Pro Ile Phe Leu Asp Glu Thr Gly
            580                 585                 590

Val Ser Ala Gln Glu Ile Arg Lys Lys Phe Phe Lys Ile Gly Glu Gln
            595                 600                 605

Gly Gly Lys Ala Leu Leu Ile Thr Tyr Leu Trp Gly Thr Leu Ser Glu
            610                 615                 620

Gly Val Asp Phe Arg Asp Ser Arg Gly Arg Thr Val Ile Ile Val Gly
625                 630                 635                 640

Ile Gly Tyr Pro Ala Leu Asn Asp Arg Ile Lys Ala Val Glu Ser Ala
                645                 650                 655

Tyr Asp Glu Val Phe Gly Cys Gly Glu Gly Trp Glu Phe Ala Val Gln
            660                 665                 670

Val Pro Thr Ile Arg Lys Val Arg Gln Ala Met Gly Arg Ile Val Arg
            675                 680                 685

Ser Pro Asp Asp Tyr Gly Val Arg Ile Leu Leu Asp Ser Arg Tyr Gln
            690                 695                 700

Gly Ser Gln Val Arg Lys Leu Gly Lys Phe Ser Val Phe Asp Tyr Phe
705                 710                 715                 720

Pro Pro Glu Glu Lys Arg Glu Phe Ile Asp Ile Ala Pro Lys Asp Val
                725                 730                 735

Gly Ser Ile Val Lys Glu Phe Phe Ala His Val Thr His Ser Asn Leu
            740                 745                 750
```

-continued

```
Glu Asn Glu Ser Lys Ser Gln Thr Ser Ser Arg Val Gly Phe Gly Ser
            755                 760                 765
Leu Ala Glu Lys Leu
    770

<210> SEQ ID NO 32
<211> LENGTH: 22
<212> TYPE: PRT
<213> ORGANISM: Artificial Sequence
<220> FEATURE:
<223> OTHER INFORMATION: Motif VI

<400> SEQUENCE: 32

Gln Ala Met Gly Arg Ile Val Arg Ser Pro Asp Asp Tyr Gly Val Arg
1               5                   10                  15

Ile Leu Leu Asp Ser Arg
            20

<210> SEQ ID NO 33
<211> LENGTH: 734
<212> TYPE: PRT
<213> ORGANISM: Haloferax volcanii

<400> SEQUENCE: 33

Met Ala His Ala Asn Gly Ala Pro Asp Asp Gly Asp Ala Asp Gly Ala
1               5                   10                  15

Trp Arg Phe Phe Pro Tyr Asp Glu Pro Tyr Pro Asn Gln Glu Ala Ala
            20                  25                  30

Met Ser Gly Ile Ala Asp Ala Leu Asp Asp Glu Arg Asn Val Leu Leu
        35                  40                  45

Glu Gly Ala Thr Gly Thr Gly Lys Thr Ile Ser Ala Leu Val Pro Ala
    50                  55                  60

Leu Ser Tyr Ala Arg Glu His Asp Lys Thr Val Val Ile Thr Thr Asn
65                  70                  75                  80

Val His Gln Gln Met Arg Gln Phe Val Glu Asp Ala Arg Ala Ile Thr
                85                  90                  95

Arg Glu Glu Ala Ile Arg Ala Val Val Phe Arg Gly Lys Ser Ser Met
            100                 105                 110

Cys His Ile Asp Val Gly Phe Gln Glu Cys Gln Thr Leu Arg Asp Thr
        115                 120                 125

Thr Arg Ser Ile Val Glu Lys Glu Ser Asp Lys Ala Glu Leu Ser Glu
    130                 135                 140

Gln Thr Gln Ser Leu Leu Asp Gly Ile Arg Glu Gly Ser Gly Ser Ala
145                 150                 155                 160

Ala Asp Ala Arg Ser Ala Val Thr Asp Glu Leu Asp Ala Ile Asp Asp
                165                 170                 175

Glu Leu Ala Glu Leu Lys Glu Gly Asn Tyr Cys Glu His Tyr Tyr Asn
            180                 185                 190

Asn Leu Thr Arg Asn Thr Asp Glu Phe Phe Gln Trp Leu Phe Asp Asp
        195                 200                 205

Val Arg Thr Pro Asp Glu Ile Phe Glu Tyr Ala Gly Lys Gln Asn Leu
    210                 215                 220

Cys Gly Tyr Glu Leu Leu Lys Glu Gly Met Glu Gly Ile Asp Leu Val
225                 230                 235                 240

Val Cys Asn Tyr His His Leu Leu Asp Pro Met Ile Arg Glu Gln Phe
                245                 250                 255

Phe Arg Trp Leu Asp Arg Asp Pro Asp Asp Val Ile Thr Val Phe Asp
```

```
                    260                 265                 270
Glu Ala His Asn Ile Glu Gly Ala Ala Arg Asp His Ala Ser Arg Ala
            275                 280                 285
Leu Thr Glu Asn Thr Leu Glu Ser Ala Met Thr Glu Leu Glu Asp Glu
        290                 295                 300
Asp Asp Ser Arg Ala Glu Ser Ala Arg Asn Val Ile Gly Thr Phe Leu
305                 310                 315                 320
Asp Ala Leu Arg Asp Ser Tyr Glu Ser Ala Phe Gly Phe Gly Glu Arg
                325                 330                 335
Glu Gln Val Gly Glu Asn Trp Tyr Asp Leu Ser Ile Ala Ser Gln Gly
            340                 345                 350
Arg Arg Asp Asp Leu Thr Met Glu Phe Leu Gln Ser Tyr Glu Gly Arg
        355                 360                 365
Gly Ile Asp Val Glu Val Glu Leu Ala Leu Gln Leu Gly Lys Gln Leu
    370                 375                 380
Asp Glu Gln Tyr Glu Asp Ala Tyr Lys Asn Gly Glu Ala Thr Thr Arg
385                 390                 395                 400
Lys Glu Cys Gln Thr Leu Gln Ala Ala Asn Phe Ile Ala Asp Trp Thr
                405                 410                 415
Glu Leu Gly Asp Glu Leu Gly Arg His Pro Val Leu Ser Val Arg Arg
            420                 425                 430
Asp Gly Gly Thr Asp Glu Ile Tyr Gly Arg Ala Glu Leu Tyr Thr Cys
        435                 440                 445
Ile Pro Arg Glu Val Thr Lys Glu Leu Phe Glu Glu Val His Ala Ser
    450                 455                 460
Ile Leu Met Ser Ala Thr Leu Arg Pro Phe Asp Val Thr Glu Ser Thr
465                 470                 475                 480
Leu Gly Leu Asp Asp Pro Val Thr Met Ala Tyr Gly Leu Glu Tyr Pro
                485                 490                 495
Glu Glu Asn Arg Arg Thr Phe Ser Val Ser Leu Pro Ala Leu Phe Ser
            500                 505                 510
Ser Glu Arg Asp Asp Pro Gly Thr Gln Glu Thr Val Glu Glu Val Leu
        515                 520                 525
Ala Asp Ala Ala Gly Phe Thr Pro Gly Asn Thr Leu Ala Phe Phe Pro
    530                 535                 540
Ser Tyr Ala Glu Ala Glu Arg Tyr His Glu Arg Leu Arg Ala Asn Pro
545                 550                 555                 560
Asn Val Asp Ala Glu Leu Phe Leu Asp Glu Pro Gly Val Arg Ala Glu
                565                 570                 575
Glu Met Arg Arg Glu Phe Val Ala Glu Asp Gly Ala Val Leu Leu Thr
            580                 585                 590
Ser Leu Trp Gly Thr Leu Ala Glu Gly Val Ser Phe Asp Gly Asp Asp
        595                 600                 605
Ala Arg Thr Val Val Val Gly Val Pro Tyr Pro His Leu Ser Glu
    610                 615                 620
Arg Leu Glu Ala Val Gln Asp Ala Tyr Asp Arg Val Tyr Arg Arg Lys
625                 630                 635                 640
Lys Asp Ala Gly Trp Arg Tyr Ala Val Glu Ile Pro Thr Ile Arg Lys
                645                 650                 655
Thr Arg Gln Ala Leu Gly Arg Val Ile Arg Ala Pro Asp Asp Phe Gly
            660                 665                 670
Val Arg Val Leu Ala Asp Lys Arg Tyr Thr Arg Glu Ser Thr Ser Met
        675                 680                 685
```

Gly Lys Tyr Gly Val Arg Gly Ser Phe Pro Val Glu Glu Arg Ser Glu
            690                 695                 700

Met Val Asp Ile Ala Pro Asn Lys Leu Lys Phe Ala Met Leu Asn Phe
705                 710                 715                 720

Tyr Thr Asp His Asp Ala Tyr Asp Gly Asp Pro Pro Arg Pro
            725                 730

<210> SEQ ID NO 34
<211> LENGTH: 22
<212> TYPE: PRT
<213> ORGANISM: Artificial Sequence
<220> FEATURE:
<223> OTHER INFORMATION: Motif VI

<400> SEQUENCE: 34

Gln Ala Leu Gly Arg Val Ile Arg Ala Pro Asp Asp Phe Gly Val Arg
1               5                   10                  15

Val Leu Ala Asp Lys Arg
            20

<210> SEQ ID NO 35
<211> LENGTH: 620
<212> TYPE: PRT
<213> ORGANISM: Thermoplasma acidophilum

<400> SEQUENCE: 35

Met Tyr Glu Asn Arg Gln Tyr Gln Val Glu Ala Ile Asp Phe Leu Arg
1               5                   10                  15

Ser Ser Leu Gln Lys Ser Tyr Gly Val Ala Leu Glu Ser Pro Thr Gly
            20                  25                  30

Ser Gly Lys Thr Ile Met Ala Leu Lys Ser Ala Leu Gln Tyr Ser Ser
        35                  40                  45

Glu Arg Lys Leu Lys Val Leu Tyr Leu Val Arg Thr Asn Ser Gln Glu
    50                  55                  60

Glu Gln Val Ile Lys Glu Leu Arg Ser Leu Ser Ser Thr Met Lys Ile
65                  70                  75                  80

Arg Ala Ile Pro Met Gln Gly Arg Val Asn Met Cys Ile Leu Tyr Arg
                85                  90                  95

Met Val Asp Asp Leu His Glu Ile Asn Ala Glu Ser Leu Ala Lys Phe
            100                 105                 110

Cys Asn Met Lys Lys Arg Glu Val Met Ala Gly Asn Glu Ala Ala Cys
        115                 120                 125

Pro Tyr Phe Asn Phe Lys Ile Arg Ser Asp Glu Thr Lys Arg Phe Leu
    130                 135                 140

Phe Asp Glu Leu Pro Thr Ala Glu Glu Phe Tyr Asp Tyr Gly Glu Arg
145                 150                 155                 160

Asn Asn Val Cys Pro Tyr Glu Ser Met Lys Ala Ala Leu Pro Asp Ala
                165                 170                 175

Asp Ile Val Ile Ala Pro Tyr Ala Tyr Phe Leu Asn Arg Ser Val Ala
            180                 185                 190

Glu Lys Phe Leu Ser His Trp Gly Val Ser Arg Asn Gln Ile Val Ile
        195                 200                 205

Ile Leu Asp Glu Ala His Asn Leu Pro Asp Ile Gly Arg Ser Ile Gly
    210                 215                 220

Ser Phe Arg Ile Ser Val Glu Ser Leu Asn Arg Ala Asp Arg Glu Ala
225                 230                 235                 240

Gln Ala Tyr Gly Asp Pro Glu Leu Ser Gln Lys Ile His Val Ser Asp
                245                 250                 255

Leu Ile Glu Met Ile Arg Ser Ala Leu Gln Ser Met Val Ser Glu Arg
        260                 265                 270

Cys Gly Lys Gly Asp Val Arg Ile Arg Phe Gln Glu Phe Met Glu Tyr
            275                 280                 285

Met Arg Ile Met Asn Lys Arg Ser Glu Arg Glu Ile Arg Ser Leu Leu
        290                 295                 300

Asn Tyr Leu Tyr Leu Phe Gly Glu Tyr Val Glu Asn Glu Lys Glu Lys
305                 310                 315                 320

Val Gly Lys Val Pro Phe Ser Tyr Cys Ser Ser Val Ala Ser Arg Ile
                325                 330                 335

Ile Ala Phe Ser Asp Gln Asp Glu Glu Lys Tyr Ala Ala Ile Leu Ser
            340                 345                 350

Pro Glu Asp Gly Gly Tyr Met Gln Ala Ala Cys Leu Asp Pro Ser Gly
        355                 360                 365

Ile Leu Glu Val Leu Lys Glu Ser Lys Thr Ile His Met Ser Gly Thr
    370                 375                 380

Leu Asp Pro Phe Asp Phe Tyr Ser Asp Ile Thr Gly Phe Glu Ile Pro
385                 390                 395                 400

Phe Lys Lys Ile Gly Glu Ile Phe Pro Pro Glu Asn Arg Tyr Ile Ala
                405                 410                 415

Tyr Tyr Asp Gly Val Ser Ser Lys Tyr Asp Thr Leu Asp Glu Lys Glu
            420                 425                 430

Leu Asp Arg Met Ala Thr Val Ile Glu Asp Ile Leu Lys Val Lys
        435                 440                 445

Lys Asn Thr Ile Val Tyr Phe Pro Ser Tyr Ser Leu Met Asp Arg Val
450                 455                 460

Glu Asn Arg Val Ser Phe Glu His Met Lys Glu Tyr Arg Gly Ile Asp
465                 470                 475                 480

Gln Lys Glu Leu Tyr Ser Met Leu Lys Lys Phe Arg Arg Asp His Gly
                485                 490                 495

Thr Ile Phe Ala Val Ser Gly Gly Arg Leu Ser Glu Gly Ile Asn Phe
            500                 505                 510

Pro Gly Asn Glu Leu Glu Met Ile Ile Leu Ala Gly Leu Pro Phe Pro
        515                 520                 525

Arg Pro Asp Ala Ile Asn Arg Ser Leu Phe Asp Tyr Tyr Glu Arg Lys
    530                 535                 540

Tyr Gly Lys Gly Trp Glu Tyr Ser Val Val Tyr Pro Thr Ala Ile Lys
545                 550                 555                 560

Ile Arg Gln Glu Ile Gly Arg Leu Ile Arg Ser Ala Glu Asp Thr Gly
                565                 570                 575

Ala Cys Val Ile Leu Asp Lys Arg Ala Gly Gln Phe Arg Lys Phe Ile
            580                 585                 590

Pro Asp Met Lys Lys Thr Ser Asp Pro Ala Ser Asp Ile Tyr Asn Phe
        595                 600                 605

Phe Ile Ser Ala Gln Ala Arg Glu Lys Tyr Gly Ala
    610                 615                 620

<210> SEQ ID NO 36
<211> LENGTH: 9
<212> TYPE: PRT
<213> ORGANISM: Artificial Sequence
<220> FEATURE:
<223> OTHER INFORMATION: Motif V -continued

<400> SEQUENCE: 36

Val Ser Gly Gly Arg Leu Ser Glu Gly
1               5

<210> SEQ ID NO 37
<211> LENGTH: 22
<212> TYPE: PRT
<213> ORGANISM: Artificial Sequence
<220> FEATURE:
<223> OTHER INFORMATION: Motif VI

<400> SEQUENCE: 37

Gln Glu Ile Gly Arg Leu Ile Arg Ser Ala Glu Asp Thr Gly Ala Cys
1               5                   10                  15

Val Ile Leu Asp Lys Arg
            20

<210> SEQ ID NO 38
<211> LENGTH: 643
<212> TYPE: PRT
<213> ORGANISM: Thermococcus sibiricus

<400> SEQUENCE: 38

Met Ser Glu Tyr Phe Pro Tyr Gln Ser Leu Arg Pro Asn Gln Glu Asp
1               5                   10                  15

Phe Ile Lys Leu Val Asp Thr Val Arg Asn Gly Glu Asn Leu Val
                20                  25                  30

Ile Glu Ala Pro Thr Gly Phe Gly Lys Thr Ile Ser Val Leu Ala Gly
            35                  40                  45

Ala Leu Pro Tyr Ala Lys Glu Met Gly Tyr Lys Ile Ile Tyr Leu Ala
        50                  55                  60

Arg Thr His Lys Gln Met Asp Arg Val Ile Glu Glu Leu Lys Ala Ile
65                  70                  75                  80

Ser Asn Lys Thr Gln Val Ser Gly Val Glu Phe Arg Ser Arg Lys Glu
                85                  90                  95

Leu Cys Leu His Gln Tyr Val Gln Asn Phe Ala Pro Asp Ala Tyr Asn
            100                 105                 110

Ala Met Ile Val Cys Lys Asn Leu Lys Lys Leu Gly Lys Cys Glu Phe
        115                 120                 125

Phe Glu Asn Leu Lys Lys Lys Glu Glu Phe Asp Glu Leu Ala Gln
    130                 135                 140

Tyr Phe Val Gln Lys Pro Ala Glu Pro Met Met Ile Leu Thr His Ser
145                 150                 155                 160

Lys Met Leu Asp Phe Cys Pro Tyr Glu Leu Thr Arg Lys Ile Ala Phe
                165                 170                 175

Asn Ser Asp Val Ile Val Ala Ser Tyr Leu Tyr Met Ile Asp Pro Ala
            180                 185                 190

Ile Arg Glu Asn Phe Met Ala Tyr Phe Asp Tyr Ser Asp Leu
        195                 200                 205

Ile Val Ile Phe Asp Glu Ala His Asn Leu Pro Asn Gln Ala Ile Asn
    210                 215                 220

Ala Leu Ser Asp Arg Leu Ser Val Tyr Ser Ile Asn Arg Ala Ile Lys
225                 230                 235                 240

Glu Ala Asp Glu Tyr Lys Glu His Glu Ile Ala Asn Phe Leu Ser Ile
                245                 250                 255

Phe Leu Lys Gly Leu Glu Asn Leu Tyr Gln Glu Lys Leu Arg Asp Leu

```
                260                 265                 270
Lys Ile Asp Glu Val Pro Ile Ile Pro Glu Ser Ile Phe Tyr His Val
            275                 280                 285

Phe Asp Val Leu Lys Ile Asn Glu Lys Gln Leu Ile Arg Ile Leu Asp
            290                 295                 300

Gln Met Val Lys Ala Gly Asp Ala Ile Arg Glu Asp Lys Ile Glu Arg
305                 310                 315                 320

Ser Leu Pro Pro Arg Ser Tyr Val Gly Arg Val Gly Glu Phe Leu Leu
                325                 330                 335

Leu Trp Phe Ala Leu Ile Gly Lys Glu Asp Tyr Leu Phe Leu Met Ser
            340                 345                 350

Arg Glu Lys Gly Phe Ser Leu Glu Leu Val Ala Leu Asp Pro Ser Lys
            355                 360                 365

Ala Leu Ser Phe Val Lys Asn Val Gln Ser Ala Ile Phe Met Ser Gly
            370                 375                 380

Thr Met Thr Pro Leu Glu Ala Phe Ala Asp Ile Met Gly Ile Glu Gly
385                 390                 395                 400

Lys Leu Lys Lys Phe Pro Arg Ile Val Lys Glu Asn Ala Ile Val
                405                 410                 415

Leu Val Ala Lys Asp Val Ser Thr Arg Gly Asp Glu Arg Ser Leu Glu
                420                 425                 430

Leu Tyr Lys Lys Met Ala Lys Tyr Ile Val Glu Ala Val Lys Leu Ile
            435                 440                 445

Pro Lys Asn Val Gly Val Phe Thr Ala Ser Tyr Glu Val Leu Glu Gly
            450                 455                 460

Leu Leu Ser Ala Asn Val Asp Ile Gln Ile Gln Glu Val Ser Gly Lys
465                 470                 475                 480

Lys Val Phe Ile Glu Lys Arg Gly Ala Ser Ser Lys Glu Asn Asp Leu
                485                 490                 495

Leu Val Met Ala Phe Lys Glu Glu Ala Lys Arg Asp Gly Ala Val Leu
            500                 505                 510

Leu Gly Val Met Gly Gly Arg Asn Ser Glu Gly Gln Asp Tyr Ser Gly
            515                 520                 525

Asp Glu Met Asn Gly Val Ile Leu Val Gly Ile Pro Tyr Ala Arg Pro
530                 535                 540

Thr Pro Lys Val Gln Ala Gln Ile Arg Tyr Phe Glu Asn Lys Phe Pro
545                 550                 555                 560

Arg Lys Gly Arg Tyr Tyr Gly Tyr Val Leu Pro Ala His Lys Lys Leu
                565                 570                 575

Val Gln Ala Ala Gly Arg Val His Arg Ser Glu Glu Lys Gly Ala
            580                 585                 590

Val Val Val Leu Asp Tyr Arg Leu Leu Trp Ser Asn Val Arg Lys Asp
                595                 600                 605

Leu Pro Asp Trp Met Lys Glu Thr Ile Lys Pro Val Thr Leu Ala Ser
            610                 615                 620

Met Lys Arg His Leu Ile Asp Phe Tyr Arg Gly Glu Lys Ile Lys Val
625                 630                 635                 640

Glu Lys Asp

<210> SEQ ID NO 39
<211> LENGTH: 9
<212> TYPE: PRT
<213> ORGANISM: Artificial Sequence
<220> FEATURE:
```

<223> OTHER INFORMATION: Motif V

<400> SEQUENCE: 39

Val Met Gly Gly Arg Asn Ser Glu Gly
1               5

<210> SEQ ID NO 40
<211> LENGTH: 22
<212> TYPE: PRT
<213> ORGANISM: Artificial Sequence
<220> FEATURE:
<223> OTHER INFORMATION: Motif VI

<400> SEQUENCE: 40

Gln Ala Ala Gly Arg Val His Arg Ser Glu Glu Lys Gly Ala Val
1               5                   10                  15

Val Val Leu Asp Tyr Arg
            20

<210> SEQ ID NO 41
<211> LENGTH: 637
<212> TYPE: PRT
<213> ORGANISM: Pyrococcus abyssi

<400> SEQUENCE: 41

Met Phe Glu Tyr Phe Pro Tyr Lys Thr Leu Arg Pro His Gln Asp Glu
1               5                   10                  15

Phe Ile Glu Leu Val Arg Asp Val Val Lys Arg Gly Glu Lys Val Ile
                20                  25                  30

Ile Glu Ala Pro Thr Gly Phe Gly Lys Thr Ile Ser Val Leu Ala Gly
            35                  40                  45

Val Leu Pro His Ala Ile Ser Phe Gly Tyr Lys Val Ile Tyr Leu Ala
        50                  55                  60

Arg Thr His Lys Gln Met Asp Arg Val Ile Glu Leu Lys Arg Ile
65                  70                  75                  80

Arg Glu Ile Ala Lys Val Ser Gly Ile Glu Phe Arg Ser Arg Lys Asp
                85                  90                  95

Leu Cys Leu His Ser Tyr Ile Arg Thr Phe Ala Gln Asp Ala Tyr Thr
            100                 105                 110

Ser Met Ile Val Cys Lys Ser Leu Lys Arg Leu Gly Lys Cys Lys Tyr
        115                 120                 125

Phe Glu Asn Leu Lys Glu Lys Arg Asp Lys Val Lys Glu Ile Val Glu
    130                 135                 140

Phe Phe Leu Glu Asn Pro Ser Tyr Pro Trp Glu Val Ile Glu Tyr Ser
145                 150                 155                 160

Asn Leu Leu Glu Leu Cys Pro Tyr Glu Val Thr Arg Lys Val Gly Glu
                165                 170                 175

Lys Ala Asn Val Ile Val Ala Ser Tyr Leu Tyr Met Val Asn Pro Trp
            180                 185                 190

Ile Arg Gln Ala Phe Leu Asp Gly Leu Gly Leu Glu Tyr Ser Asp Leu
        195                 200                 205

Ile Val Ile Phe Asp Glu Ala His Asn Leu Pro Asp Gln Ala Ile Ser
    210                 215                 220

Ala Leu Ser Asp Arg Leu Ser Ile Arg Ser Val Glu Arg Ala Ile Lys
225                 230                 235                 240

Glu Ala Asn Glu Tyr Gly Glu Lys Asp Ile Glu Asn Phe Leu Ser Ile
                245                 250                 255

```
Phe Leu Arg Gly Leu Glu Ile Ile Tyr Lys Glu Lys Leu Glu Asn Tyr
            260                 265                 270
Glu Ile Ser Glu Val Pro Leu Ser Pro Ala Ser Ile Phe Glu His Val
        275                 280                 285
Ser Ser Ile Leu Gly Leu Arg Glu Arg Asp Leu Leu Arg Phe Leu Gln
    290                 295                 300
Glu Met Val Glu Val Gly Asp Ala Ile Arg Glu Asp Lys Ile Glu Arg
305                 310                 315                 320
Asn Leu Pro Pro Arg Ser Tyr Val Gly Arg Val Gly Glu Phe Leu Trp
                325                 330                 335
Asn Trp Ile Ser Leu Ala Asp Arg Ser Asp Tyr Leu His Val Phe Thr
            340                 345                 350
Arg Glu Lys Gly Leu Ala Leu Glu Ile Val Ala Leu Asp Pro Ser Val
        355                 360                 365
Ala Leu Glu Phe Leu Glu Asp Val His Ser Ala Ile Leu Met Ser Gly
    370                 375                 380
Thr Leu Ser Pro Leu Glu Ala Phe Arg Asp Ile Ile Gly Val Asn Ala
385                 390                 395                 400
Arg Leu Lys Lys Phe Pro Arg Met Val Lys Ser Glu Asn Ala Ile Val
                405                 410                 415
Leu Val Ala Arg Asp Val Ser Thr Arg Gly Glu Glu Arg Ser Pro Val
            420                 425                 430
Leu Tyr Lys Lys Leu Ala Glu Tyr Ile Phe Glu Ala Val Lys Ile Ile
        435                 440                 445
Pro Lys Asn Val Gly Val Phe Thr Ala Ser Tyr Glu Val Leu Glu Gly
    450                 455                 460
Leu Ile Ser Thr Asn Val His Ile Arg Ile Glu Glu Ile Gly Lys
465                 470                 475                 480
Lys Val Phe Ile Glu Lys Arg Asp Ala Ser Ser Glu Asn Asp Ala
                485                 490                 495
Leu Val Ala Glu Phe Lys Ala Glu Ala Lys Gly Asn Gly Val Leu
            500                 505                 510
Phe Gly Val Met Gly Gly Arg Asn Ser Glu Gly Gln Asp Tyr Ser Gly
        515                 520                 525
Asp Glu Met Asn Gly Val Ile Leu Val Gly Ile Pro Tyr Ala Arg Pro
    530                 535                 540
Thr Pro Arg Val Gln Ala Gln Ile Arg Tyr Tyr Glu Lys Lys Phe Pro
545                 550                 555                 560
Gly Lys Gly Arg Tyr Tyr Gly Tyr Leu Leu Pro Ala His Arg Lys Leu
                565                 570                 575
Ala Gln Ala Ala Gly Arg Val His Arg Ser Glu Glu Glu Lys Gly Ser
            580                 585                 590
Ile Val Ile Leu Asp Tyr Arg Val Leu Trp Asn Thr Val Lys Arg Asp
        595                 600                 605
Leu Pro Asp Trp Met Val Glu Thr Met Gln Pro Val Thr Leu Pro Leu
    610                 615                 620
Met Arg Ile Lys Leu Arg Lys Phe Trp Arg Ala Val Lys
625                 630                 635

<210> SEQ ID NO 42
<211> LENGTH: 22
<212> TYPE: PRT
<213> ORGANISM: Artificial Sequence
<220> FEATURE:
<223> OTHER INFORMATION: Motif VI
```

-continued

<400> SEQUENCE: 42

Gln Ala Ala Gly Arg Val His Arg Ser Glu Glu Lys Gly Ser Ile
1               5                   10                  15

Val Ile Leu Asp Tyr Arg
            20

<210> SEQ ID NO 43
<211> LENGTH: 631
<212> TYPE: PRT
<213> ORGANISM: Pyrococcus furiosus

<400> SEQUENCE: 43

Met Glu Glu Leu Gln Tyr Phe Pro Tyr Glu Arg Leu Arg Pro Asn Gln
1               5                   10                  15

Arg Glu Phe Ile Glu Ile Val Lys Glu Ala Val Lys Arg Gly Glu Asn
                20                  25                  30

Leu Ile Val Glu Ala Pro Thr Gly Phe Gly Lys Thr Ile Ser Val Leu
            35                  40                  45

Ala Gly Val Leu Pro Tyr Ala Ile Ser Leu Gly Tyr Lys Val Val Tyr
50                  55                  60

Leu Ala Arg Thr His Lys Gln Met Asp Arg Val Ile Glu Glu Leu Lys
65                  70                  75                  80

Lys Ile Arg Glu Arg Asn Glu Val Ser Gly Ile Glu Phe Arg Ser Arg
                85                  90                  95

Arg Asp Leu Cys Leu His Ser Tyr Ile Gln Thr Phe Val Gln Asp Ala
            100                 105                 110

Tyr Thr Ser Met Ile Val Cys Lys Thr Leu Arg Lys Leu Gly Lys Cys
        115                 120                 125

Pro Phe Phe Glu Asn Ile Lys Glu Lys Arg Asp Arg Val Glu Glu Ile
    130                 135                 140

Val Arg Phe Phe Leu Asn Ser Pro Pro Phe Pro His Glu Val Leu Glu
145                 150                 155                 160

Tyr Ser Glu Leu Leu Glu Leu Cys Pro Tyr Glu Ile Thr Lys Lys Ile
                165                 170                 175

Gly Glu Lys Ala Asn Val Ile Val Ala Ser Tyr Leu Tyr Met Ile Ser
            180                 185                 190

Pro Pro Ile Arg Gln Ala Phe Leu Glu Asn Leu Gly Val Asp Tyr Ser
        195                 200                 205

Asp Leu Ile Val Ile Phe Asp Glu Ala His Asn Leu Pro Asp Gln Ala
    210                 215                 220

Ile Ser Ala Leu Ser Asp Arg Leu Ser Ile Arg Ser Ile Glu Arg Ala
225                 230                 235                 240

Ile Lys Glu Ala Glu Glu Tyr Gly Glu Lys Asp Ile Glu Asn Phe Leu
                245                 250                 255

Ser Ile Leu Leu Arg Gly Leu Gly Ile Leu Tyr Lys Glu Lys Leu Glu
            260                 265                 270

Asn Tyr Glu Ser Glu Glu Val Pro Ile Arg Pro Glu Glu Val Phe Leu
        275                 280                 285

His Val Ala Ser Val Leu Gly Trp Ser Gly Arg Glu Ile Gly Met Met
    290                 295                 300

Leu Glu Asp Met Ile Glu Val Gly Asp Ala Ile Arg Glu Asp Arg Ile
305                 310                 315                 320

Glu Arg Asn Leu Pro Pro Arg Ser Tyr Val Gly Arg Val Gly Glu Phe
                325                 330                 335

-continued

```
Leu Trp Asn Trp Leu Ala Leu Arg Glu Arg Glu Asp Tyr Leu His Leu
            340                 345                 350

Phe Thr Lys Glu Arg Gly Leu Ala Leu Glu Leu Val Ala Leu Asp Pro
            355                 360                 365

Ser Val Ala Leu Glu Phe Leu Glu Glu Val His Ser Ala Ile Phe Met
370                 375                 380

Ser Gly Thr Leu Ser Pro Leu Glu Ala Phe Arg Asp Ile Ile Gly Val
385                 390                 395                 400

Lys Ala Glu Leu Lys Lys Phe Pro Arg Met Ile Lys Arg Glu Asn Ala
            405                 410                 415

Ile Val Leu Val Ala Arg Asp Val Ser Thr Arg Gly Ile Glu Arg Ser
            420                 425                 430

Pro Ser Leu Tyr Arg Arg Ile Ser Glu Tyr Ile Phe Glu Ala Val Arg
            435                 440                 445

Asn Thr Pro Lys Asn Val Gly Val Phe Thr Ala Ser Tyr Glu Val Leu
450                 455                 460

Glu Gly Ile Leu Ser Thr Asn Val His Ile Lys Ile Glu Glu Glu Ile
465                 470                 475                 480

Gly Lys Lys Val Phe Ile Glu Lys Arg Asp Ala Pro Ser Arg Glu Asn
            485                 490                 495

Asp Glu Met Ile Arg Ala Phe Lys Glu Ser Lys Gly Lys Gly Ala
            500                 505                 510

Val Leu Phe Gly Val Met Gly Gly Arg Asn Ser Glu Gly Gln Asp Tyr
            515                 520                 525

Ser Gly Asp Glu Met Asn Gly Val Val Leu Val Gly Ile Pro Tyr Ala
530                 535                 540

Arg Pro Thr Pro Arg Val Gln Ala Gln Ile Arg Tyr Phe Glu Lys Lys
545                 550                 555                 560

Phe Pro Gly Lys Gly Arg Tyr Tyr Gly Tyr Val Leu Pro Ala His Arg
            565                 570                 575

Lys Leu Thr Gln Ala Ala Gly Arg Val His Arg Ser Glu Glu Glu Lys
            580                 585                 590

Gly Ser Ile Val Ile Leu Asp Tyr Arg Val Leu Trp Lys Ser Val Lys
            595                 600                 605

Lys Asp Leu Pro Asp Trp Met Val Glu Thr Met Ile Pro Val Thr Leu
610                 615                 620

Pro His Tyr Glu Asn Lys Thr
625                 630
```

<210> SEQ ID NO 44
<211> LENGTH: 732
<212> TYPE: PRT
<213> ORGANISM: Halobacterium sp. NRC-1

<400> SEQUENCE: 44

```
Met Gln Phe Phe Pro Lys Pro Ser Pro Tyr Asp Asn Gln Arg Ala Ala
1               5                   10                  15

Met Asp Ala Ile Arg Asp Ala Leu Asp Gly Gly Thr Asn Val Leu Phe
            20                  25                  30

Glu Gly Ala Cys Gly Thr Gly Lys Thr Leu Ala Ala Leu Ala Pro Ala
            35                  40                  45

Leu Ser His Ala Gln Ala Glu Asp Lys Thr Val Val Ile Thr Thr Asn
50                  55                  60

Val His Gln Gln Met Arg Gln Phe Val Arg Glu Ala Arg Glu Ile His
```

-continued

```
            65                  70                  75                  80
Ala Thr Glu Pro Ile Arg Ala Val Val Phe Lys Gly Lys Gly Ser Met
                        85                  90                  95

Cys His Ile Asp Val Asp Tyr Glu Glu Cys Gln Val Leu Arg Asp Asn
                    100                 105                 110

Thr His Glu Leu Val Asp Ala Thr Arg Asp Lys Arg Gln Leu Glu Glu
                115                 120                 125

Arg Gln Arg Ala Leu Leu Asp Glu Ala Gln Asp Gly Asp Thr Glu Ala
            130                 135                 140

Ala Asp Ala Arg Gln Ala Val Met Asp Glu Leu Glu Ala Val Glu Ser
145                 150                 155                 160

Glu Leu Ala Ala Leu Gln Asp Gly Asn Val Cys Glu Arg Tyr Arg Gln
                165                 170                 175

Asn Leu Val Gly Asn Thr Asp Glu Phe Tyr Gln Trp Leu Tyr Asp Asp
                180                 185                 190

Val Arg Thr Pro Glu Asp Ile Tyr Gly Tyr Ala Glu Glu Ala Gly Phe
            195                 200                 205

Cys Gly Tyr Glu Leu Leu Lys Asp Gly Ile Glu Gly Val Asp Leu Ala
            210                 215                 220

Val Cys Asn Tyr His His Leu Leu Asp Pro Gly Ile Arg Ala Gln Phe
225                 230                 235                 240

Phe Arg Trp Leu Gly Arg Asp Pro Glu Asp Val Val Val Phe Asp
                245                 250                 255

Glu Ala His Asn Ile Glu Asp Ala Ala Arg Asp His Ala Ala Glu Thr
                260                 265                 270

Leu Thr Glu Gln Thr Leu Asp Ser Ala Leu Asp Glu Leu Gln Asp Thr
            275                 280                 285

Ser Asp Gln Arg Ala Ala Ala Glu Arg Val Leu Gly Ala Phe Arg
290                 295                 300

Asp Ala Leu Val Glu Thr Tyr Glu Asp Ala Leu Arg Pro Gly Gly Asp
305                 310                 315                 320

Gly Pro Ala Asp Thr Lys Ser Ala Val Glu Ser Asn Trp Val Asp Val
                325                 330                 335

Pro Val Ala Asn Asp Asp Arg Arg Asp Asp Leu Thr Leu Ala Phe Leu
                340                 345                 350

Gln Ser Tyr Thr Gly Pro Gly Ile Thr Glu Asp Val Thr Asp Ala Leu
            355                 360                 365

Gly Leu Gly Glu Tyr Leu Asp Gly Glu Tyr Glu Asp Ala Tyr Arg Asn
            370                 375                 380

Gly Asp Ala Thr Thr Arg Arg Glu Cys His Val Leu Ala Ala Ala Glu
385                 390                 395                 400

Phe Val Glu Ala Tyr Val Glu Arg Gly Gly Glu Phe Gly Gln Tyr Pro
                405                 410                 415

Thr Ala Val Arg Arg Asp Asp Arg Thr Glu Ala Val Tyr Gly Arg
            420                 425                 430

Ala Glu Arg Tyr Thr Cys Ile Pro Arg Glu Val Thr Thr Asp Leu Phe
            435                 440                 445

Asp Ala Val His Ala Ser Val Leu Met Ser Ala Thr Leu Arg Pro Phe
            450                 455                 460

Asp Val Ile Gly Asp Val Leu Gly Leu Asp Asp Pro Val Glu Leu Ala
465                 470                 475                 480

Phe Gly Leu Gln Phe Pro Glu Asp Arg Arg Arg Thr Phe Ala Val Asp
                485                 490                 495
```

-continued

```
Thr Glu Pro Leu Phe Ser Ser Asn Arg Glu Asp Arg Ala Thr Gln Gln
            500                 505                 510
Ala Val Ala Gly Ala Leu Arg Asp Ala Ala Tyr Thr Pro Gly Asn
        515                 520                 525
Cys Leu Phe Phe Phe Pro Ser Tyr Ala Glu Ala Lys Arg Tyr His Asp
    530                 535                 540
Leu Leu Ala Asp Cys Asp Ala Thr Arg Tyr Leu Asp Glu Pro Gly Val
545                 550                 555                 560
Ala Ala Asp Asp Leu Arg Glu Ala Phe Val Ala Asp Gly Asp Gly Ala
                565                 570                 575
Leu Phe Thr Ser Leu Trp Gly Thr Leu Ala Glu Gly Val Ser Phe Asp
            580                 585                 590
Gly Asp Asp Ala Arg Thr Val Ala Val Val Gly Val Pro Tyr Pro His
        595                 600                 605
Leu Asp Ala Arg Thr Glu Ala Val Gln Asp Ala Tyr Ala Gln Ala Phe
    610                 615                 620
Ala Asp Arg Asp Ala Asp Gln Gly Leu Arg Ser Asp Arg Gln Asp Ala
625                 630                 635                 640
Gly Trp Arg Tyr Ala Val Glu Ile Pro Thr Val Arg Lys Thr Arg Gln
                645                 650                 655
Ala Met Gly Arg Val Ile Arg Ser Pro Glu Asp Phe Gly Val Arg Met
            660                 665                 670
Leu Val Asp Arg Arg Tyr Thr Ala Ala Ser Arg Thr Gly Met Gln Lys
        675                 680                 685
Tyr Ser Val Asn Pro Thr Phe Pro Pro Ser Glu Arg Ala Glu Met Val
    690                 695                 700
Asp Val Asp Pro Glu Lys Leu Arg Phe Ser Leu Leu Asn Phe Tyr Gly
705                 710                 715                 720
Asp Leu Gly Ala Tyr Gly Gly Asp Pro Pro Ala Pro
                725                 730

<210> SEQ ID NO 45
<211> LENGTH: 22
<212> TYPE: PRT
<213> ORGANISM: Artificial Sequence
<220> FEATURE:
<223> OTHER INFORMATION: Motif VI

<400> SEQUENCE: 45

Gln Ala Met Gly Arg Val Ile Arg Ser Pro Glu Asp Phe Gly Val Arg
1               5                   10                  15
Met Leu Val Asp Arg Arg
            20

<210> SEQ ID NO 46
<211> LENGTH: 651
<212> TYPE: PRT
<213> ORGANISM: Methanocaldococcus jannaschii

<400> SEQUENCE: 46

Met Glu Phe Lys Gly Tyr Ile Lys Glu Lys Phe Pro Tyr Pro Lys Val
1               5                   10                  15
Arg Glu Pro Gln Lys Arg Met Met Leu Lys Ile Tyr Glu Cys Ile Lys
            20                  25                  30
Asn Lys Arg Asn Leu Ile Val Glu Ala Pro Thr Gly Val Gly Lys Thr
        35                  40                  45
```

-continued

```
Leu Gly Tyr Leu Ile Pro Ala Leu Tyr Phe Ala Glu Arg Arg Lys Arg
 50                  55                  60

Val Leu Ile Leu Thr Glu Thr Ile Asp Gln Gln Val Arg Ile Tyr Glu
 65                  70                  75                  80

Asp Leu Ser Ser Leu Arg His Asn Leu Lys Val Ala Phe Leu Met Gly
                 85                  90                  95

Lys Ser Asn Phe Ile Cys Lys Ser Lys Gly Lys Ala Asn Arg Leu
                100                 105                 110

Tyr Cys Gln Leu Asn Lys Lys Cys Leu Tyr Arg Pro Asn Lys Arg Pro
                115                 120                 125

Ile Cys Tyr Cys Gly Thr Lys Lys Gln Pro Val Asn Leu Gly Asp Lys
130                 135                 140

Val Ile Tyr Tyr Cys Pro Tyr Cys Thr Cys Glu Tyr Gln Lys Ala Lys
145                 150                 155                 160

Ile Glu Ser Ile Leu Ala Asp Ile Val Val Met Asn Asn Ser Met Phe
                165                 170                 175

Tyr Tyr Ala Lys Glu Asp Ile Glu Ala Lys Arg Asp Ile Asp Ile Ile
                180                 185                 190

Ile Cys Asp Glu Ala His Lys Leu Glu Ser Ser Ile Arg Asn Thr Ser
                195                 200                 205

Thr Ile Ile Ile Asn Pro Glu Leu Pro Ile Asn Arg Leu Lys Tyr Met
210                 215                 220

Ala Ile His Tyr Ala Pro Asn Ile Leu Lys Lys Arg Leu Asp Ile Gly
225                 230                 235                 240

Asp Glu Asn Phe Trp Glu Ile Ile Glu Lys Tyr Leu Thr Ser Arg Gly
                245                 250                 255

Ile Asn Ile Asp Ile Cys Lys Glu Thr Ile Ile Phe Asp Gly Glu Asn
                260                 265                 270

Leu Ser Ser Trp Lys Tyr Lys Thr Glu Leu Ala Val Leu Gly Ala Ile
                275                 280                 285

Leu Asp Ala Tyr Tyr Gln Ile Asn Asn Ile Lys Asn Lys Ile Leu Arg
290                 295                 300

Phe Asn Glu Asn Glu Glu Ile Asp Arg Glu Glu Leu Arg Phe Glu Ile
305                 310                 315                 320

Asp Asn Lys Ala Leu Ile Ala Ile Glu Leu Asp Phe Ile His Lys Lys
                325                 330                 335

Lys Leu Ser Asp Leu Tyr Leu Leu Glu Phe Ile Glu Asn Ile Lys Asn
                340                 345                 350

Leu Arg Tyr Ile Asn Glu Asn Tyr Val Val Tyr Arg Ser Gly Asn Ser
                355                 360                 365

Leu Leu Cys Glu Pro Val Phe Val Ser His Leu Lys Glu Leu Tyr
                370                 375                 380

Gly Asn Ala Val Val Ile His Cys Ser Ala Thr Ile Gly Asn Leu Lys
385                 390                 395                 400

Met His Ala Leu Lys Thr Gly Leu Asp Lys Ala Glu Phe Leu Ile Leu
                405                 410                 415

Glu Ser Pro Phe Pro Lys Asn Arg Lys Lys Ile Ile Ala Leu Lys Asp
                420                 425                 430

Gly Val Asp Met Lys Tyr Glu Arg Lys Asp Arg Glu Lys Ala Asn Lys
                435                 440                 445

Asn Leu Leu Lys Ile Leu Glu Ala Ile Asn Gly Asn Ser Leu Val Leu
450                 455                 460

Phe Lys Ser Phe Glu Asp Leu Asp Ser Phe Tyr Lys Tyr Leu Lys Arg
```

```
                465                 470                 475                 480
        Glu Ile Thr Lys Thr Asn Ile Lys Asn Lys Asn Ile His Val Tyr Glu
                        485                 490                 495

Gln Gly Met Asp Gly Lys Glu Ala Lys Glu Leu Lys Glu Arg Phe Glu
                        500                 505                 510

Lys Ile Gly Gly Ile Leu Leu Ala Thr Gly Arg Phe Ala Glu Gly Val
                        515                 520                 525

Asp Ile Pro Gly Glu Ala Leu Val Gly Val Ile Asp Ser Leu Pro
                        530                 535                 540

Phe Pro Val Pro Thr Pro Leu Ile Leu Arg Glu Gln Lys Ile Leu Glu
        545                 550                 555                 560

Glu Arg Phe Lys Ile Arg Gly Val Arg Asp Ala His Trp Arg Ala Phe
                        565                 570                 575

Leu Met Thr Ser Phe Asp Arg Met Ala Arg Thr Leu Val Gln Met Ile
                        580                 585                 590

Gly Arg Leu Ile Arg Thr Glu Asn Asp Tyr Gly Val Val Ile Gln
                        595                 600                 605

Asp Lys Arg Phe Ala Asp Trp Val Gly Arg Val Met Arg Glu Lys Gly
                        610                 615                 620

Tyr Leu Lys Asp Asn Tyr Glu Val Met Ser Leu Asp Met Ala Ile Lys
        625                 630                 635                 640

Tyr Ile Pro Lys Phe Met Ser Gln Phe Lys Asn
                        645                 650

<210> SEQ ID NO 47
<211> LENGTH: 9
<212> TYPE: PRT
<213> ORGANISM: Artificial Sequence
<220> FEATURE:
<223> OTHER INFORMATION: Motif V

<400> SEQUENCE: 47

Leu Ala Thr Gly Arg Phe Ala Glu Gly
1               5

<210> SEQ ID NO 48
<211> LENGTH: 22
<212> TYPE: PRT
<213> ORGANISM: Artificial Sequence
<220> FEATURE:
<223> OTHER INFORMATION: Motif VI

<400> SEQUENCE: 48

Gln Met Ile Gly Arg Leu Ile Arg Thr Glu Asn Asp Tyr Gly Val Val
1               5                   10                  15

Val Ile Gln Asp Lys Arg
            20

<210> SEQ ID NO 49
<211> LENGTH: 550
<212> TYPE: PRT
<213> ORGANISM: Sulfolobus solfataricus

<400> SEQUENCE: 49

Met Glu Leu Arg Glu Trp Gln Ser Lys Ile Ala Glu Lys Ile Val Glu
1               5                   10                  15

Ala Leu Arg Asn Asn Phe Leu Val Ser Leu Gln Ala Pro Thr Gly Ser
            20                  25                  30

Gly Lys Thr Leu Phe Ala Leu Tyr Thr Ala Leu Lys Val Lys Pro Lys
```

-continued

```
             35                  40                  45
Val Ala Phe Val Val Arg Thr His Asn Glu Phe Phe Pro Val Tyr Arg
 50                  55                  60

Glu Leu Ser Leu His Phe Lys Asp Lys Lys Tyr Gly Phe Leu Val Gly
 65                  70                  75                  80

Lys Ser Ser Ala Cys Val Phe Ser Ser Asp Val Asp Ala Gln Asp
                 85                  90                  95

Ile Tyr Cys Asn Gly Cys Glu Ile Phe Asn Ala Ser Ala Val Thr Val
                100                 105                 110

Thr Asp Ser Pro Lys Val Ser Leu Asn Lys Leu Lys Glu Glu Gly Lys
                115                 120                 125

Lys Leu Gly Phe Cys Pro Tyr Tyr Ser Leu Leu Glu Thr Ile Lys Thr
                130                 135                 140

Ala Asp Val Ile Leu Leu Thr Tyr Pro Tyr Leu Phe Ile Pro Trp Leu
145                 150                 155                 160

Arg Glu Ser Leu Asp Ile Asn Trp Glu Asp Tyr Val Val Ile Val Asp
                165                 170                 175

Glu Ala His Asn Ile Glu Asn Val Ser Asn Ile Glu Glu Lys Lys Leu
                180                 185                 190

Asn Lys Arg Ile Ile Glu Met Ala Ile Ser Gln Ser His Ser Gln Asn
            195                 200                 205

Val Lys Val Ile Leu Glu Arg Leu Lys Glu Asn Val Glu Lys Ala Val
210                 215                 220

Tyr Ser Glu Asp Lys Tyr Ile Leu Ile Glu Lys Asp Lys Leu Asp Asn
225                 230                 235                 240

Ile Leu Pro Ser Asn Glu Glu Ile Glu Ile Leu Ser Glu Glu Tyr Asp
                245                 250                 255

Glu Ile Arg Lys Ile Met Ile Lys Asn Lys Thr Val Ser Arg Asn Tyr
                260                 265                 270

Leu Gly Ser Ile Leu Arg Phe Phe Asp Leu Val Asn Asp Glu Gly Ile
            275                 280                 285

Arg Val Phe Ser Tyr Ser Gly Ser Leu Ile Ala Lys Tyr Ile Ile Pro
290                 295                 300

Ser Tyr Phe Thr Asp Ile Leu Asn Asp Glu Lys Ile Thr Tyr Met Leu
305                 310                 315                 320

Met Ser Gly Thr Met Gln Pro Leu Asp Tyr Leu Arg Asn Ile Ile Gly
                325                 330                 335

Ile Lys Arg Lys Ile Leu Tyr Ile Asp Ala Glu Lys Val Met Lys Lys
                340                 345                 350

Arg Leu Thr Gly Thr Tyr Glu Cys Leu Ile Ser Ile Asp Val Thr Thr
            355                 360                 365

Thr Tyr Ser Leu Arg Ser Glu Gln Met Ala Arg Lys Tyr Ala Ser Tyr
            370                 375                 380

Leu Leu Lys Ile Phe Tyr Asn Ser Arg Arg His Val Leu Ala Ile Phe
385                 390                 395                 400

Pro Ser Tyr Glu Phe Met Arg Ile Val Ser Lys Phe Leu Asn Ile Arg
                405                 410                 415

Tyr Leu Ala Glu Asp Thr Glu Thr Ser Ile Glu Glu Ile Met Ser Asn
                420                 425                 430

Leu Lys Lys Glu Lys Thr Ile Ile Met Gly Ile Ala Arg Gly Lys Leu
            435                 440                 445

Ala Glu Gly Ile Glu Ile Val Glu Asn Gly Ser Ser Leu Ile Ser Asp
450                 455                 460
```

```
Val Ala Met Val Gly Ile Pro Tyr Pro Ile Asp Asp Tyr Leu Lys
465                 470                 475                 480

Ile Arg Val Glu Glu Ile Ser Lys Ile Leu Lys Lys Asp Ile Ser Asn
                485                 490                 495

Glu Leu Ile Ser Ile Gln Ala Leu Ile Ala Val Lys Gln Ser Ile Gly
            500                 505                 510

Arg Ala Ile Arg Gly Pro Thr Asp Asn Ala Thr Ile Trp Leu Leu Asp
                515                 520                 525

Lys Arg Tyr Asp Ser Leu Trp Trp Lys Glu Leu Asn Cys Leu Asn
530                 535                 540

Ala Arg Lys Ile Lys Leu
545                 550

<210> SEQ ID NO 50
<211> LENGTH: 9
<212> TYPE: PRT
<213> ORGANISM: Artificial Sequence
<220> FEATURE:
<223> OTHER INFORMATION: Motif V

<400> SEQUENCE: 50

Ile Ala Arg Gly Lys Leu Ala Glu Gly
1               5

<210> SEQ ID NO 51
<211> LENGTH: 22
<212> TYPE: PRT
<213> ORGANISM: Artificial Sequence
<220> FEATURE:
<223> OTHER INFORMATION: Motif VI

<400> SEQUENCE: 51

Gln Ser Ile Gly Arg Ala Ile Arg Gly Pro Thr Asp Asn Ala Thr Ile
1               5                   10                  15

Trp Leu Leu Asp Lys Arg
            20

<210> SEQ ID NO 52
<211> LENGTH: 551
<212> TYPE: PRT
<213> ORGANISM: Sulfolobus acidocaldarius

<400> SEQUENCE: 52

Met Leu Lys Leu Arg Asp Trp Gln Glu Lys Leu Lys Asp Lys Val Ile
1               5                   10                  15

Glu Gly Leu Arg Asn Asn Phe Leu Val Ala Leu Asn Ala Pro Thr Gly
                20                  25                  30

Ser Gly Lys Thr Leu Phe Ser Leu Val Ser Leu Glu Val Lys Pro
            35                  40                  45

Lys Val Leu Phe Val Val Arg Thr His Asn Glu Phe Tyr Pro Ile Tyr
        50                  55                  60

Arg Asp Leu Thr Lys Ile Arg Glu Lys Arg Asn Ile Thr Phe Ser Phe
65                  70                  75                  80

Leu Val Gly Lys Pro Ser Ser Cys Leu Tyr Ala Glu Lys Gly Ala Glu
                85                  90                  95

Ser Glu Asp Ile Pro Cys Lys Tyr Cys Glu Leu Lys Gly Ser Ile Val
            100                 105                 110

Glu Val Lys Thr Asp Asp Ser Pro Leu Ser Leu Val Lys Lys Leu Lys
        115                 120                 125
```

```
Lys Asp Gly Leu Gln Asp Lys Phe Cys Pro Tyr Tyr Ser Leu Leu Asn
            130                 135                 140

Ser Leu Tyr Lys Ala Asp Val Ile Ala Leu Thr Tyr Pro Tyr Phe Phe
145                 150                 155                 160

Ile Asp Arg Tyr Arg Glu Phe Ile Asp Ile Asp Leu Arg Glu Tyr Met
                165                 170                 175

Ile Val Ile Asp Glu Ala His Asn Leu Asp Lys Val Asn Glu Leu Glu
            180                 185                 190

Glu Arg Ser Leu Ser Glu Ile Thr Ile Gln Met Ala Ile Lys Gln Ser
                195                 200                 205

Lys Ser Glu Glu Ser Arg Arg Ile Leu Ser Lys Leu Leu Asn Gln Leu
210                 215                 220

Arg Glu Val Val Leu Pro Asp Glu Lys Tyr Ile Lys Val Glu Asn Val
225                 230                 235                 240

Pro Lys Leu Ser Lys Glu Glu Leu Glu Ile Leu Ala Asp Asp Tyr Glu
                245                 250                 255

Asp Ile Arg Lys Asp Ser Leu Lys Gln Gly Lys Val Asn Lys Ile His
                260                 265                 270

Ile Gly Ser Ile Leu Arg Phe Phe Ser Leu Leu Ser Ile Gly Ser Phe
            275                 280                 285

Ile Pro Phe Ser Tyr Ser Lys Arg Leu Val Ile Lys Asn Pro Glu Ile
            290                 295                 300

Ser Tyr Tyr Leu Asn Leu Leu Asn Asp Asn Glu Leu Ser Ile Ile Leu
305                 310                 315                 320

Met Ser Gly Thr Leu Pro Pro Arg Glu Tyr Met Glu Lys Val Trp Gly
                325                 330                 335

Ile Lys Arg Asn Met Leu Tyr Leu Asp Val Glu Arg Glu Ile Gln Lys
            340                 345                 350

Arg Val Ser Gly Ser Tyr Glu Cys Tyr Ile Gly Val Asp Val Thr Ser
                355                 360                 365

Lys Tyr Asp Met Arg Ser Asp Asn Met Trp Lys Arg Tyr Ala Asp Tyr
            370                 375                 380

Leu Leu Lys Ile Tyr Phe Gln Ala Lys Ala Asn Val Leu Val Val Phe
385                 390                 395                 400

Pro Ser Tyr Glu Ile Met Asp Arg Val Met Ser Arg Ile Ser Leu Pro
                405                 410                 415

Lys Tyr Val Glu Ser Glu Asp Ser Val Glu Asp Leu Tyr Ser Ala
                420                 425                 430

Ile Ser Ala Asn Asn Lys Val Leu Ile Gly Ser Val Gly Lys Gly Lys
            435                 440                 445

Leu Ala Glu Gly Ile Glu Leu Arg Asn Asn Asp Arg Ser Leu Ile Ser
            450                 455                 460

Asp Val Val Ile Val Gly Ile Pro Tyr Pro Pro Asp Asp Tyr Leu
465                 470                 475                 480

Lys Ile Leu Ala Gln Arg Val Ser Leu Lys Met Asn Arg Glu Asn Glu
                485                 490                 495

Glu Phe Leu Phe Lys Ile Pro Ala Leu Val Thr Ile Lys Gln Ala Ile
            500                 505                 510

Gly Arg Ala Ile Arg Asp Val Asn Asp Lys Cys Asn Val Trp Leu Leu
            515                 520                 525

Asp Lys Arg Phe Glu Ser Leu Tyr Trp Lys Lys Asn Leu Lys Cys Leu
530                 535                 540
```

Asn Ala Asn Lys Met Lys Leu
545                 550

<210> SEQ ID NO 53
<211> LENGTH: 9
<212> TYPE: PRT
<213> ORGANISM: Artificial Sequence
<220> FEATURE:
<223> OTHER INFORMATION: Motif V

<400> SEQUENCE: 53

Val Gly Lys Gly Lys Leu Ala Glu Gly
1               5

<210> SEQ ID NO 54
<211> LENGTH: 22
<212> TYPE: PRT
<213> ORGANISM: Artificial Sequence
<220> FEATURE:
<223> OTHER INFORMATION: Motif VI

<400> SEQUENCE: 54

Gln Ala Ile Gly Arg Ala Ile Arg Asp Val Asn Asp Lys Cys Asn Val
1               5                   10                  15

Trp Leu Leu Asp Lys Arg
            20

<210> SEQ ID NO 55
<211> LENGTH: 642
<212> TYPE: PRT
<213> ORGANISM: Thermococcus barophilus MP

<400> SEQUENCE: 55

Met Arg Asp Tyr Phe Pro Tyr Lys Ser Leu Arg Pro Asn Gln Glu Glu
1               5                   10                  15

Phe Ile Ser Leu Val Asp Glu Ala Val Arg Lys Gly Glu Asn Leu Ile
                20                  25                  30

Ile Glu Ala Pro Thr Gly Phe Gly Lys Thr Ile Ser Val Leu Ala Gly
            35                  40                  45

Val Leu Pro Tyr Ala Leu Ser Met Gly Phe Lys Val Val Tyr Leu Ala
        50                  55                  60

Arg Thr His Lys Gln Met Asp Arg Val Ile Glu Glu Leu Lys Glu Ile
65                  70                  75                  80

Asn Lys Ile Asn Pro Val Ser Gly Val Glu Phe Arg Ser Arg Lys Glu
                85                  90                  95

Leu Cys Leu His Ser Tyr Ile Gln Asn Phe Val Pro Asp Ala Tyr Asn
            100                 105                 110

Ala Met Ile Val Cys Lys Asn Leu Lys Lys Leu His Lys Cys Asp Tyr
        115                 120                 125

Phe Glu Asn Val Lys Lys Lys Asp Glu Phe Ser Glu Ile Val Glu
    130                 135                 140

Tyr Phe Leu Asn Ser Pro Ser Gln Pro Ile Glu Ile Leu Ser Tyr Ser
145                 150                 155                 160

Asn Leu Leu Glu Leu Cys Pro Tyr Glu Val Thr Arg Lys Val Gly Glu
                165                 170                 175

Lys Ala Asn Val Ile Val Ala Ser Tyr Leu Tyr Met Leu Asn Pro Ala
            180                 185                 190

Ile Arg Asn Ala Phe Ile Glu Ser Leu Gly Val Asp Tyr Glu Asp Leu
        195                 200                 205

```
Ile Val Ile Phe Asp Glu Ala His Asn Leu Pro Asn Gln Ala Ile Asp
    210                 215                 220
Val Leu Ser Asp Lys Ile Thr Leu Asn Ser Ile Thr Arg Ala Val Lys
225                 230                 235                 240
Glu Ala Glu Glu Tyr Asn Glu His Glu Ile Ala Asn Phe Leu Ser Ile
                245                 250                 255
Phe Leu Lys Gly Leu Glu Asn Leu Tyr Asn Glu Arg Leu Lys Asp Arg
            260                 265                 270
Glu Val Glu Glu Ile Pro Ile Leu Pro Glu Ser Ile Phe Ser His Val
        275                 280                 285
Phe Asp Ile Leu Asn Ile Ser Glu Arg Leu Leu Val Arg Ile Leu Arg
290                 295                 300
Glu Ile Val Glu Val Gly Asp Ala Ile Arg Glu Asp Lys Ile Glu Lys
305                 310                 315                 320
Asn Lys Pro Pro Arg Ser Tyr Val Gly Arg Val Gly Glu Phe Leu Leu
                325                 330                 335
Asn Trp Leu Ser Val Ile Gly Arg Glu Asp Tyr Leu Phe Ile Met Ser
            340                 345                 350
Lys Asp Arg Gly Phe Ser Leu Glu Leu Val Ala Leu Asp Pro Ser Lys
        355                 360                 365
Ala Leu Asp Phe Ile Asn Asp Ile Gln Ser Ala Ile Phe Met Ser Gly
370                 375                 380
Thr Leu Thr Pro Leu Glu Ala Phe Lys Asp Ile Met Gly Ile Glu Asn
385                 390                 395                 400
Ala Lys Leu Lys Lys Phe Pro Arg Met Val Lys Lys Glu Asn Ala Leu
                405                 410                 415
Val Leu Val Ala Lys Asp Val Ser Thr Arg Gly Glu Glu Arg Asn Leu
            420                 425                 430
Glu Leu Tyr Arg Lys Met Ala Glu Tyr Ile Val Glu Ala Val Lys Leu
        435                 440                 445
Ile Pro Lys Asn Val Gly Val Phe Thr Ala Ser Tyr Glu Val Leu Gln
    450                 455                 460
Gly Leu Leu Ser Ala Asn Val His Leu Arg Ile Glu Glu Val Gly
465                 470                 475                 480
Lys Lys Val Phe Ile Glu Lys Lys Asn Ala Ser Ser Lys Glu Asn Asp
                485                 490                 495
Ile Leu Val Arg Ala Phe Lys Glu Glu Ala Lys Arg Glu Gly Gly Val
            500                 505                 510
Leu Leu Gly Val Met Gly Gly Arg Asn Ser Glu Gly Gln Asp Tyr Ser
        515                 520                 525
Gly Asp Glu Met Asn Gly Val Val Leu Val Gly Ile Pro Tyr Ala Arg
530                 535                 540
Pro Thr Pro Arg Val Gln Ala Gln Ile Arg Tyr Phe Glu Lys Lys Phe
545                 550                 555                 560
Pro Arg Lys Gly Arg Tyr Tyr Gly Tyr Tyr Leu Pro Ala His Arg Lys
                565                 570                 575
Leu Val Gln Ala Ala Gly Arg Val His Arg Ser Ala Glu Glu Lys Gly
            580                 585                 590
Ala Ile Ile Ile Leu Asp Tyr Arg Val Leu Trp Ser Ser Ile Arg Lys
        595                 600                 605
Asp Leu Pro Asp Trp Met Asn Glu Thr Met Lys Pro Val Asn Leu Pro
610                 615                 620
Arg Met Lys Leu Tyr Leu Arg Arg Phe Tyr Arg Asn Leu Glu Glu Glu
```

```
                625                 630                 635                 640

Lys Val

<210> SEQ ID NO 56
<211> LENGTH: 22
<212> TYPE: PRT
<213> ORGANISM: Artificial Sequence
<220> FEATURE:
<223> OTHER INFORMATION: Motif VI

<400> SEQUENCE: 56

Gln Ala Ala Gly Arg Val His Arg Ser Ala Glu Glu Lys Gly Ala Ile
1               5                   10                  15

Ile Ile Leu Asp Tyr Arg
            20

<210> SEQ ID NO 57
<211> LENGTH: 729
<212> TYPE: PRT
<213> ORGANISM: Natrialba magadii

<400> SEQUENCE: 57

Met Ser Glu Thr Ala Gly Tyr Met Arg Phe Phe Pro Tyr Asp Gln Pro
1               5                   10                  15

Tyr Glu Asn Gln Arg Glu Ala Met Asp Arg Ile His Asn Ala Leu Val
            20                  25                  30

Arg Gly Gln Asn Val Leu Phe Glu Gly Ala Cys Gly Thr Gly Lys Thr
        35                  40                  45

Leu Ser Ser Leu Val Pro Ala Leu Glu Val Ala Arg Glu Glu Asp Lys
50                  55                  60

Thr Val Val Ile Thr Thr Asn Val His Gln Gln Met Arg Gln Phe Ile
65                  70                  75                  80

Ala Glu Ala Arg Ala Ile Thr Arg Glu Glu Pro Ile Arg Ala Val Val
                85                  90                  95

Phe Lys Gly Lys Gly Ser Met Cys His Ile Asp Val Gly Tyr Glu Glu
            100                 105                 110

Cys Gln Ala Leu Arg Asp Asn Thr Arg Ala Val Val Asp Ala Glu Gln
        115                 120                 125

Asp Lys Gln Gln Leu Glu Arg Arg Gln Arg Glu Leu Leu Thr Glu Ser
130                 135                 140

Gln Gln Gly Asp Gly Gly Ala Ala Asp Ala Arg Ser Ala Val Met Asp
145                 150                 155                 160

Glu Leu Glu Ser Ile Glu Glu Arg Leu Asp Asp Leu Glu Asp Gln Asn
                165                 170                 175

Val Cys Asp Tyr Tyr Arg Asn Asn Leu Thr Glu Asp Thr Asp Glu Phe
            180                 185                 190

Phe Gly Trp Leu Phe Glu Asp Val Arg Thr Pro Asp Glu Ile Tyr Glu
        195                 200                 205

Tyr Ala Glu Gln Arg Glu Leu Cys Gly Tyr Glu Leu Leu Lys Glu Gly
210                 215                 220

Ile Glu Gly Val Asp Leu Val Val Cys Asn Tyr His His Leu Leu Asp
225                 230                 235                 240

Ser Thr Ile Arg Glu Gln Phe Phe Arg Trp Leu Gly Arg Asp Pro Glu
                245                 250                 255

Asp Val Ile Ala Val Phe Asp Glu Ala His Asn Val Gly Asp Ala Ala
            260                 265                 270
```

-continued

Arg Glu His Ala Thr Arg Thr Cys Ser Glu Arg Thr Phe Glu Ser Ala
              275                 280                 285
Leu Asp Glu Leu Ala Asp Ala Asp Pro Arg Ala Glu Asp Ala Val
290                 295                 300
Asn Ala Leu Ser Ala Phe His Arg Ala Leu Val Glu Thr Tyr Glu Asp
305                 310                 315                 320
Ser Phe Gly Phe Gly Glu Arg Glu Arg Ile Gly Glu Asn Trp Glu Asp
                    325                 330                 335
Val Pro Ile Ala Asn Glu Gly Arg Arg Asp Asp Leu Thr Leu Glu Phe
                340                 345                 350
Leu Gln Arg Tyr Glu Gly Arg Gly Ile Gln Glu Asp Leu Glu Ala Ala
            355                 360                 365
Met Lys Leu Gly Gln Glu Leu Asp Ala Glu Tyr Glu Glu Ala Tyr Arg
370                 375                 380
Glu Gly Glu Thr Ala Thr Arg Thr Glu Cys Gln Thr Leu Gln Ala Ala
385                 390                 395                 400
Ala Phe Val Ser Ala Trp Met Asn Glu Gly Ser Lys Glu Gly Leu Tyr
                405                 410                 415
Pro Val Val Ala Val Thr Arg Asp Ala Gly Thr Asp Glu Val Tyr Gly
                420                 425                 430
Arg Ala Glu Ile Tyr Ser Cys Leu Pro Arg Gln Val Thr Gly Gln Leu
            435                 440                 445
Phe Glu Glu Val Ser Ala Thr Val Leu Met Ser Ala Thr Leu Gln Pro
450                 455                 460
Phe Asp Val Thr Glu Asp Val Leu Gly Leu Glu Lys Pro Val Thr Met
465                 470                 475                 480
Ala Tyr Gly Leu Gln Phe Pro Ala Asp Asn Arg Arg Thr Tyr Ala Val
                485                 490                 495
Glu Thr Pro Pro Leu Phe Ser Ser Asp Arg Asp Pro Ala Val Gln
                500                 505                 510
Glu Asp Val Thr Glu Thr Ile His Asp Ala Val Arg Met Thr Pro Gly
            515                 520                 525
Asn Thr Leu Thr Phe Phe Pro Asn Tyr Gly Glu Ala Ser Arg Tyr Ala
530                 535                 540
Glu Arg Leu Glu Ser Arg Ser Arg Ser Arg Ser Asn Val Thr
545                 550                 555                 560
Val Tyr Leu Asp Glu Pro Gly Gln Pro Val Glu Leu Arg Gln Glu
                565                 570                 575
Phe Ile Ala Asp Asp Gly Ala Val Leu Cys Thr Ser Leu Trp Gly Thr
                580                 585                 590
Leu Ala Glu Gly Val Ser Phe Asp Gly Asp Ala Gln Thr Val Leu
            595                 600                 605
Val Val Gly Val Pro Tyr Pro His Leu Asp Asp Arg Ala Glu Ala Val
            610                 615                 620
Gln Glu Ala Tyr Asp Ala Phe Asp Gly Thr Glu Thr Gly Trp Arg
625                 630                 635                 640
Tyr Ala Val Glu Ile Pro Thr Val Arg Lys Thr Arg Gln Ala Leu Gly
                645                 650                 655
Arg Val Ile Arg Ser Pro Glu Asp Gly Val Arg Ala Leu Leu Asp
                660                 665                 670
Arg Arg Tyr Ser Lys Gln Ala Lys Ser Asp Leu Gly Lys Tyr Ser Val
            675                 680                 685
Asn Ser Thr Phe Pro His Glu Glu Arg Glu Glu Leu Leu Asp Ile Gly

```
            690                 695                 700
Pro Glu Lys Leu Lys Phe Ala Met Leu Asn Phe Tyr Gly Asp His Asp
705                 710                 715                 720

Cys Tyr Asp Gly Asp Ala Pro Ala Pro
                725
```

<210> SEQ ID NO 58
<211> LENGTH: 22
<212> TYPE: PRT
<213> ORGANISM: Artificial Sequence
<220> FEATURE:
<223> OTHER INFORMATION: Motif VI

<400> SEQUENCE: 58

```
Gln Ala Leu Gly Arg Val Ile Arg Ser Pro Glu Asp Val Gly Val Arg
1               5                   10                  15

Ala Leu Leu Asp Arg Arg
                20
```

<210> SEQ ID NO 59
<211> LENGTH: 727
<212> TYPE: PRT
<213> ORGANISM: Haladaptatus paucihalophilus

<400> SEQUENCE: 59

```
Met Ser Thr Thr Asn Glu Tyr Met Arg Phe Phe Pro Tyr Asp Ser Pro
1               5                   10                  15

Tyr Glu Asn Gln Arg Glu Ala Met Asp Arg Ile Tyr Asn Gly Leu Thr
                20                  25                  30

Arg Gly Gln Asp Val Leu Phe Glu Gly Ala Cys Gly Thr Gly Lys Thr
            35                  40                  45

Leu Ser Ser Leu Val Pro Ala Leu Glu Phe Ala Arg Glu Glu Asp Lys
        50                  55                  60

Thr Val Val Ile Thr Thr Asn Val His Gln Gln Met Arg Gln Phe Val
65                  70                  75                  80

Thr Glu Ala Arg Glu Ile Thr Arg Lys Glu Pro Leu Arg Ala Val Val
                85                  90                  95

Phe Arg Gly Lys Gly Ser Met Cys His Ile Asp Val Asp Tyr Gln Glu
                100                 105                 110

Cys Gln Val Leu Arg Asp Asn Thr Tyr Glu Val Val Asp Lys Glu Arg
            115                 120                 125

Asp Lys Arg Glu Leu Glu Gln Arg Gln Ser Glu Leu Leu Ser Asp Met
        130                 135                 140

Gln Glu Gly Asp Ser Asn Ala Ala Glu Ala Arg Ser Ala Val Met Asp
145                 150                 155                 160

Glu Leu Glu Gln Ile Gln Asp Glu Val Glu Asn Leu Lys Glu Lys Asn
                165                 170                 175

Val Cys Glu Tyr Tyr Tyr Asn Asn Leu Thr Gly Asn Thr Glu Glu Phe
                180                 185                 190

Tyr Gln Trp Leu Tyr Asp Gly Val Arg Thr Pro Asp Asp Ile Tyr Glu
            195                 200                 205

Tyr Ala Glu Gln Gln His Met Cys Gly Tyr Leu Leu Lys Asp Gly
        210                 215                 220

Met Glu Gly Val Asp Leu Val Val Cys Asn Tyr His His Leu Leu Asp
225                 230                 235                 240

Pro Met Ile Arg Glu Gln Phe Phe Arg Trp Leu Gly Arg Asp Pro Glu
                245                 250                 255
```

-continued

Asp Val Ile Thr Ile Phe Asp Glu Ala His Asn Ile Glu Gly Thr Ala
                260                 265                 270

Arg Asp His Ala Ser Arg Thr Leu Thr Glu Asn Thr Ile Asp Ser Ala
            275                 280                 285

Leu Asp Glu Leu Gln Glu Ser Asp Asp Phe Arg Ser Glu Ala Gly Phe
        290                 295                 300

Asn Val Leu Ala Ala Phe Gln Arg Ala Leu Lys Ala Thr Tyr Glu Asp
305                 310                 315                 320

Ser Phe Gly Phe Gly Glu Arg Glu Ala Val Gly Glu Asn Trp Gln Asp
                325                 330                 335

Val Ala Val Ala Asn Glu Asn Lys Arg Asp Asp Leu Thr Leu Asn Phe
            340                 345                 350

Leu Gln Glu Tyr Ser Gly Lys Gly Ile Asp Ala Glu Leu Asp Asp Ala
        355                 360                 365

Leu Ser Leu Ala Lys Glu Leu Asp Gln Lys Tyr Glu Asp Ala Tyr Lys
    370                 375                 380

Glu Gly Asp Ala Thr Thr Arg Lys Glu Cys Gln Thr Leu Gln Ala Ala
385                 390                 395                 400

Ala Phe Val Lys Ser Tyr Met Asp Glu Gly Ala Glu Leu Gly Gln Tyr
                405                 410                 415

Pro Val Val Ala Val Arg Arg Asp Glu Gly Thr Asp Gln Val Tyr Gly
            420                 425                 430

Arg Ala Glu Leu Tyr Thr Cys Ile Pro Arg Glu Val Thr Gln Ala Leu
        435                 440                 445

Phe Asp Glu Val Tyr Ala Thr Val Leu Met Ser Ala Thr Leu Arg Pro
    450                 455                 460

Phe Asp Val Leu Ser Asp Val Leu Gly Leu Ser Glu Pro Val Thr Leu
465                 470                 475                 480

Ala Tyr Gly Leu Gln Phe Pro Glu Glu Asn Arg Arg Thr Phe Ala Ala
                485                 490                 495

Glu Thr Pro Ala Leu Phe Ala Ser Glu Arg Ser Asp Pro Glu Thr Gln
            500                 505                 510

Glu Thr Ile Ala Glu Ala Leu Thr Asp Ala Val Arg Phe Thr Ala Gly
        515                 520                 525

Asn Thr Leu Val Phe Phe Pro Ser Tyr Ala Glu Ala Glu Arg Tyr Arg
    530                 535                 540

Asp Leu Val Arg Asn Arg Val Asp Ala Thr Leu Tyr Phe Asp Glu Ala
545                 550                 555                 560

Gly Thr Pro Val Glu Glu Leu Arg Gln Gln Phe Thr Ser Asp Gly Asn
                565                 570                 575

Gly Val Leu Phe Thr Ser Leu Trp Gly Thr Leu Ala Glu Gly Val Ser
            580                 585                 590

Phe Asp Gly Asp Asp Ala Arg Thr Val Val Val Gly Val Pro Tyr
        595                 600                 605

Pro His Leu Asp Asp Arg Met Asp Ala Val Gln Asp Ala Tyr Asp Thr
    610                 615                 620

Val Phe Ala Asp Arg Ser Gly Arg Asn Ser Gly Trp Glu Tyr Ala Val
625                 630                 635                 640

Glu Ile Pro Thr Ile Arg Lys Thr Arg Gln Ala Leu Gly Arg Val Ile
                645                 650                 655

Arg Ser Pro Glu Asp Phe Gly Val Arg Ile Leu Leu Asp Lys Arg Tyr
            660                 665                 670

```
Thr Glu Lys Ser Val Arg Glu Met Gly Lys Tyr Ser Val Arg Glu Thr
            675                 680                 685

Phe Pro Pro Glu Glu Arg Gly Glu Thr Ile Asp Ile Ala Pro Glu Lys
        690                 695                 700

Leu Lys Phe Ala Met Leu Asn Phe Phe Thr Asp Lys Asp Ala Trp Asp
705                 710                 715                 720

Gly Asp Pro Pro Lys Pro Gln
                725

<210> SEQ ID NO 60
<211> LENGTH: 22
<212> TYPE: PRT
<213> ORGANISM: Artificial Sequence
<220> FEATURE:
<223> OTHER INFORMATION: Motif VI

<400> SEQUENCE: 60

Gln Ala Leu Gly Arg Val Ile Arg Ser Pro Glu Asp Phe Gly Val Arg
1               5                   10                  15

Ile Leu Leu Asp Lys Arg
            20

<210> SEQ ID NO 61
<211> LENGTH: 723
<212> TYPE: PRT
<213> ORGANISM: Haloterrigena turkmenica

<400> SEQUENCE: 61

Met Ser Glu Thr Ala Gly Tyr Met Arg Phe Pro Tyr Asp Gln Pro
1               5                   10                  15

Tyr Glu Asn Gln Arg Glu Ala Met Asp Arg Ile His Asn Ser Leu Thr
            20                  25                  30

Arg Gly Gln Asp Val Leu Phe Glu Gly Ala Cys Gly Thr Gly Lys Thr
        35                  40                  45

Leu Ser Ser Leu Val Pro Ala Leu Glu Val Ala Arg Glu Gln Asp Lys
    50                  55                  60

Thr Val Val Ile Thr Thr Asn Val His Gln Gln Met Arg Gln Phe Val
65                  70                  75                  80

Ala Glu Ala Arg Ala Ile Thr Arg Glu Glu Asp Ile Arg Ala Ile Val
                85                  90                  95

Phe Lys Gly Lys Ser Ser Met Cys His Ile Asp Val Gly Tyr Glu Glu
            100                 105                 110

Cys Gln Ala Leu Arg Asp Asn Thr Arg Ala Val Val Asp Ala Glu Arg
        115                 120                 125

Asp Lys Arg Gln Leu Glu Arg Arg Gln Arg Glu Leu Leu Glu Glu Ser
    130                 135                 140

Gln Gly Gly Asp Gly Gly Ala Ala Asp Ala Arg Ser Ala Val Met Asp
145                 150                 155                 160

Glu Leu Glu Ser Ile Glu Glu Arg Leu Glu Asp Leu Glu Glu Gln Asn
                165                 170                 175

Val Cys Asp Tyr Tyr Arg Asn Asn Leu Thr Gln Asp Thr Asp Asp Phe
            180                 185                 190

Phe Ala Trp Leu Phe Glu Asp Val Arg Thr Pro Glu Glu Ile Tyr Glu
        195                 200                 205

Tyr Ala Glu Arg Glu Gly Phe Cys Gly Tyr Glu Leu Leu Lys Glu Gly
    210                 215                 220

Ile Glu Gly Val Asp Leu Val Val Cys Asn Tyr His His Leu Leu Asp
```

```
               225                 230                 235                 240
          Ser Met Ile Arg Glu Gln Phe Phe Arg Trp Leu Gly Arg Asp Pro Glu
                              245                 250                 255
          Asp Val Ile Ala Val Phe Asp Glu Ala His Asn Val Glu Asp Ala Ala
                              260                 265                 270
          Arg Glu His Ala Thr Arg Thr Cys Ser Glu Arg Thr Phe Asp Ser Ala
                              275                 280                 285
          Leu Asp Glu Leu Ala Asp Ala Asp Pro Arg Ser Glu Asp Ala Ala
              290                 295                 300
          Asn Val Leu Ser Ala Phe His Arg Ala Leu Val Glu Thr Tyr Glu Asp
          305                 310                 315                 320
          Ser Phe Gly Phe Gly Glu Arg Glu Arg Ile Asp Glu Asn Trp Glu Asp
                              325                 330                 335
          Ile Ser Ile Ala Asn Glu Asp Arg Lys Asp Leu Thr Leu Glu Phe
                              340                 345                 350
          Leu Gln Arg Tyr Ser Gly Arg Gly Ile Glu Asp Asp Leu Glu Ala Ala
                              355                 360                 365
          Met Lys Leu Gly Gln Glu Leu Asp Glu Gln Tyr Glu Ala Tyr Arg
              370                 375                 380
          Glu Gly Glu Thr Ala Thr Arg Thr Glu Cys Gln Thr Leu Gln Ala Ala
          385                 390                 395                 400
          Ala Phe Val Ser Ala Trp Met Asn Glu Gly Ser Lys Glu Gly Leu Tyr
                              405                 410                 415
          Pro Val Val Ser Val Thr Arg Asp Ala Gly Thr Asp Glu Ile Tyr Gly
                              420                 425                 430
          Arg Ala Glu Leu Tyr Thr Cys Leu Pro Arg Gln Val Thr Gly Arg Leu
                              435                 440                 445
          Phe Glu Glu Val Tyr Gly Thr Ile Leu Met Ser Ala Thr Leu Gln Pro
              450                 455                 460
          Phe Asp Val Thr Glu Asp Val Leu Gly Leu Glu Asp Pro Val Thr Met
          465                 470                 475                 480
          Ala Tyr Gly Leu Gln Phe Pro Ala Glu His Arg Arg Thr Tyr Ala Val
                              485                 490                 495
          Glu Thr Pro Pro Leu Phe Ser Ser Asp Arg Asp Pro Ala Val Gln
                              500                 505                 510
          Glu Glu Val Ala Glu Thr Ile His Asp Ala Val Arg Met Thr Pro Gly
              515                 520                 525
          Asn Thr Leu Ala Phe Phe Pro Asn Tyr Gly Glu Ala Glu Arg Tyr Ala
              530                 535                 540
          Lys Arg Leu Glu Gly Arg Thr Glu Lys Thr Val Tyr Leu Asp Glu Pro
          545                 550                 555                 560
          Gly Thr Ser Val Glu Glu Leu Arg Gln Gln Phe Val Ala Asp Asp Gly
                              565                 570                 575
          Ala Val Leu Cys Thr Ser Leu Trp Gly Thr Leu Ala Glu Gly Val Ser
                              580                 585                 590
          Phe Asp Gly Asp Asp Ala His Thr Val Leu Val Gly Val Pro Tyr
                              595                 600                 605
          Pro His Leu Asp Asp Arg Ala Glu Ala Val Gln Glu Ala Tyr Asp Ala
              610                 615                 620
          Ala Phe Asp Gly Thr Glu Thr Gly Trp Arg Tyr Ala Val Glu Ile Pro
          625                 630                 635                 640
          Thr Val Arg Lys Thr Arg Gln Ala Leu Gly Arg Val Ile Arg Ser Pro
                              645                 650                 655
```

Glu Asp Val Gly Val Arg Ala Leu Leu Asp Arg Arg Tyr Ser Arg Ser
            660                 665                 670

Ala Lys Ser Asp Leu Gly Arg Tyr Ser Val Asn Gly Thr Phe Pro His
    675                 680                 685

Glu Glu Arg Glu Glu Leu Ile Asp Ile Asp Pro Glu Lys Leu Lys Phe
690                 695                 700

Ser Met Leu Asn Phe Tyr Gly Asp His Asp Ala Tyr Asp Gly Glu Thr
705                 710                 715                 720

Pro Ala Pro

<210> SEQ ID NO 62
<211> LENGTH: 779
<212> TYPE: PRT
<213> ORGANISM: Methanosarcina mazeii

<400> SEQUENCE: 62

Met Met Gln Lys Asn Gly Tyr Met Arg Tyr Phe Thr Lys Lys Ser Cys
1               5                   10                  15

Tyr Pro Asn Gln Ser Glu Ala Met Asp Lys Ile His Ser Ala Leu Gln
            20                  25                  30

Asn Glu Lys Ile Val Leu Phe Glu Gly Ala Cys Gly Thr Gly Lys Thr
        35                  40                  45

Leu Ser Ala Leu Ala Pro Ala Leu His Ala Gly Lys Lys Leu Asn Lys
    50                  55                  60

Val Val Ile Ile Val Thr Asn Val His Gln Gln Met Val Gln Phe Ile
65                  70                  75                  80

Asn Glu Ala Arg Asp Ile Asn Arg Asp Asn Ser Ile Lys Thr Ile Val
                85                  90                  95

Phe Lys Gly Lys Ala Ser Met Cys Pro Asp Asn Leu Asp Tyr Glu Glu
            100                 105                 110

Cys Arg Leu Lys Gly Glu Asn Thr Tyr Asp Leu Leu Asp Phe Glu Arg
        115                 120                 125

Glu Val Ser Ser Lys Glu Lys Glu Leu Lys Asp Ala Phe Glu Lys His
    130                 135                 140

Lys Lys Ser Lys Asp Pro Ala Leu Tyr Ile Leu Arg Asn Glu Leu Glu
145                 150                 155                 160

Lys Glu Leu Asp Glu Ala Arg Lys Lys Ala Gln Ser Leu Arg Asn His
                165                 170                 175

Ser Cys Ser Arg Leu Tyr Glu Val Leu Lys Phe Glu Ser Ser Glu Phe
            180                 185                 190

Ser Ser Trp Leu Phe Ser Asp Val Arg Ser Pro Glu Glu Ile Met Glu
        195                 200                 205

Tyr Ala Glu Asp Arg Gly Met Cys Gly Tyr Glu Leu Leu Lys Lys Glu
    210                 215                 220

Leu Lys Asn Thr Glu Leu Leu Ile Cys Asn Phe His His Val Leu Ser
225                 230                 235                 240

Ala Asp Ile Phe Met Thr Leu Leu Lys Trp Leu Glu Arg Asp Pro Glu
                245                 250                 255

Asp Val Ile Leu Ile Phe Asp Glu Ala His Asn Ile Glu Ala Ser Ala
            260                 265                 270

Arg Ser His Ser Ser Ile Met Leu Ser Glu Leu Thr Val Glu Lys Ala
        275                 280                 285

Leu Ser Glu Val Gly Glu Ile Pro Glu Pro Glu Ser Ser Pro Val Phe
    290                 295                 300

```
Gly Gly Gly Ser Phe Ser Gly Thr Gly Ile Pro Leu Asp Glu Asp Tyr
305                 310                 315                 320

Ala Ser Arg Ile Tyr Ala Arg Arg Leu Phe Ser Cys Leu Leu Thr Ala
                325                 330                 335

Ile Arg Asp Thr Tyr Asp Ser Lys Leu Lys Phe Gly Glu Arg Asn Arg
            340                 345                 350

Leu Gly Lys His Trp Gln Asp Ile Gln Ile Ser Asp Pro Tyr Glu Arg
        355                 360                 365

His Asp Val Leu Lys Ala Arg Phe Leu Arg Asp Ala Gln Lys Glu Gly
    370                 375                 380

Phe Ala Asp Glu Glu Thr Val Leu Thr Arg Leu Arg Glu Ile Gly Glu
385                 390                 395                 400

Phe Gly Gly Arg Leu Glu Glu Ile Tyr Ala Glu Asn Tyr Lys Lys Gly
                405                 410                 415

Leu Leu Ser Val Pro Lys Arg Ser Gln Ile Arg Tyr Val Ala Asp Phe
                420                 425                 430

Leu Ser Ser Tyr Leu Val Leu Ser Asp Arg Gln Asn Tyr Tyr Pro Ile
            435                 440                 445

Leu Asn Met Arg Arg Asp Phe Lys Ser Asp Arg Val Val Gly Arg Leu
        450                 455                 460

Glu Leu Phe Thr Cys Ile Pro Lys Asn Val Thr Gln Pro Leu Leu Asp
465                 470                 475                 480

Ser Val Tyr Ser Ala Val Leu Met Ser Ala Thr Leu Arg Pro Phe Glu
                485                 490                 495

Met Val Arg Ser Thr Leu Gly Ile Ser Arg Glu Val Glu Glu Ile Thr
                500                 505                 510

Tyr Gly Thr Thr Phe Pro Gln Glu Arg Arg Leu Thr Leu Ala Val Ser
            515                 520                 525

Val Pro Pro Leu Phe Ala Lys Asn Arg Asp Ser Pro Glu Thr Leu Glu
        530                 535                 540

Gly Leu Arg Glu Ala Leu Leu Ala Ala Thr Ala Ala Ser Pro Gly Asn
545                 550                 555                 560

Val Ile Ile Tyr Phe Gln Ser Tyr Ala Glu Ala Leu Arg Tyr Thr Lys
                565                 570                 575

Leu Leu Glu Pro Glu Leu Ser Ile Pro Ile Phe Leu Asp Glu Val Gly
                580                 585                 590

Val Ser Ala Gln Glu Ile Arg Pro Lys Phe Phe Lys Ile Gly Glu Gln
            595                 600                 605

Gly Gly Lys Ala Val Leu Ile Thr Tyr Leu Trp Gly Thr Leu Ser Glu
        610                 615                 620

Gly Val Asp Phe Arg Asp Ser Arg Gly Arg Thr Val Ile Val Val Gly
625                 630                 635                 640

Val Gly Tyr Pro Ala Leu Asn Asp Arg Ile Lys Ala Val Glu Ser Ala
                645                 650                 655

Tyr Asp Thr Val Phe Gly Cys Gly Gly Trp Glu Phe Ala Val Gln
                660                 665                 670

Val Pro Thr Ile Arg Lys Val Arg Gln Ala Met Gly Arg Val Val Arg
            675                 680                 685

Ser Pro Gly Asp Phe Gly Val Arg Ile Leu Asp Ala Arg Tyr Gln
        690                 695                 700

Gly Ser Gln Val Arg Lys Leu Gly Lys Phe Ser Val Phe Gly Tyr Phe
705                 710                 715                 720
```

-continued

```
Pro Pro Glu Glu Ser Arg Glu Phe Ile Asp Val Ala Pro Lys Asp Val
                725                 730                 735

Gly Ser Leu Val Glu Glu Phe Phe Ala Asn Thr Leu Pro Tyr Asn Pro
            740                 745                 750

Glu Lys Ile Glu Thr Glu Lys Lys Gly Pro Glu Ser Pro Ala Ser Gly
        755                 760                 765

Arg Leu Glu Phe Gly Ser Leu Ala Glu Lys Leu
    770                 775

<210> SEQ ID NO 63
<211> LENGTH: 454
<212> TYPE: DNA
<213> ORGANISM: Artificial Sequence
<220> FEATURE:
<223> OTHER INFORMATION: Polynucleotide used in the Examples
<220> FEATURE:
<221> NAME/KEY: misc_feature
<222> LOCATION: (1)..(4)
<223> OTHER INFORMATION: 2'-O-Methyl-Uracil

<400> SEQUENCE: 63 nnnnttttt ttttttttt ttttttttt ttttttttt ttttttttt ttttggttgt      60 ttctgttggt gctgatattg cttttgatgc cgaccctaaa tttttgcct gtttggttcg   120 ctttgagtct tcttcggttc cgactaccct cccgactgcc tatgatgttt atcctttgaa  180
tggtcgccat gatggtggtt attataccgt caaggactgt gtgactattg acgtccttcc  240
ccgtacgccg ggcaataacg tttatgttgg tttcatggtt tggtctaact ttaccgctac  300
taaatgccgc ggattggttt cgctgaatca ggttattaaa gagattattt gtctccagcc  360
acttaagtga ggtgatttat gtttggtgct attgctggcg gtattgcttc tgctcttgct  420
ggtggcgcca tgtctaaatt gtttggaggc ggtc                             454

<210> SEQ ID NO 64
<211> LENGTH: 28
<212> TYPE: DNA
<213> ORGANISM: Artificial Sequence
<220> FEATURE:
<223> OTHER INFORMATION: Polynucleotide used in the Examples

<400> SEQUENCE: 64
tgaccgcctc caaacaattt agacatgg                                    28

<210> SEQ ID NO 65
<211> LENGTH: 57
<212> TYPE: DNA
<213> ORGANISM: Artificial Sequence
<220> FEATURE:
<223> OTHER INFORMATION: Polynucleotide used in the Examples

<400> SEQUENCE: 65
agcgactaac aaacacaatc tgatggcttt tttttttttt tttttttttt ttttttt    57

<210> SEQ ID NO 66
<211> LENGTH: 79
<212> TYPE: DNA
<213> ORGANISM: Artificial Sequence
<220> FEATURE:
<223> OTHER INFORMATION: Polynucleotide used in the Examples

<400> SEQUENCE: 66 cccccccac ccccccccac ccccccccac cccccccccc tattctgttt atgtttcttg   60
tttgttagcc ctattctgt                                              79
```

```
<210> SEQ ID NO 67
<211> LENGTH: 40
<212> TYPE: DNA
<213> ORGANISM: Artificial Sequence
<220> FEATURE:
<223> OTHER INFORMATION: Polynucleotide used in the Examples

<400> SEQUENCE: 67
acagaatagg gctaacaaac aagaaacata aacagaatag                             40

<210> SEQ ID NO 68
<211> LENGTH: 40
<212> TYPE: DNA
<213> ORGANISM: Artificial Sequence
<220> FEATURE:
<223> OTHER INFORMATION: Polynucleotide used in the Examples

<400> SEQUENCE: 68
ctattctgtt tatgtttctt gtttgttagc cctattctgt                             40
```